United States Patent
Tang et al.

(10) Patent No.: US 11,649,509 B2
(45) Date of Patent: May 16, 2023

(54) ANASTASIS BIOSENSOR CASPASE TRACKER

(71) Applicant: THE JOHNS HOPKINS UNIVERSITY, Baltimore, MD (US)

(72) Inventors: Ho Lam Hogan Tang, Baltimore, MD (US); Ho Man Holly Tang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 187 days.

(21) Appl. No.: 16/763,849

(22) PCT Filed: Nov. 16, 2018

(86) PCT No.: PCT/US2018/061428
§ 371 (c)(1),
(2) Date: May 13, 2020

(87) PCT Pub. No.: WO2019/099769
PCT Pub. Date: May 23, 2019

(65) Prior Publication Data
US 2020/0283857 A1    Sep. 10, 2020

Related U.S. Application Data

(60) Provisional application No. 62/587,201, filed on Nov. 16, 2017.

(51) Int. Cl.
*C07K 14/00* (2006.01)
*C12Q 1/34* (2006.01)
*C12Q 1/6897* (2018.01)

(52) U.S. Cl.
CPC ............ *C12Q 1/6897* (2013.01); *C07K 14/00* (2013.01); *C12Q 1/34* (2013.01); *G01N 2333/96413* (2013.01); *G01N 2510/00* (2013.01)

(58) Field of Classification Search
CPC ............ C07K 2319/00; C07K 2319/03; C07K 2319/50; C07K 2319/60; C07K 14/00; C12N 9/96; C12Q 1/34
See application file for complete search history.

(56) References Cited

U.S. PATENT DOCUMENTS

| 7,354,735 B2 | 4/2008 | Chang et al. |
| 2002/0132327 A1 | 9/2002 | Hay et al. |
| 2007/0231865 A1 | 10/2007 | Spears et al. |
| 2009/0131270 A1 | 5/2009 | Taylor et al. |
| 2009/0298089 A1 | 12/2009 | Rossner et al. |

FOREIGN PATENT DOCUMENTS

| WO | 1999025840 A1 | 5/1999 |
| WO | 2000073802 A1 | 7/2000 |
| WO | 2001/075453 A2 | 10/2001 |
| WO | 2006/017751 A2 | 2/2006 |
| WO | 2008/155133 A2 | 12/2008 |
| WO | 2013/134499 A1 | 9/2013 |

OTHER PUBLICATIONS

Sawicki, et al., On the recovery of transcription after inhibition by actinomycin D. J Cell Biol 55, 299-309. (1972).
Stephens, et al., Massive genomic rearrangement acquired in a single catastrophic event during cancer development. Cell 144, 27-40. (2011).
Stratton, et al., The cancer genome. Nature 458, 719-724. (2009).
Susin, et al., Molecular characterization of mitochondrial apoptosis-inducing factor. Nature 397, 441-446. (1999).
Takemoto, et al., Spatio-temporal activation of caspase revealed by indicator that is insensitive to environmental effects. J Cell Biol 160, 235-243. (2003).
Jaiswal, et al., Long-term multiple color imaging of live cells using Quantum Dot bioconjugates. Nat Biotechnol 21, 47-51. (2003).
Johnstone, et al., Apoptosis: a link between cancer genetics and chemotherapy. Cell 108, 153-164. (2002).
Kroemer, et al., Classification of cell death: recommendations of the Nomenclature Committee on Cell Death 2009. Cell Death Differ 16, 3-11. (2009).
Li, et al., Endo nuclease G is an apoptotic DNase when released from mitochondria. Nature 412, 95-99. (2001).
Zurlo, et al., Characterization of a primary hepatocyte culture system for toxicological studies. In Vitro Cell Dev Biol Anim 32, 211-220 (1996).
Liu, et al., Chromosome catastrophes involve replication mechanisms generating complex genomic rearrangements. Cell 146, 889-903. (2011).
Liu, et al., DFF, a heterodimeric protein that functions downstream of caspase-3 to trigger DNA fragmentation during apoptosis. Cell 89, 175-184 (1997).
Ditzel, et al., Degradation of DIAP1 by the N-end rule pathway is essential for regulating apoptosis. Nat Cell Biol 5, 467-473. (2003).
Badea, et al., A noninvasive genetic/pharmacologic strategy for visualizing cell morphology and clonal relationships in the mouse. J Neurosci 15, 2313-2322 (2003).
Salinas, et al., Stress-induced gem1 cellapoptosis is by a p53 independent pathway in Caenorhabditis elegans. Cell Death Differ 13,2 129-2139. (2006).

(Continued)

Primary Examiner — Karen Cochrane Carlson
(74) Attorney, Agent, or Firm — Johns Hopkins Technology Ventures

(57) ABSTRACT

The present invention relates to the field of anastasis, i.e., the process of reversal of apoptosis. More specifically, the present invention provides methods and compositions useful for studying anastasis. In one embodiment, a tracking construct of the present invention comprises Lyn11-NES-ERT2-DEVD-rtTA-3xFLAG-DEVD-ERT2-NES. In another embodiment, a construct comprises Lyn11-NES-DEVD-rtTA-3xFLAG. In a further embodiment, a construct comprises ERT2-DEVD-rtTA-3XFLAG-DEVD-ERT2.

20 Claims, 10 Drawing Sheets

Specification includes a Sequence Listing.

(56) References Cited

OTHER PUBLICATIONS

Logue, et al., Expression, purification and use of recombinant annexin V for the detection of apoptotic cells. Nat Protoc 4, 1383-1395. (2009).
Goyal, et al., Induction of apoptosis by *Drosophila* reaper, hid and grim through inhibition of IAP function. EMBO J 19, 589-97 (2000).
Garg, et al., Apoptosis and heart failure: clinical relevance and therapeutic target. JMol Cell Cardiol 38, 73-9 (2005).
Venkatachalam, et al., Motor deficit in a *Drosophila* model of mucolipidosis type IV due to defective clearance of apoptotic cells. Cell 135, 838-51 (2008).
Macleod, et al., Cytogenetic harvesting of commonly used tumor cell lines. Nat Protoc 2, 372-3 82. (2007).
Ranganathan, Matter of Life or Death. Science 299, 1677-1679 (2003).
Li, et al., Selective anticancer strategies via intervention of the death pathways relevant to cell transformation. Cell Death Differ 15, 1197-210 (2008).
Abbott, Ultrastructure of cell death in gamma- or X-irradiated imaginal wing discs of *Drosophila*. Radiat Res 96, 611-27 (1983).
Masters, HeLa cells 50 years on: the good, the bad and the ugly. Nat Rev Cancer2, 315-319. (2002).
Kitamoto, Conditional modification of behavior in *Drosophila* by targeted expression of a temperature-sensitive shibire allele in defined neurons. JNeurobiol 47, 81-92 (2001).
Silva, et al., ATM is required for telomere maintenance and chromosome stability during *Drosophila* development. Curr Biol 14, 1341-7 (2004).
Mollereau, et al., Photoreceptor differentiation in *Drosophila*: from immature neurons to functional photoreceptors. Dev Dyn 232, 585-92 (2005).
Gambis, et al., Two-color in vivo imaging of photoreceptor apoptosis and development in *Drosophila*. Dev Biol 351, 128-34 (2011).
Pichaud, et al., A new visualization approach for identifying mutations that affect differentiation and organization ofthe *Drosophila ommatidia*. Development 128, 815-26 (2001).
Geisbrecht, et al., A role for *Drosophila* IAP1-mediated caspase inhibition in Racdependent cell migration. Cell 118, 111-25 (2004).
Helfer, et al., Caspase-8 promotes cell motility and calpain activity under nonapoptotic conditions. Cancer Res 66, 4273-8 (2006).
Malhi, et al., Hepatocyte death: a clear and present danger. Physiol Rev 90, 1165-94 (2010).
Lin, et al., Mitochondrial dysfunction and oxidative stress in neurodegenerative diseases. Nature 443, 787-95 (2006).
Yang, et al., Excessive Dpp signaling induces cardial apoptosis through dTAKI and dJNK during late embryogenesis of *Drosophila*. JBiomed Sci 18, 85 (2011).
Tain, et al., *Drosophila* HtrA2 is dispensable for apoptosis but acts downstream of PINK 1 independently from Parkin. Cell Death Differ 16, 1118-25 (2009).
Stoller, et al., Cre reporter mouse expressing a nuclear localized fusion of GFP and betagalactosidase reveals new derivatives of Pax3-expressing precursors. Genesis 46, 200-4 (2008).
Cordeiro, et al., Imaging multiple phases of neurodegeneration: a novel approach to assessing cell death in vivo. Cell Death Dis 1, e3 (2010).
Youssef, et al., Retinal light toxicity. Eye (Loud) 25, 1-14 (2011).
Saito, et al., Involvement of ceramide in ethanol-induced apoptotic neurodegeneration in the neonatal mouse brain. JNeurochem 115, 168-77 (2010).
Waldmeier, et al., Interrupting apoptosis in neurodegenerative disease: potential for effective therapy? Drug Discov Today 9, 210-218. (2004).
McClintock, The significance of responses of the genome to challenge. Science 226, 792-801. (1984).
Narula, et al., Apoptosis in heart failure: release of cytochrome c frommitochondria and activation of caspase-3 in human cardiomyopathy. Proc Natl Acad Sci USA 96, 8144-8149. (1999).
Olive, et al., The comet assay: a method to measure DNA damage in individual cells. Nat Protoc 1, 23-29.(2006).
Reed, et al., Postmitochondrial regulation of apoptosisduring heart failure. Proc Natl Acad Sci USA 96, 7614-7616. (1999).
Rosenberg, Evolving responsively: adaptive mutation. Nat Rev Genet 2, 504-515. (2001).
Ross, Induction of cell death by radiotherapy. Endocr Related Cancer 6, 41-44. (1999).
Bloom, "Induced chromosomal aberrations: biological and clinical significance" The Journal of Pediatrics, vol. 81, No. 1, Jul. 1972.
Albeck, J., "Quantitative analysis of pathways controlling extrinsic apoptosis in single cells" Molecular Cell 30, Apr. 11, 2008, pp. 11-25.
Extended European Search Report dated May 18, 2020 for related EPO application 17870867.3.
Chambers, et al., Sequential gene targeting to make chimeric tumor models with de novo chromosomal abnormalities. Cancer Res. Mar. 1, 2014;74(5):1588-97.
Wang, et al., Intersectional Cre Driver Lines Generated Using Split-Intein Mediated Split-Cre Reconstitution. Scientific Reports. Jul. 2012;2:497.
Poreba, et al., Caspase substrates and inhibitors. Cold Spring Harb Perspect Biol. Aug. 1, 2013;5(8):a008680.
Talanian, et al., Substrate specificities of caspase family proteases. J Biol Chem. Apr. 11, 1997;272(15):9677-82.
Pauli, et al., Personalized In Vitro and In Vivo Cancer Models to Guide Precision Medicine. Cancer Discov. May 2017;7(5):462-477.
Clevers, Modeling development and disease with organoids. Cell. Jun. 16, 2016;165(7):1586-1597.
Jenkins, et al., Diversity of cell death pathways: insight from the fly ovary. Trends Cell Biol. Nov. 2013;23(11):567-74.
Drummond-Barbosa, et al., Stem cells and their progeny respond to nutritional changes during *Drosophila* bogenesis. Dev Biol. Mar. 1, 2001;231(1):265-78.
Pritchett, et al., Cracking open cell death in the *Drosophila* ovary. Apoptosis. Aug. 2009;14(8):969-79.
Wong, et al., Dissection of *Drosophila* ovaries. J Vis Exp. Oct. 19, 2006;(1):52.
Gossen, et al., Transcriptional activation by tetracyclines in mammalian cells. Science. Jun. 23, 1995,268 (5218):1766-9.
Inoue, et al., An inducible translocation strategy to rapidly activate and inhibit small GTPase signaling pathways. Nat Methods. Jun. 2005;2(6):415-8.
Yamanashi, et al., The yes-Related Cellular Gene Iyn Encodes a Possible Tyrosine Kinase Similar to p56lck. Mol Cell Biol. Jan. 1987;7(1):237-243.
Fukuda, et al., Cytoplasmic localization of mitogen-activated protein kinase kinase directed by its NH2-terminal, leucine-rich short amino acid sequence, which acts as a nuclear export signal. J Biol Chem. Aug. 16, 1996;271(33):20024-8.
Feil, et al., Regulation of Cre recombinase activity by mutated estrogen receptor ligand-binding domains. Biochem Biophys Res Commun. Aug. 28, 1997;237(3):752-7.
Lazebnik, et al., Cleavage of poly(ADP-ribose) polymerase by a proteinase with properties like ICE. Nature. Sep. 22, 1994;371(6495):346-7.
Li, et al., Caspase-3 activation via mitochondria is required for long-term depression and AMPA receptor internalization. Cell May 28, 2010;141(5):859-71.
Jonas, et al., Proapoptotic N-truncated BCL-xL protein activates endogenous mitochondrial channels in living synaptic terminals. Proc Natl Acad Sci USA. Sep. 14, 2004;101(37):13590-13595.
Neukomm, et al., Diverse cellular and molecular modes of axon degeneration. Trends Cell Biol. Sep. 2014;24 (9):515-23.
Yu, et al., Axon and dendrite pruning in *Drosophila*. Curr Opin Neurobiol. Aug. 2014;27:192-8.
Maor-Nof, et al., Neurite pruning and neuronal cell death: spatial regulation of shared destruction programs. Curr Opin Neurobiol. Dec. 2013;23(6):990-6.
Hyman, et al., Apoptotic and non-apoptotic roles of caspases in neuronal physiology and pathophysiology. Nat Rev Neurosci. May 18, 2012;13(6):395-406.

(56) References Cited

OTHER PUBLICATIONS

Kaiser, et al., RIP3 mediates the embryonic lethality of caspase-8-deficient mice. Nature. Mar. 17, 2011;471 (7338):368-72.
Oberst, et al., Catalytic activity of the caspase-8-FLIP(L) complex inhibits RIPK3-dependent necrosis. Nature. Mar. 17, 2011;471(7338):363-7.
Kaplan, et al., Gradients of a ubiquitin E3 ligase inhibitor and a caspase inhibitor determine differentiation or death in spermatids. Dev Cell. Jul. 20, 2010;19(1):160-73.
Arama, et al., Caspase Activity and a Specific Cytochrome C Are Required for Sperm Differentiation in *Drosophila*. Dev Cell. May 2003;4(5):687-97.
Weaver, et al., CED-3 caspase acts with miRNAs to regulate non-apoptotic gene expression dynamics for robust development in C. elegans. eLife. 2014; 3: e04265.
Tang, et al., In Vivo Biosensor Tracks Non-apoptotic Caspase Activity in *Drosophila*. J Vis Exp. 2016; (117): 53992.
Baum, et al., The *Drosophila* caspases Strica and Drone function redundantly in programmed cell death during bogenesis. Cell Death Differ. Aug. 2007;14(8):1508-17.
Duffy, GAL4 system in *Drosophila*: a fly geneticist's Swiss army knife. Genesis. Sep.-Oct. 2002;34(1-2):1-15.
Fan, et al., The cleaved-Caspase-3 antibody is a marker of Caspase-9-like DRONC activity in *Drosophila*. Cell Death Differ. Mar. 2010;17(3):534-9.
Sun, et al., A molecular signature for anastasis, recovery from the brink of apoptotic cell death. J Cell Biol. Oct. 2, 2017;216(10):3355-3368.
Rennert, et al., Development and validation of a whole exome sequencing test-1 (EXaCT-1) for simultaneous detection of point mutation, indels and copy number alterations for precision cancer care. NPJ Genom Med. 2016;1. pii: 16019.
Beltran, et al., Whole-exome sequencing of metastatic cancer and biomarkers of treatment response. JAMA Oncol. Jul. 2015;1(4):466-74.
Rubin, Health: make precision medicine work for cancer care. Nature. Apr. 16, 2015;520(7547):290-1.
Barretina, et al., The cancer cell line encyclopedia enables predictive modelling of anticancer drug sensitivity. Nature. Mar. 28, 2012;483(7391):603-7.
Shoemaker, The NCI60 human tumour cell line anticancer drug screen. Nat Rev Cancer. Oct. 2006;6(10):813-23.
Iorio, et al., A landscape of pharmacogenomic interactions in cancer. Cell 2016;166:740-54.
Paul, et al., How to improve R&D productivity: the pharmaceutical industry's grand challenge. Nat Rev Drug Discov. Mar. 2010;9(3):203-14.
Li, et al., Genomic changes and gene expression profiles reveal that established glioma cell lines are poorly representative of primary human gliomas. Mol Cancer Res. Jan. 2008;6(1):21-30.
Lawrence, et al., Mutational heterogeneity in cancer and the search for new cancer-associated genes. Nature. Jul. 11, 2013;499(7457):214-218.
Tamborero, et al., Comprehensive identification of mutational cancer driver genes across 12 tumor types. Scientific Reports. Oct. 2013;3:2650.
Zack, et al., Pan-cancer patterns of somatic copy number alteration. Nat Genet. Oct. 2013;45(10):1134-40.
Chapman, et al., Improved survival with vemurafenib in melanoma with BRAF V600E mutation. New England Journal of Medicine. Jun. 2011;364:2507-2516.
Shaw, et al., Crizotinib versus chemotherapy in advanced ALK-positive lung cancer. N Engl J Med. Jun. 20, 2013;368 (25):2385-94.
Arrowsmith, et al., Trial watch: phase II and phase III attrition rates 2011-2012. Nat Rev Drug Discov. Aug. 2013;12(8):569.
Arrowsmith, Trial watch: phase III and submission failures: 2007-2010. Nat Rev Drug Discov. Feb. 2011;10(2):87.
Baker, et al., Modeling pancreatic cancer with organoids. Trends Cancer. Apr. 2016;2(4):176-190.
Boj, et al., Organoid models of human and mouse ductal pancreatic cancer. Cell. Jan. 15, 2015;160(1-2):324-38.
Aitken, et al., Apoptosis in the germ line. Reproduction 141, 139-150. (2011).
Fuchs, et al., Programmed cell death in animal development and disease. Cell. Nov. 11, 2011;147(4):742-58.
Jacobson, et al., Programmed cell death in animal development. Cell. Feb. 7, 1997;88(3):347-54.
Kerr, et al., Apoptosis: a basic biological phenomenon with wide-ranging implications in tissue kinetics. Br J Cancer. Aug. 1972;26(4):239-57.
Hanahan, et al., Hallmarks of cancer: the next generation. Cell. Mar. 4, 2011;144(5):646-74.
Nagata, Apoptosis and autoimmune diseases. Ann N Y Acad Sci. Oct. 2010;1209:10-6.
Mattson, Apoptosis in neurodegenerative disorders. Nat Rev Mol Cell Biol. Nov. 2000;1(2):120-9.
Narula, et al., Apoptosis in myocytes in end-stage heart failure. N Engl J Med. Oct. 17, 1996;335(16):1182-9.
Riedl, et al., Molecular mechanisms of caspase regulation during apoptosis. Nat Rev Mol Cell Biol. Nov. 2004;5(11):897-907.
Green, et al., The central executioners of apoptosis: caspases or mitochondria? Trends Cell Biol. Jul. 1998;8(7):267-71.
Chipuk, et al., The BCL-2 family reunion. Mol Cell. Feb. 12, 2010;37(3):299-310.
Taylor, et al., Apoptosis: controlled demolition at the cellular level. Nat Rev Mol Cell Biol. Mar. 2008,9(3):231-41.
Luthi, et al., The CASBAH: a searchable database of caspase substrates. Cell Death Differ. Apr. 2007;14(4):641-50.
Takemoto, et al., Spatio-temporal activation of caspase revealed by indicator that is insensitive to environmental effects. J Cell Biol. Jan. 20, 2003;160(2):235-43.
Tang, et al., Molecular signature of anastasis for reversal of apoptosis. Version 2. F1000Res. Jan. 13, 2017 [revised Feb. 9, 2017];6:43.
Tang, et al., Strategies for tracking anastasis, a cell survival phenomenon that reverses apoptosis. J Vis Exp. Feb. 16, 2015;(96).
Tang, et al., In vivo CaspaseTracker biosensor system for detecting anastasis and non-apoptotic caspase activity. Sci Rep. 2015; 5: 9015.
Tang, et al., Cell survival, DNA damage, and oncogenic transformation after a transient and reversible apoptotic response. Mol Biol Cell. Jun. 2012;23(12):2240-52.
Tang, et al., Reversibility of apoptosis in cancer cells. Br J Cancer. Jan. 13, 2009;100(1):118-22.
Kenis, et al., Annexin A5 uptake in ischemic myocardium: demonstration of reversible phosphatidylserine externalization and feasibility of radionuclide imaging. J Nucl Med. Feb. 2010;51(2):259-67.
Geske, et al., Early stages of p53-induced apoptosis are reversible. Cell Death Differ. Feb. 2001;8(2):182-91.
Hammill, et al., Annexin V staining due to loss of membrane asymmetry can be reversible and precede commitment to apoptotic death. Exp Cell Res. Aug. 25, 1999;251(1):16-21.
Ichim, et al., Limited mitochondrial permeabilization causes DNA damage and genomic instability in the absence of cell death. Mol Cell. Mar. 5, 2015;57(5):860-872.
Gong, et al., ESCRT-III Acts Downstream of MLKL to Regulate Necroptotic Cell Death and Its Consequences. Cell. Apr. 6, 2017;169(2):286-300.e16.
Drakos, et al., Bridge to recovery: understanding the disconnect between clinical and biological outcomes. Circulation. Jul. 10, 2012;126(2):230-41.
Narula, et al., Mechanisms of disease: apoptosis in heart failure-seeing hope in death. Nat Clin Pract Cardiovasc Med. Dec. 2006;3(12):681-8.
Gordon, et al., DNA damage and repair in light-induced photoreceptor degeneration. Invest Ophthalmol Vis Sci. Nov. 2002;43(11):3511-21.
Milligan, et al., The phosphatidylinositol transfer protein domain of *Drosophila* retinal degeneration B protein is essential for photoreceptor cell survival and recovery from light stimulation. J Cell Biol. Oct. 20, 1997;139(2):351-63.

(56) References Cited

OTHER PUBLICATIONS

McKechnie, et al., Recovery of the rabbit retina after light damage (preliminary observations). Albrecht Von Graefes Arch Klin Exp Ophthalmol. 1980;212(3-4):271-83.

Blennow, et al., Traumatic brain injuries. Nat Rev Dis Primers. Nov. 17, 2016;2:16084.

Loomis, et al., Carcinogenicity of drinking coffee, mate, and very hot beverages. Lancet Oncol. Jul. 2016;17 (7):877-878.

Islami, et al., Tea drinking habits and oesophageal cancer in a high risk area in northern Iran: population based case-control study. BMJ. Mar. 26, 2009;338:b929.

Castellsague, et al., Influence of mate drinking, hot beverages and diet on esophageal cancer risk in South America. Int J Cancer. Nov. 15, 2000;88(4):658-64.

Boffetta, et al., Alcohol and cancer. Lancet Oncol. Feb. 2006;7(2):149-56.

McKillop, et al., Alcohol and liver cancer. Alcohol. Apr. 2005;35(3):195-203.

Wagle, et al., Dissecting therapeutic resistance to RAF inhibition in melanoma by tumor genomic profiling. J Clin Oncol Aug. 1, 2011;29(22):3085-96.

Demedts, et al., Treatment of extensive-stage small cell lung carcinoma: current status and future prospects. Eur Respir J. Jan. 2010;35(1):202-15.

Davis, et al., Repopulation of tumour cells between cycles of chemotherapy: a neglected factor. Lancet Oncol. Oct. 2000;1:86-93.

Chaturvedi, et al., Second cancers among 104,760 survivors of cervical cancer: evaluation of long-term risk. J Natl Cancer Inst. Nov. 7, 2007;99(21):1634-43.

Travis, et al., Second cancers among 40,576 testicular cancer patients: focus on long-term survivors. J Natl Cancer Inst. Sep. 21, 2005;97(18):1354-65.

Smith, et al., Acute myeloid leukemia and myelodysplastic syndrome after doxorubicin-cyclophosphamide adjuvant therapy for operable breast cancer: the National Surgical Adjuvant Breast and Bowel Project Experience. J Clin Oncol. Apr. 1, 2003;21(7):1195-204.

Ding, et al., CasExpress reveals widespread and diverse patterns of cell survival of caspase-3 activation during development in vivo. Elife. Apr. 8, 2016;5. pii: e10936.

Takemoto, et al., Local initiation of caspase activation in *Drosophila* salivary gland programmed cell death in vivo. Proc Natl Acad Sci U S A. Aug. 14, 2007;104(33):13367-72.

Bardet, et al., A fluorescent reporter of caspase activity for live imaging. Proc Natl Acad Sci U S A. Sep. 16, 2008; 105(37): 13901-13905.

Nicholls, et al., Mechanism of a genetically encoded dark-to-bright reporter for caspase activity. J Biol Chem. Jul. 15, 2011;286(28):24977-86.

Golbs, et al., Control of programmed cell death by distinct electrical activity patterns. Cereb Cortex. May 2011;21 (5):1192-202.

Zhang, et al., Visualization of caspase-3-like activity in cells using a genetically encoded fluorescent biosensor activated by protein cleavage. Nat Commun. 2013;4:2157.

To, et al., Rationally designed fluorogenic protease reporter visualizes spatiotemporal dynamics of apoptosis in vivo. Proc Natl Acad Sci USA. Mar. 2015;112(11):3338-3343.

Luan, et al., Refined spatial manipulation of neuronal function by combinatorial restriction of transgene expression. Neuron. Nov. 9, 2006;52(3):425-36.

Wei, et al., Controlling gene expression with the Q repressible binary expression system in Caenorhabditis elegans. Nat Methods. Mar. 11, 2012;9(4):391-5.

Hirrlinger, et al., Split-CreERT2: temporal control of DNA recombination mediated by split-Cre protein fragment complementation. PLoS One. Dec. 16, 2009;4(12):e8354.

Tang, HL., et al., "In vivo CaspaseTracker biosensor system for detecting anastasis and non-apoptotic caspase activity" Sci. Rep. 5, 9015; DOI:10.1038/srep09015 (2015).

Evans, C., et al., "G-TRACE: rapid Gal4-based cell lineage analysis in *Drosophila*" Nat Methods. Aug. 2009 ; 6(8): 603-605. doi:10.1038/nmeth.1356.

Gao, et al., Organoid cultures derived from patients with advanced prostate cancer. Cell. Sep. 25, 2014;159(1):176-187.

Huang, et al., Ductal pancreatic cancer modeling and drug screening using human pluripotent stem cell- and patient-derived tumor organoids. Nat Med. Nov. 2015;21(11):1364-71.

Nash, et al., Development and characterisation of a 3D multicellular in vitro model of normal human breast: a tool for cancer initiation studies. Oncotarget. May 30, 2015;6(15):13731-41.

Baker, et al., Deconstructing the third dimension: how 3D culture microenvironments alter cellular cues. J Cell Sci. Jul. 1, 2012;125(Pt 13):3015-24.

Jamieson, et al., Chemical analysis of multicellular tumour spheroids. Analyst. Jun. 21, 2015;140(12):3910-20.

Pampaloni, et al., The third dimension bridges the gap between cell culture and live tissue. Nat Rev Mol Cell Biol. Oct. 2007;8(10):839-45.

Barbone, et al., Mammalian target of rapamycin contributes to the acquired apoptotic resistance of human mesothelioma multicellular spheroids. J Biol Chem. May 9, 2008;283(19):13021-30.

Frankel, et al., Lack of multicellular drug resistance observed in human ovarian and prostate carcinoma treated with the proteasome inhibitor PS-341. Clin Cancer Res. Sep. 2000;6(9):3719-28.

Mueller-Klieser, Three-dimensional cell cultures: from molecular mechanisms to clinical applications. Am J Physiol. Oct. 1997;273(4 Pt 1):C1109-23.

Mueller-Klieser, Tumor biology and experimental therapeutics. Crit Rev Oncol Hematol. Nov.-Dec. 2000;36(2-3):123-39.

Pickl, et al., Comparison of 3D and 2D tumor models reveals enhanced HER2 activation in 3D associated with an increased response to trastuzumab. Oncogene Jan. 22, 2009;28(3):461-8.

Pauli, et al., An emerging role for cytopathology in precision oncology. Cancer Cytopathol. Mar. 2016;124(3):167-73.

Prandi, et al., Unraveling the clonal hierarchy of somatic genomic aberrations. Genome Biol. Aug. 26, 2014;15(8):439.

Hieronymus, et al., Copy number alteration burden predicts prostate cancer relapse. Proc Natl Acad Sci USA. Jul. 2014;111(30):11139-11144.

Cheng, et al., Molecularly targeted drugs for metastatic colorectal cancer. Drug Des Devel Ther. 2013;7:1315-1322.

Labonte, et al., The dual EGFR/HER2 inhibitor lapatinib synergistically enhances the antitumor activity of the histone deacetylase inhibitor panobinostat in colorectal cancer models. Cancer Res. May 15, 2011;71(10):3635-48.

Cayrefourcq, et al., Establishment and characterization of a cell line from human circulating colon cancer cells. Cancer Res. Mar. 1, 2015;75(5):892-901.

Alix-Panabieres, et al., Clinical applications of circulating tumor cells and circulating tumor DNA as liquid biopsy. Cancer Discov. May 2016;6(5):479-91.

Van De Wetering, et al., Prospective derivation of a living organoid biobank of colorectal cancer patients. Cell. May 7, 2015;161(4):933-45.

Cibulskis, et al., Sensitive detection of somatic point mutations in impure and heterogeneous cancer samples. Nat Biotechnol. Mar. 2013;31(3):213-9.

Jiang, et al., Genome-wide detection of genes targeted by non-Ig somatic hypermutation in lymphoma. PLoS One. 2012;7(7):e40332.

Romanel, et al., ASEQ: fast allele-specific studies from next-generation sequencing data. BMC Med Genomics. Mar. 1, 2015;8:9.

Ramos, et al., Oncotator cancer variant annotation tool. Hum Mutat. Apr. 2015,36(4):E2423-9.

Hadfield, Multi-genome alignment for quality control and contamination screening of next-generation sequencing data. Front Genet. 2014,5:31.

Demichelis, et al., SNP panel identification assay (SPIA): a geneticbased assay for the identification of cell lines. Nucleic Acids Res. Apr. 2008;36(7):2446-2456.

Painter, et al., Transgenerational effects of prenatal exposure to the Dutch famine on neonatal adiposity and health in later life. BJOG. Sep. 2008;115(10):1243-9.

(56) References Cited

OTHER PUBLICATIONS

Yi, et al., Rapid cold-hardening protects *Drosophila* melanogaster from cold-induced apoptosis. Apoptosis. Jul. 2007;12(7):1183-93.
Office Action dated Feb. 10, 2017 in related U.S. Appl. No. 14/383,156.
Response to Office Action dated Feb. 10, 2017 in related U.S. Appl. No. 14/383,156.
Final Office Action dated Oct. 12, 2018 in related U.S. Appl. No. 14/383,156.
Office Action dated Jun. 22, 2016 in related U.S. Appl. No. 14/383,156.
Response to Final Office Action dated Jun. 22, 2016 in related U.S. Appl. No. 14/383,156.
Office Action dated Jan. 30, 2018 in related U.S. Appl. No. 14/383,156.
Response to Office Action dated Jan. 30, 2018 in related U.S. Appl. No. 14/383,156.
Bloom, Induced chromosomal aberrations: biological and clinical significance. J Pediatr 81, 1-8. (1972).
Capy, et al., Stress and transposable elements: co-evolution or useful parasites? Heredity 85, 101-106. (2000).
Chabaud, et al., Apoptosis modulation as a promising target for treatment of systemic sclerosis. Int J Rheumatol 2011, 495792 (2011).
Cifone, et al., Correlation of patterns of anchorage-independent growth with in vivo behavior of cells from a murine fibrosarcoma. Proc Natl Acad Sci USA 77, 1039-1043. (1980).
Coleman, et al., Membrane blebbing during apoptosis results from caspase-mediated activation of Rock I. Nat Cell Biol 3, 339-345. (2001).
Enari, et al., A caspase-activated DNase that degrades DNA during apoptosis, and its inhibitor ICAD. Nature 391, 43-50. (1998).
Fenech, Cytokinesis-block micronucleus cytome assay. Nat Protoc 2, 1084-1104. (2007).
Fischer, et al., Apoptosis-based therapies and drug targets. Cell Death Differ 12 (Suppl 1), 942-961. (2005).
Fu, et al., Balancing repair and tolerance of DNA damage caused by alkylating agents. Nat Rev Cancer 12, 104-120. (2012).
German, Cytological evidence for crossing-over in vitro in human lymphoid cells. Science 144, 298-301. (1964).
Goldin, et al., Apoptotic bodies in a murine model of alcoholic liver disease: reversibility of ethanol-induced changes. J Pathol 171, 73-76. (1993).
Gordon, et al., Causes and consequences of aneuploidy in cancer. Nat Rev Genet 13, 189-203. (2012).
Gordon, et al., DNA damage and repair in light-induced photoreceptor degeneration. Invest Ophthalmol Visual Sci 43, 3511-3521. (2002).
Guicciardi, et al., Apoptosis as a mechanism for liver disease progression. Semin Liver Dis 30, 402-410. (2010).
Hu, et al., Molecular cloning and expression of a functional anti-inflammatory protein, Sj16, of Schistosoma japonicum. Int J Parasitol 39, 191-200. (2009).
Iravanian, et al., Functional reentry in cultured monolayers of neonatal rat cardiac cells. Am J Physiol Heart Circ Physiol 285, H449-H456. (2003).

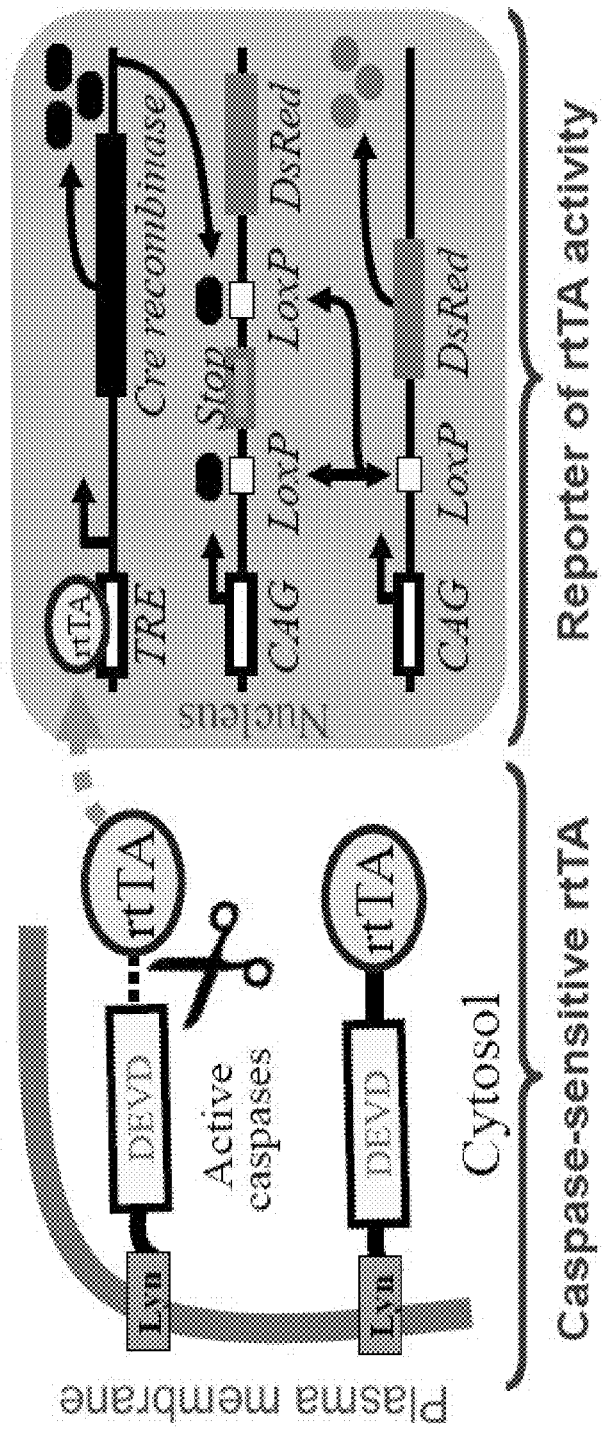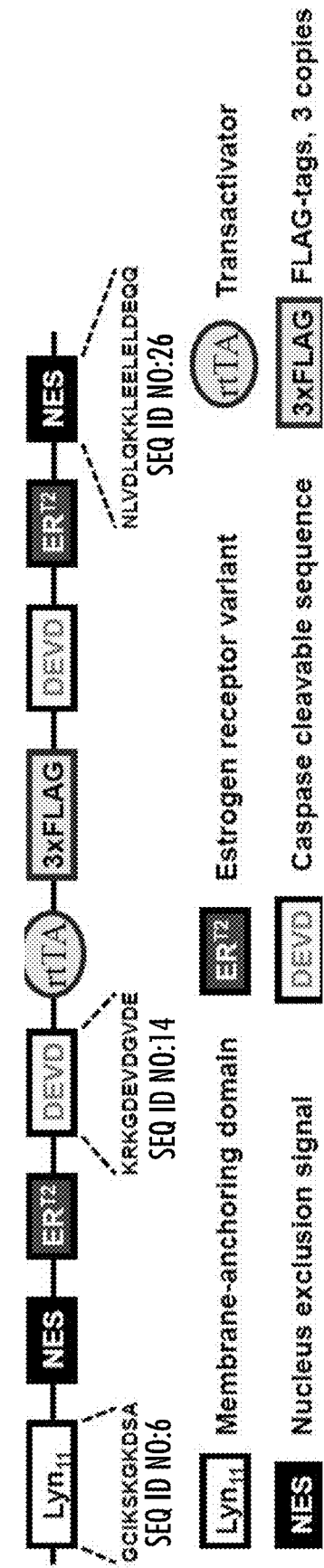
FIG. 2A
FIG. 2B

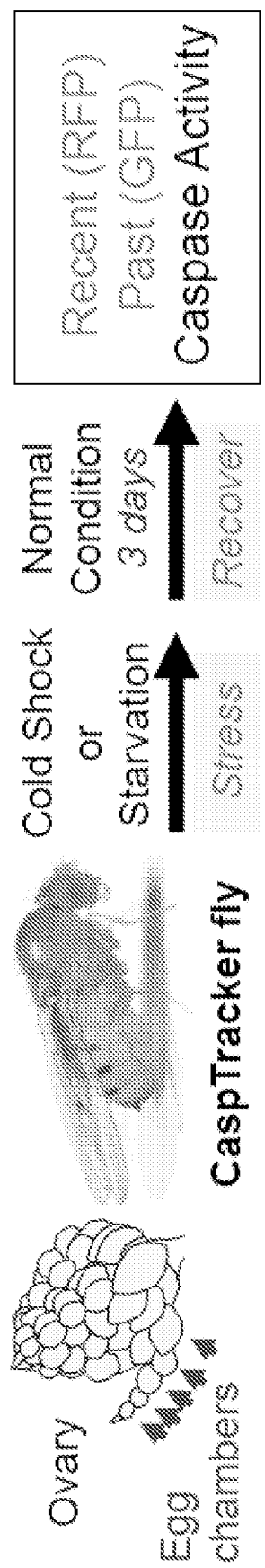
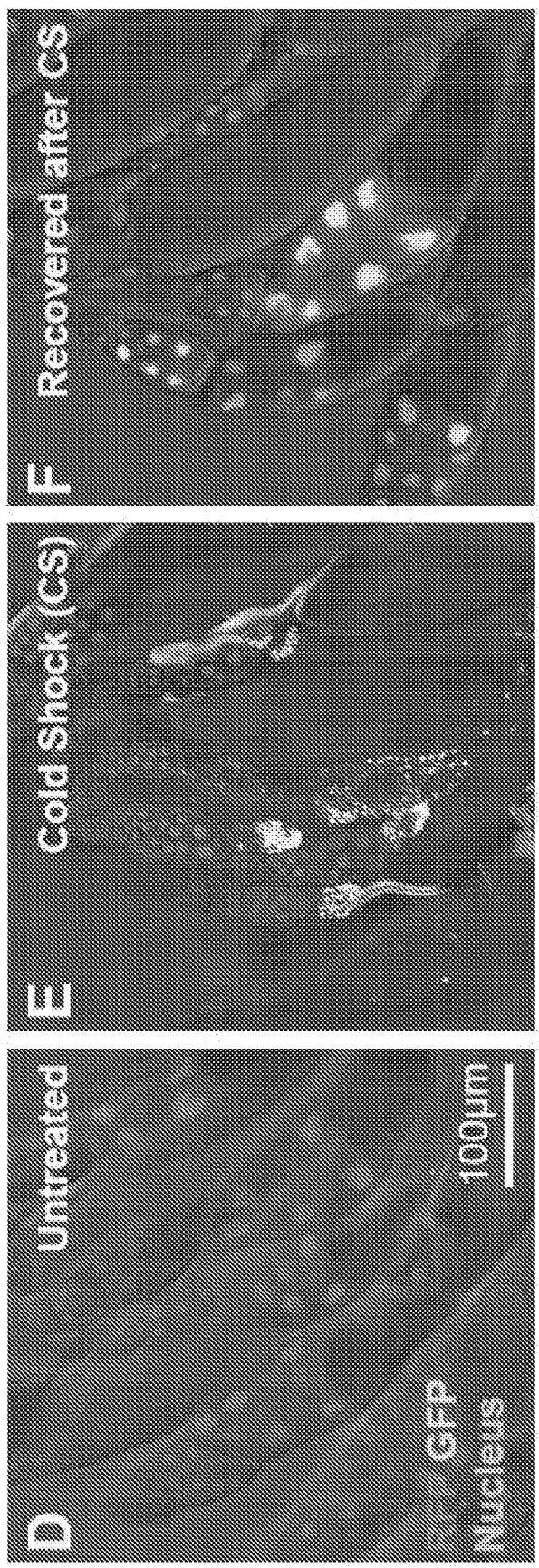
FIG. 3C
FIG. 3D
FIG. 3E
FIG. 3F

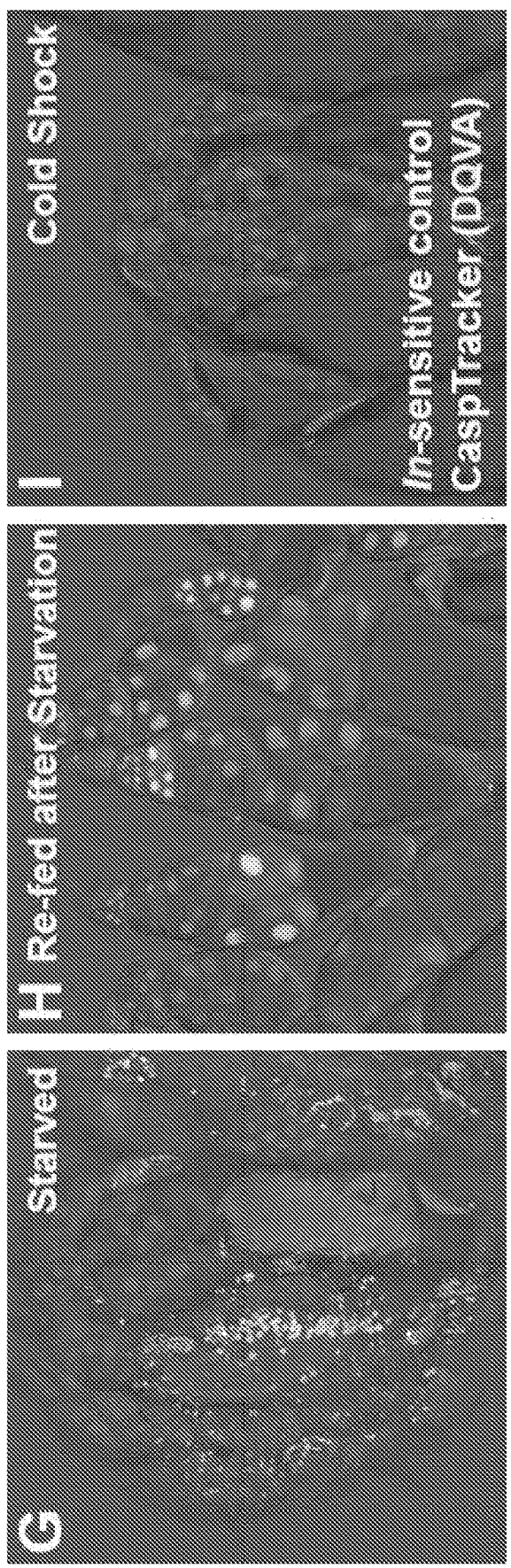

SEQUENCE LISTING

```
<160> NUMBER OF SEQ ID NOS: 47

<210> SEQ ID NO 1
<211> LENGTH: 2937
<212> TYPE: DNA
<213> ORGANISM: Artificial Sequence
<220> FEATURE:
<223> OTHER INFORMATION: Lyn11-NES-ERT2-DEVD-rtTA-3xFLAG-DEVD-ERT2-NES
```

<400> SEQUENCE: 1

```
ggatgtataa aatcaaaagg gaaagacagc gcgggagcag atagtgctgg tagtgctggt    60
aacctggtgg acctccaaaa gaagctggag gagctggagc tggacgagca gcaggctgga   120
gacatgagag ctgccaacct ttggccaagc ccgctcatga tcaaacgctc taagaagaac   180
agcctggcct tgtccctgac ggccgaccag atggtcagtg ccttgttgga tgctgagccc   240
cccatactct attccgagta tgatcctacc agacccttca gtgaagcttc gatgatgggc   300
ttactgacca acctggcaga cagggagctg gttcacatga tcaactgggc gaagagggtg   360
ccaggctttg tggatttgac cctccatgat caggtccacc ttctagaatg tgcctggcta   420
gagatcctga tgattggtct cgtctggcgc tccatggagc acccagtgaa gctactgttt   480
gctcctaact tgctcttgga caggaaccag ggaaaatgtg tagagggcat ggtgagatc    540
ttcgacatgc tgctggctac atcatctcgg ttccgcatga tgaatctgca gggagaggag   600
tttgtgtgcc tcaaatctat tattttgctt aattctggag tgtacacatt tctgtccagc   660
accctgaagt ctctggaaga gaaggaccat atccaccgag tcctggacaa gatcacagac   720
actttgatcc acctgatggc caaggcaggc ctgaccctgc agcagcagca ccagcggctg   780
gcccagctcc tcctcatcct ctcccacatc aggcacatga gtaacaaagg catggagcat   840
ctgtacagca tgaagtgcaa gaacgtggtg cccctctatg acctgctgct ggaggcggcg   900
gacgcccacc gcctacatgc gcccactagc cgtggagggg catccgtgga ggagacggac   960
caaagccact tggccactgc gggctctact tcatcgcatt ccttgcaaaa gtattacatc  1020
acggggagg cagagggttt ccctgccaca gctgtcgaca agaggaaggg cgacgaggtg   1080
gacggcgtgg acgagtctag actgacaag agcaaagtca taaacggcgc tctggaatta  1140
ctcaatggag tcggtatcga aggcctgacg acaaggaaac tcgctcaaaa gctgggagtt  1200
gagcagccta ccctgtactg gcacgtgaag aacaagcggg ccctgctcga tgccctgcca  1260
atcgagatgc tggacaggca tcatacccac ttctgccccc tggaaggcga gtcatggcaa  1320
gactttctgc ggaacaacgc caagtcattc cgctgtgctc tcctctcaca tcgcgacggg  1380
gctaaagtgc atctcggcac ccgcccaaca gagaaacagt acgaaaccct ggaaaatcag  1440
ctcgcgttcc tgtgtcagca aggcttctcc ctggagaacg cactgtacgc tctgtccgcc  1500
gtgggccact ttacactggg ctgcgtattg gaggaacagg agcatcaagt agcaaaagag  1560
gaaagagaga cacctaccac cgattctatg ccccccactt ctgagacaag caattgagctg  1620
ttcgaccgga agggagccga acctgccttc cttttcggcc tggaactaat catatgtggc  1680
ctggagaaac agctaaagtg cgaaagcggc gggccggccg acgcccttga cgattttgac  1740
ttagacatgc tcccagccga tgcccttgac gactttgacc ttgatatgct gcctgctgac  1800
gctcttgacg attttgacct tgacatgctc cccgggact acaaagacca tgacggtgat  1860
tataaagatc atgacatcga ttacaaggat gacgatgacg caaaacgcaa aggtgatgaa  1920
gtagatggag tagacgaagc agggatatg cgcgcagcaa acctctggcc ttcacccctg  1980
atgataaaga ggtcaaagaa aaactctctc gctctgtcac tcaccgcaga tcaaatggtg  2040
tccgcactgc tggacgccga gcctccaata ttgtacagtg aatacgatcc cactcggcct  2100
tttccgagg cctccatgat ggggctcctc acaaatctcg ccgatcgaga acttgtgcat  2160
atgataaatt gggccaaacg agtccctggt ttcgttgatc ttactctgca cgaccaagta  2220
catctgctgg agtgcgcttg gctggaaatt ctcatgatcg ggctggtatg gaggagcatg  2280
```

-continued

```
gaacatcccg tcaaactgct cttcgccccc aacctcttgc tcgaccgaaa tcaggggaag    2340
tgcgtggaag ggatggtaga aatatttgat atgctcctgg ccacaagcag cagattcaga    2400
atgatgaacc tccaaggcga agaattcgtt tgtttgaaga gcatcatcct gctcaacagc    2460
ggcgtctata ccttcctctc ctccacgttg aaaagccttg aggaaaaaga tcacatccat    2520
agggtacttg ataaaattac tgataccctc atacaccdta tggcaaaagc gggactcaca    2580
cttcaacaac aacatcaaag actcgcacaa ttgttgttga ttttgagcca tataaggcat    2640
atgtcaaata agggaatgga acacctctac tctatgaaat gtaagaatgt cgtcccactg    2700
tacgatcttc tccttgaagc tgcagatgct catcggctcc acgcacctac ctctcggggc    2760
ggcgctagcg ttgaagagac tgatcagtca catctcgcga cagctggaag cacaagcagc    2820
cacagcctcc aaaatactat tattacaggc gaggccgaag gcttcccgc tacggccgtg     2880 gataatcttg tagatcttca gaaaaaactc gaagaacttg agcttgatga acaacaa      2937
```

<210> SEQ ID NO 2
<211> LENGTH: 979
<212> TYPE: PRT
<213> ORGANISM: Artificial Sequence
<220> FEATURE:
<223> OTHER INFORMATION: Lyn11-NES-ERT2-DEVD-rtTA-3xFLAG-DEVD-ERT2-NES

<400> SEQUENCE: 2

```
Gly Cys Ile Lys Ser Lys Gly Lys Asp Ser Ala Gly Ala Asp Ser Ala
1               5                   10                  15

Gly Ser Ala Gly Asn Leu Val Asp Leu Gln Lys Lys Leu Glu Glu Leu
            20                  25                  30

Glu Leu Asp Glu Gln Gln Ala Gly Asp Met Arg Ala Ala Asn Leu Trp
        35                  40                  45

Pro Ser Pro Leu Met Ile Lys Arg Ser Lys Asn Ser Leu Ala Leu
    50                  55                  60

Ser Leu Thr Ala Asp Gln Met Val Ser Ala Leu Leu Asp Ala Glu Pro
65                  70                  75                  80

Pro Ile Leu Tyr Ser Glu Tyr Asp Pro Thr Arg Pro Phe Ser Glu Ala
                85                  90                  95

Ser Met Met Gly Leu Leu Thr Asn Leu Ala Asp Arg Glu Leu Val His
            100                 105                 110

Met Ile Asn Trp Ala Lys Arg Val Pro Gly Phe Val Asp Leu Thr Leu
        115                 120                 125

His Asp Gln Val His Leu Leu Glu Cys Ala Trp Leu Glu Ile Leu Met
    130                 135                 140

Ile Gly Leu Val Trp Arg Ser Met Glu His Pro Val Lys Leu Leu Phe
145                 150                 155                 160

Ala Pro Asn Leu Leu Leu Asp Arg Asn Gln Gly Lys Cys Val Glu Gly
                165                 170                 175

Met Val Glu Ile Phe Asp Met Leu Leu Ala Thr Ser Ser Arg Phe Arg
            180                 185                 190

Met Met Asn Leu Gln Gly Glu Glu Phe Val Cys Leu Lys Ser Ile Ile
        195                 200                 205

Leu Leu Asn Ser Gly Val Tyr Thr Phe Leu Ser Ser Thr Leu Lys Ser
    210                 215                 220

Leu Glu Glu Lys Asp His Ile His Arg Val Leu Asp Lys Ile Thr Asp
225                 230                 235                 240

Thr Leu Ile His Leu Met Ala Lys Ala Gly Leu Thr Leu Gln Gln Gln
                245                 250                 255
```

```
His Gln Arg Leu Ala Gln Leu Leu Ile Leu Ser His Ile Arg His
            260                 265                 270

Met Ser Asn Lys Gly Met Glu His Leu Tyr Ser Met Lys Cys Lys Asn
                275                 280                 285

Val Val Pro Leu Tyr Asp Leu Leu Glu Ala Asp Ala His Arg
            290                 295                 300

Leu His Ala Pro Thr Ser Arg Gly Gly Ala Ser Val Glu Glu Thr Asp
305                 310                 315                 320

Gln Ser His Leu Ala Thr Ala Gly Ser Thr Ser Ser His Ser Leu Gln
                325                 330                 335

Lys Tyr Tyr Ile Thr Gly Glu Ala Glu Gly Phe Pro Ala Thr Ala Val
                340                 345                 350

Asp Lys Arg Lys Gly Asp Glu Val Asp Gly Val Asp Glu Ser Arg Leu
            355                 360                 365

Asp Lys Ser Lys Val Ile Asn Gly Ala Leu Glu Leu Leu Asn Gly Val
            370                 375                 380

Gly Ile Glu Gly Leu Thr Thr Arg Lys Leu Ala Gln Lys Leu Gly Val
385                 390                 395                 400

Glu Gln Pro Thr Leu Tyr Trp His Val Lys Asn Lys Arg Ala Leu Leu
                405                 410                 415

Asp Ala Leu Pro Ile Glu Met Leu Asp Arg His His Thr His Phe Cys
            420                 425                 430

Pro Leu Glu Gly Glu Ser Trp Gln Asp Phe Leu Arg Asn Asn Ala Lys
            435                 440                 445

Ser Phe Arg Cys Ala Leu Leu Ser His Arg Asp Gly Ala Lys Val His
            450                 455                 460

Leu Gly Thr Arg Pro Thr Glu Lys Gln Tyr Glu Thr Leu Glu Asn Gln
465                 470                 475                 480

Leu Ala Phe Leu Cys Gln Gln Gly Phe Ser Leu Glu Asn Ala Leu Tyr
                485                 490                 495

Ala Leu Ser Ala Val Gly His Phe Thr Leu Gly Cys Val Leu Glu Glu
            500                 505                 510

Gln Glu His Gln Val Ala Lys Glu Glu Arg Glu Thr Pro Thr Thr Asp
            515                 520                 525

Ser Met Pro Pro Leu Leu Arg Gln Ala Ile Glu Leu Phe Asp Arg Gln
            530                 535                 540

Gly Ala Glu Pro Ala Phe Leu Phe Gly Leu Glu Leu Ile Ile Cys Gly
545                 550                 555                 560

Leu Glu Lys Gln Leu Lys Cys Glu Ser Gly Pro Ala Asp Ala Leu
                565                 570                 575

Asp Asp Phe Asp Leu Asp Met Leu Pro Ala Asp Ala Leu Asp Asp Phe
            580                 585                 590

Asp Leu Asp Met Leu Pro Ala Asp Ala Leu Asp Phe Asp Leu Asp
            595                 600                 605

Met Leu Pro Gly Asp Tyr Lys Asp His Asp Gly Asp Tyr Lys Asp His
            610                 615                 620

Asp Ile Asp Tyr Lys Asp Asp Asp Ala Lys Arg Lys Gly Asp Glu
625                 630                 635                 640

Val Asp Gly Val Asp Glu Ala Gly Asp Met Arg Ala Ala Asn Leu Trp
            645                 650                 655

Pro Ser Pro Leu Met Ile Lys Arg Ser Lys Lys Asn Ser Leu Ala Leu
            660                 665                 670
```

Ser Leu Thr Ala Asp Gln Met Val Ser Ala Leu Leu Asp Ala Glu Pro
            675                 680                 685

Pro Ile Leu Tyr Ser Glu Tyr Asp Pro Thr Arg Pro Phe Ser Glu Ala
        690                 695                 700

Ser Met Met Gly Leu Leu Thr Asn Leu Ala Asp Arg Glu Leu Val His
705                 710                 715                 720

Met Ile Asn Trp Ala Lys Arg Val Pro Gly Phe Val Asp Leu Thr Leu
                725                 730                 735

His Asp Gln Val His Leu Leu Glu Cys Ala Trp Leu Glu Ile Leu Met
            740                 745                 750

Ile Gly Leu Val Trp Arg Ser Met Glu His Pro Val Lys Leu Leu Phe
        755                 760                 765

Ala Pro Asn Leu Leu Leu Asp Arg Asn Gln Gly Lys Cys Val Glu Gly
770                 775                 780

Met Val Glu Ile Phe Asp Met Leu Leu Ala Thr Ser Ser Arg Phe Arg
785                 790                 795                 800

Met Met Asn Leu Gln Gly Glu Glu Phe Val Cys Leu Lys Ser Ile Ile
                805                 810                 815

Leu Leu Asn Ser Gly Val Tyr Thr Phe Leu Ser Ser Thr Leu Lys Ser
            820                 825                 830

Leu Glu Glu Lys Asp His Ile His Arg Val Leu Asp Lys Ile Thr Asp
        835                 840                 845

Thr Leu Ile His Leu Met Ala Lys Ala Gly Leu Thr Leu Gln Gln Gln
850                 855                 860

His Gln Arg Leu Ala Gln Leu Leu Leu Ile Leu Ser His Ile Arg His
865                 870                 875                 880

Met Ser Asn Lys Gly Met Glu His Leu Tyr Ser Met Lys Cys Lys Asn
                885                 890                 895

Val Val Pro Leu Tyr Asp Leu Leu Leu Glu Ala Ala Asp Ala His Arg
            900                 905                 910

Leu His Ala Pro Thr Ser Arg Gly Gly Ala Ser Val Glu Glu Thr Asp
        915                 920                 925

Gln Ser His Leu Ala Thr Ala Gly Ser Thr Ser Ser His Ser Leu Gln
930                 935                 940

Lys Tyr Tyr Ile Thr Gly Glu Ala Glu Gly Phe Pro Ala Thr Ala Val
945                 950                 955                 960

Asp Asn Leu Val Asp Leu Gln Lys Lys Leu Glu Leu Glu Leu Leu Asp
                965                 970                 975

Glu Gln Gln

<210> SEQ ID NO 3
<211> LENGTH: 2934
<212> TYPE: DNA
<213> ORGANISM: Artificial Sequence
<220> FEATURE:
<223> OTHER INFORMATION: Lyn11-Nes-ERT2-DEVD-rtTA-3xFLAG-DEVD-ERT2-Nes
      minus the gca codon at end of 3x flag

<400> SEQUENCE: 3
ggatgtataa aatcaaaagg gaaagacagc gcgggagcag atagtgctgg tagtgctggt      60
aacctggtgg acctccaaaa gaagctggag gagctggagc tggacgagca gcaggctgga     120
gacatgagag ctgccaacct tggccaagc ccgctcatga tcaaacgctc taagaagaac      180
agcctggcct gtcccctgac ggccgaccag atggtcagtg ccttgttgga tgctgagccc     240
cccatactct attccgagta tgatcctacc agacccttca gtgaagcttc gatgatgggc     300

```
ttactgacca acctggcaga cagggagctg gttcacatga tcaactgggc gaagagggtg      360
ccaggctttg tggatttgac cctccatgat caggtccacc ttctagaatg tgcctggcta      420
gagatcctga tgattggtct cgtctggcgc tccatggagc acccagtgaa gctactgttt      480
gctcctaact tgctcttgga caggaaccag ggaaaatgtg tagagggcat ggtggagatc      540
ttcgacatgc tgctggctac atcatctcgg ttccgcatga tgaatctgca gggagaggag      600
tttgtgtgcc tcaaatctat tattttgctt aattctggag tgtacacatt tctgtccagc      660
accctgaagt ctctggaaga aaggaccat atccaccgag tcctggacaa gatcacagac      720
actttgatcc acctgatggc caaggcaggc ctgaccctgc agcagcagca ccagcggctg      780
gcccagctcc tcctcatcct ctcccacatc aggcacatga gtaacaaagg catggagcat      840
ctgtacagca tgaagtgcaa gaacgtggtg cccctctatg acctgctgct ggaggcggcg      900
gacgcccacc gcctacatgc gcccactagc cgtggagggg catccgtgga ggagacggac      960
caaagccact tggccactgc gggctctact tcatcgcatt ccttgcaaaa gtattacatc     1020
acgggggagg cagagggttt ccctgccaca gctgtcgaca agaggaaggg cgacgaggtg     1080
gacggcgtgg acgagtctag actggacaag agcaaagtca taaacggcgc tctggaatta     1140
ctcaatggag tcggtatcga aggcctgacg acaaggaaac tcgctcaaaa gctgggagtt     1200
gagcagccta ccctgtactg gcacgtgaag aacaagcggg ccctgctcga tgccctgcca     1260
atcgagatgc tggacaggca tcatacccac ttctgccccc tggaaggcga gtcatggcaa     1320
gactttctgc ggaacaacgc caagtcattc cgctgtgctc tcctctcaca tcgcgacggg     1380
gctaaagtgc atctcggcac ccgcccaaca gagaaacagt acgaaaccct ggaaaatcag     1440
ctcgcgttcc tgtgtcagca aggcttctcc ctggagaacg cactgtacgc tctgtccgcc     1500
gtgggccact ttacactggg ctgcgtattg gaggaacagg agcatcaagt agcaaaagag     1560
gaaagagaga cacctaccac cgattctatg cccccacttc tgagacaagc aattgagctg     1620
ttcgaccggc agggagccga acctgccttc cttttcggcc tggaactaat catatgtggc     1680
ctggagaaac agctaaagtg cgaaagcggc gggccggccg acgcccttga cgattttgac     1740
ttagacatgc tcccagccga tgcccttgac gactttgacc ttgatatgct gcctgctgac     1800
gctcttgacg attttgacct tgacatgctc cccggggact acaaagacca tgacggtgat     1860
tataaagatc atgacatcga ttacaaggat gacgatgaca acgcaaagg tgatgaagta     1920 gatggagtag acgaagcagg ggatatgcgc gcagcaaacc tctggccttc accctgatg      1980 ataaagaggt caaagaaaaa ctctctcgct ctgtcactca ccgcagatca aatggtgtcc     2040
gcactgctgg acgccgagcc tccaatattg tacagtgaat acgatccac tcggccttt      2100 tccgaggcct ccatgatggg gctcctcaca aatctcgccg atcgagaact tgtgcatatg     2160
ataaattggg ccaaacgagt ccctggtttc gttgatctta ctctgcacga ccaagtacat     2220
ctgctggagt gcgcttggct ggaaattctc atgatcgggc tggtatggag gagcatggaa     2280
catcccgtca aactgctctt cgcccccaac ctcttgctcg accgaaatca ggggaagtgc     2340
gtggaaggga tggtagaaat atttgatatg ctcctggcca caagcagcag attcagaatg     2400
atgaacctcc aaggcgaaga attcgtttgt ttgaagagca tcatcctgct caacagcggc     2460 gtctataccct tcctctcctc cacgttgaaa agccttgagg aaaagatca catccatagg     2520 gtacttgata aaattactga taccctcata caccttatgg caaagcggg actcacactt     2580 caacaacaac atcaaagact cgcacaattg ttgttgattt tgagccatat aaggcatatg     2640
```

-continued

```
tcaaataagg gaatggaaca cctctactct atgaaatgta agaatgtcgt cccactgtac    2700
gatcttctcc ttgaagctgc agatgctcat cggctccacg cacctacctc tcggggcggc    2760
gctagcgttg aagagactga tcagtcacat ctcgcgacag ctggaagcac aagcagccac    2820
agcctccaaa aatactatat tacaggcgag gccgaaggct tccccgctac ggccgtggat    2880
aatcttgtag atcttcagaa aaaactcgaa gaacttgagc ttgatgaaca acaa          2934
```

<210> SEQ ID NO 4
<211> LENGTH: 978
<212> TYPE: PRT
<213> ORGANISM: Artificial Sequence
<220> FEATURE:
<223> OTHER INFORMATION: Lyn11-Nes-ERT2-DEVD-rtTA-3xFLAG-DEVD-ERT2-Nes
      minues the gca codon at end of 3x flag

<400> SEQUENCE: 4

```
Gly Cys Ile Lys Ser Lys Gly Lys Asp Ser Ala Gly Ala Asp Ser Ala
1               5                   10                  15

Gly Ser Ala Gly Asn Leu Val Asp Leu Gln Lys Lys Leu Glu Glu Leu
            20                  25                  30

Glu Leu Asp Glu Gln Gln Ala Gly Asp Met Arg Ala Ala Asn Leu Trp
        35                  40                  45

Pro Ser Pro Leu Met Ile Lys Arg Ser Lys Lys Asn Ser Leu Ala Leu
    50                  55                  60

Ser Leu Thr Ala Asp Gln Met Val Ser Ala Leu Leu Asp Ala Glu Pro
65                  70                  75                  80

Pro Ile Leu Tyr Ser Glu Tyr Asp Pro Thr Arg Pro Phe Ser Glu Ala
                85                  90                  95

Ser Met Met Gly Leu Leu Thr Asn Leu Ala Asp Arg Glu Leu Val His
            100                 105                 110

Met Ile Asn Trp Ala Lys Arg Val Pro Gly Phe Val Asp Leu Thr Leu
        115                 120                 125

His Asp Gln Val His Leu Leu Glu Cys Ala Trp Leu Glu Ile Leu Met
    130                 135                 140

Ile Gly Leu Val Trp Arg Ser Met Glu His Pro Val Lys Leu Leu Phe
145                 150                 155                 160

Ala Pro Asn Leu Leu Leu Asp Arg Asn Gln Gly Lys Cys Val Glu Gly
                165                 170                 175

Met Val Glu Ile Phe Asp Met Leu Leu Ala Thr Ser Ser Arg Phe Arg
            180                 185                 190

Met Met Asn Leu Gln Gly Glu Glu Phe Val Cys Leu Lys Ser Ile Ile
        195                 200                 205

Leu Leu Asn Ser Gly Val Tyr Thr Phe Leu Ser Ser Thr Leu Lys Ser
    210                 215                 220

Leu Glu Glu Lys Asp His Ile His Arg Val Leu Asp Lys Ile Thr Asp
225                 230                 235                 240

Thr Leu Ile His Leu Met Ala Lys Ala Gly Leu Thr Leu Gln Gln Gln
                245                 250                 255

His Gln Arg Leu Ala Gln Leu Leu Leu Ile Leu Ser His Ile Arg His
            260                 265                 270

Met Ser Asn Lys Gly Met Glu His Leu Tyr Ser Met Lys Cys Lys Asn
        275                 280                 285

Val Val Pro Leu Tyr Asp Leu Leu Leu Glu Ala Ala Asp Ala His Arg
    290                 295                 300
```

```
Leu His Ala Pro Thr Ser Arg Gly Gly Ala Ser Val Glu Glu Thr Asp
305                 310                 315                 320

Gln Ser His Leu Ala Thr Ala Gly Ser Thr Ser Ser His Ser Leu Gln
            325                 330                 335

Lys Tyr Tyr Ile Thr Gly Glu Ala Glu Gly Phe Pro Ala Thr Ala Val
                340                 345                 350

Asp Lys Arg Lys Gly Asp Glu Val Asp Gly Val Asp Glu Ser Arg Leu
            355                 360                 365

Asp Lys Ser Lys Val Ile Asn Gly Ala Leu Glu Leu Leu Asn Gly Val
            370                 375                 380

Gly Ile Glu Gly Leu Thr Thr Arg Lys Leu Ala Gln Lys Leu Gly Val
385                 390                 395                 400

Glu Gln Pro Thr Leu Tyr Trp His Val Lys Asn Lys Arg Ala Leu Leu
                405                 410                 415

Asp Ala Leu Pro Ile Glu Met Leu Asp Arg His His Thr His Phe Cys
            420                 425                 430

Pro Leu Glu Gly Glu Ser Trp Gln Asp Phe Leu Arg Asn Asn Ala Lys
            435                 440                 445

Ser Phe Arg Cys Ala Leu Leu Ser His Arg Asp Gly Ala Lys Val His
            450                 455                 460

Leu Gly Thr Arg Pro Thr Glu Lys Gln Tyr Glu Thr Leu Glu Asn Gln
465                 470                 475                 480

Leu Ala Phe Leu Cys Gln Gln Gly Phe Ser Leu Glu Asn Ala Leu Tyr
                485                 490                 495

Ala Leu Ser Ala Val Gly His Phe Thr Leu Gly Cys Val Leu Glu Glu
            500                 505                 510

Gln Glu His Gln Val Ala Lys Glu Arg Glu Thr Pro Thr Thr Asp
            515                 520                 525

Ser Met Pro Pro Leu Leu Arg Gln Ala Ile Glu Leu Phe Asp Arg Gln
            530                 535                 540

Gly Ala Glu Pro Ala Phe Leu Phe Gly Leu Glu Leu Ile Ile Cys Gly
545                 550                 555                 560

Leu Glu Lys Gln Leu Lys Cys Glu Ser Gly Gly Pro Ala Asp Ala Leu
                565                 570                 575

Asp Asp Phe Asp Leu Asp Met Leu Pro Ala Asp Ala Leu Asp Asp Phe
            580                 585                 590

Asp Leu Asp Met Leu Pro Ala Asp Ala Leu Asp Phe Asp Leu Asp
            595                 600                 605

Met Leu Pro Gly Asp Tyr Lys Asp His Asp Gly Asp Tyr Lys Asp His
            610                 615                 620

Asp Ile Asp Tyr Lys Asp Asp Asp Lys Arg Lys Gly Asp Glu Val
625                 630                 635                 640

Asp Gly Val Asp Glu Ala Gly Asp Met Arg Ala Ala Asn Leu Trp Pro
            645                 650                 655

Ser Pro Leu Met Ile Lys Arg Ser Lys Lys Asn Ser Leu Ala Leu Ser
            660                 665                 670

Leu Thr Ala Asp Gln Met Val Ser Ala Leu Leu Asp Ala Glu Pro Pro
            675                 680                 685

Ile Leu Tyr Ser Glu Tyr Asp Pro Thr Arg Pro Phe Ser Glu Ala Ser
            690                 695                 700

Met Met Gly Leu Leu Thr Asn Leu Ala Asp Arg Glu Leu Val His Met
705                 710                 715                 720
```

-continued

Ile Asn Trp Ala Lys Arg Val Pro Gly Phe Val Asp Leu Thr Leu His
                725                 730                 735

Asp Gln Val His Leu Leu Glu Cys Ala Trp Leu Glu Ile Leu Met Ile
            740                 745                 750

Gly Leu Val Trp Arg Ser Met Glu His Pro Val Lys Leu Leu Phe Ala
        755                 760                 765

Pro Asn Leu Leu Leu Asp Arg Asn Gln Gly Lys Cys Val Glu Gly Met
    770                 775                 780

Val Glu Ile Phe Asp Met Leu Leu Ala Thr Ser Ser Arg Phe Arg Met
785                 790                 795                 800

Met Asn Leu Gln Gly Glu Glu Phe Val Cys Leu Lys Ser Ile Ile Leu
                805                 810                 815

Leu Asn Ser Gly Val Tyr Thr Phe Leu Ser Ser Thr Leu Lys Ser Leu
            820                 825                 830

Glu Glu Lys Asp His Ile His Arg Val Leu Asp Lys Ile Thr Asp Thr
        835                 840                 845

Leu Ile His Leu Met Ala Lys Ala Gly Leu Thr Leu Gln Gln Gln His
    850                 855                 860

Gln Arg Leu Ala Gln Leu Leu Leu Ile Leu Ser His Ile Arg His Met
865                 870                 875                 880

Ser Asn Lys Gly Met Glu His Leu Tyr Ser Met Lys Cys Lys Asn Val
                885                 890                 895

Val Pro Leu Tyr Asp Leu Leu Leu Glu Ala Ala Asp Ala His Arg Leu
            900                 905                 910

His Ala Pro Thr Ser Arg Gly Gly Ala Ser Val Glu Glu Thr Asp Gln
        915                 920                 925

Ser His Leu Ala Thr Ala Gly Ser Thr Ser Ser His Ser Leu Gln Lys
    930                 935                 940

Tyr Tyr Ile Thr Gly Glu Ala Glu Gly Phe Pro Ala Thr Ala Val Asp
945                 950                 955                 960

Asn Leu Val Asp Leu Gln Lys Lys Leu Glu Glu Leu Glu Leu Asp Glu
                965                 970                 975

Gln Gln

<210> SEQ ID NO 5
<211> LENGTH: 33
<212> TYPE: DNA
<213> ORGANISM: Artificial Sequence
<220> FEATURE:
<223> OTHER INFORMATION: Lyn11

<400> SEQUENCE: 5
ggatgtataa aatcaaaagg gaaagacagc gcg                                33

<210> SEQ ID NO 6
<211> LENGTH: 11
<212> TYPE: PRT
<213> ORGANISM: Artificial Sequence
<220> FEATURE:
<223> OTHER INFORMATION: Lyn11

<400> SEQUENCE: 6

Gly Cys Ile Lys Ser Lys Gly Lys Asp Ser Ala
1               5                   10

<210> SEQ ID NO 7
<211> LENGTH: 24
<212> TYPE: DNA

```
<213> ORGANISM: Artificial Sequence
<220> FEATURE:
<223> OTHER INFORMATION: Flexible linker

<400> SEQUENCE: 7
ggagcagata gtgctggtag tgct                                         24

<210> SEQ ID NO 8
<211> LENGTH: 8
<212> TYPE: PRT
<213> ORGANISM: Artificial Sequence
<220> FEATURE:
<223> OTHER INFORMATION: Flexible linker

<400> SEQUENCE: 8

Gly Ala Asp Ser Ala Gly Ser Ala
1               5

<210> SEQ ID NO 9
<211> LENGTH: 54
<212> TYPE: DNA
<213> ORGANISM: Artificial Sequence
<220> FEATURE:
<223> OTHER INFORMATION: Nuclear exclusion signal (NES)

<400> SEQUENCE: 9
aacctggtgg acctccaaaa gaagctggag gagctggagc tggacgagca gcag        54

<210> SEQ ID NO 10
<211> LENGTH: 18
<212> TYPE: PRT
<213> ORGANISM: Artificial Sequence
<220> FEATURE:
<223> OTHER INFORMATION: NES

<400> SEQUENCE: 10

Asn Leu Val Asp Leu Gln Lys Lys Leu Glu Glu Leu Glu Leu Asp Glu
1               5                   10                  15

Gln Gln

<210> SEQ ID NO 11
<211> LENGTH: 945
<212> TYPE: DNA
<213> ORGANISM: Artificial Sequence
<220> FEATURE:
<223> OTHER INFORMATION: ERT2

<400> SEQUENCE: 11
gctggagaca tgagagctgc caaccttttgg ccaagcccgc tcatgatcaa acgctctaag    60
aagaacagcc tggccttgtc cctgacggcc gaccagatgg tcagtgcctt gttggatgct   120 gagccccca tactctattc cgagtatgat cctaccagac ccttcagtga agcttcgatg    180
atgggcttac tgaccaacct ggcagacagg gagctggttc acatgatcaa ctgggcgaag   240
agggtgccag gctttgtgga tttgaccctc catgatcagg tccaccttct agaatgtgcc   300
tggctagaga tcctgatgat tggtctcgtc tggcgctcca tggagcaccc agtgaagcta   360
ctgtttgctc ctaacttgct cttggacagg aaccagggaa atgtgtagag ggcatggtg    420 gagatcttcg acatgctgct ggctacatca tctcggttcc gcatgatgaa tctgcaggga   480
gaggagtttg tgtgcctcaa atctattatt ttgcttaatt ctggagtgta cacatttctg   540
tccagcaccc tgaagtctct ggaagagaag accatatccc accgagtcct ggacaagatc   600
acagacactt tgatccacct gatggccaag gcaggcctga ccctgcagca gcagcaccag   660
```

```
cggctggccc agctcctcct catcctctcc cacatcaggc acatgagtaa caaaggcatg      720
gagcatctgt acagcatgaa gtgcaagaac gtggtgcccc tctatgacct gctgctggag      780
gcggcggacg cccaccgcct acatgcgccc actagccgtg agggggcatc cgtggaggag      840
acggaccaaa gccacttggc cactgcgggc tctacttcat cgcattcctt gcaaaagtat      900
tacatcacgg gggaggcaga gggtttccct gccacagctg tcgac                     945
```

```
<210> SEQ ID NO 12
<211> LENGTH: 315
<212> TYPE: PRT
<213> ORGANISM: Artificial Sequence
<220> FEATURE:
<223> OTHER INFORMATION: ERT2

<400> SEQUENCE: 12

Ala Gly Asp Met Arg Ala Ala Asn Leu Trp Pro Ser Pro Leu Met Ile
1               5                   10                  15

Lys Arg Ser Lys Lys Asn Ser Leu Ala Leu Ser Leu Thr Ala Asp Gln
            20                  25                  30

Met Val Ser Ala Leu Leu Asp Ala Glu Pro Pro Ile Leu Tyr Ser Glu
        35                  40                  45

Tyr Asp Pro Thr Arg Pro Phe Ser Glu Ala Ser Met Met Gly Leu Leu
    50                  55                  60

Thr Asn Leu Ala Asp Arg Glu Leu Val His Met Ile Asn Trp Ala Lys
65                  70                  75                  80

Arg Val Pro Gly Phe Val Asp Leu Thr Leu His Asp Gln Val His Leu
                85                  90                  95

Leu Glu Cys Ala Trp Leu Glu Ile Leu Met Ile Gly Leu Val Trp Arg
            100                 105                 110

Ser Met Glu His Pro Val Lys Leu Leu Phe Ala Pro Asn Leu Leu Leu
        115                 120                 125

Asp Arg Asn Gln Gly Lys Cys Val Glu Gly Met Val Glu Ile Phe Asp
    130                 135                 140

Met Leu Leu Ala Thr Ser Ser Arg Phe Arg Met Met Asn Leu Gln Gly
145                 150                 155                 160

Glu Glu Phe Val Cys Leu Lys Ser Ile Ile Leu Leu Asn Ser Gly Val
                165                 170                 175

Tyr Thr Phe Leu Ser Ser Thr Leu Lys Ser Leu Glu Glu Lys Asp His
            180                 185                 190

Ile His Arg Val Leu Asp Lys Ile Thr Asp Thr Leu Ile His Leu Met
        195                 200                 205

Ala Lys Ala Gly Leu Thr Leu Gln Gln Gln His Gln Arg Leu Ala Gln
    210                 215                 220

Leu Leu Leu Ile Leu Ser His Ile Arg His Met Ser Asn Lys Gly Met
225                 230                 235                 240

Glu His Leu Tyr Ser Met Lys Cys Lys Asn Val Val Pro Leu Tyr Asp
                245                 250                 255

Leu Leu Leu Glu Ala Ala Asp Ala His Arg Leu His Ala Pro Thr Ser
            260                 265                 270

Arg Gly Gly Ala Ser Val Glu Glu Thr Asp Gln Ser His Leu Ala Thr
        275                 280                 285

Ala Gly Ser Thr Ser Ser His Ser Leu Gln Lys Tyr Tyr Ile Thr Gly
    290                 295                 300
```

Glu Ala Glu Gly Phe Pro Ala Thr Ala Val Asp
305                 310                 315

<210> SEQ ID NO 13
<211> LENGTH: 36
<212> TYPE: DNA
<213> ORGANISM: Artificial Sequence
<220> FEATURE:
<223> OTHER INFORMATION: DEVD (PARP)

<400> SEQUENCE: 13
aagaggaagg gcgacgaggt ggacggcgtg gacgag                                    36

<210> SEQ ID NO 14
<211> LENGTH: 12
<212> TYPE: PRT
<213> ORGANISM: Artificial Sequence
<220> FEATURE:
<223> OTHER INFORMATION: DEVD (PARP)

<400> SEQUENCE: 14

Lys Arg Lys Gly Asp Glu Val Asp Gly Val Asp Glu
1               5                   10

<210> SEQ ID NO 15
<211> LENGTH: 12
<212> TYPE: DNA
<213> ORGANISM: Artificial Sequence
<220> FEATURE:
<223> OTHER INFORMATION: DEVD nt

<400> SEQUENCE: 15
gacgaggtgg ac                                                              12

<210> SEQ ID NO 16
<211> LENGTH: 4
<212> TYPE: PRT
<213> ORGANISM: Artificial Sequence
<220> FEATURE:
<223> OTHER INFORMATION: DEVD AA

<400> SEQUENCE: 16

Asp Glu Val Asp
1

<210> SEQ ID NO 17
<211> LENGTH: 741
<212> TYPE: DNA
<213> ORGANISM: Artificial Sequence
<220> FEATURE:
<223> OTHER INFORMATION: reverse tetracycline transactivator

<400> SEQUENCE: 17
tctagactgg acaagagcaa agtcataaac ggcgctctgg aattactcaa tggagtcggt          60
atcgaaggcc tgacgacaag gaaactcgct caaaagctgg gagttgagca gcctaccctg        120
tactggcacg tgaagaacaa gcgggccctg ctcgatgccc tgccaatcga gatgctggac        180
aggcatcata cccacttctg cccccctgga aggcgagtca tggcaagact tctgcggaac        240
aacgccaagt cattccgctg tgctctcctc tcacatcgcg acgggctaa agtgcatctc        300 ggcacccgcc caacagagaa acagtacgaa accctggaaa atcagctcgc gttcctgtgt        360
cagcaaggct ctcccctgga gaacgcactg tacgctctgt ccgccgtggg ccactttaca        420
ctgggctgcg tattggagga acaggagcat caagtagcaa agaggaaag agagacacct        480

```
accaccgatt ctatgccccc acttctgaga caagcaattg agctgttcga ccggcaggga    540
gccgaacctg ccttccttt cggcctggaa ctaatcatat gtggcctgga gaaacagcta    600
aagtgcgaaa gcggcgggcc ggccgacgcc cttgacgatt ttgacttaga catgctccca    660
gccgatgccc ttgacgactt tgaccttgat atgctgcctg ctgacgctct tgacgatttt    720
gaccttgaca tgctccccgg g                                              741
```

<210> SEQ ID NO 18
<211> LENGTH: 247
<212> TYPE: PRT
<213> ORGANISM: Artificial Sequence
<220> FEATURE:
<223> OTHER INFORMATION: reverse tetracycline transactivator

<400> SEQUENCE: 18

```
Ser Arg Leu Asp Lys Ser Lys Val Ile Asn Gly Ala Leu Glu Leu Leu
1               5                   10                  15

Asn Gly Val Gly Ile Glu Gly Leu Thr Thr Arg Lys Leu Ala Gln Lys
            20                  25                  30

Leu Gly Val Glu Gln Pro Thr Leu Tyr Trp His Val Lys Asn Lys Arg
        35                  40                  45

Ala Leu Leu Asp Ala Leu Pro Ile Glu Met Leu Asp Arg His His Thr
    50                  55                  60

His Phe Cys Pro Leu Glu Gly Glu Ser Trp Gln Asp Phe Leu Arg Asn
65                  70                  75                  80

Asn Ala Lys Ser Phe Arg Cys Ala Leu Leu Ser His Arg Asp Gly Ala
                85                  90                  95

Lys Val His Leu Gly Thr Arg Pro Thr Glu Lys Gln Tyr Glu Thr Leu
            100                 105                 110

Glu Asn Gln Leu Ala Phe Leu Cys Gln Gln Gly Phe Ser Leu Glu Asn
        115                 120                 125

Ala Leu Tyr Ala Leu Ser Ala Val Gly His Phe Thr Leu Gly Cys Val
    130                 135                 140

Leu Glu Glu Gln Glu His Gln Val Ala Lys Glu Arg Glu Thr Pro
145                 150                 155                 160

Thr Thr Asp Ser Met Pro Pro Leu Leu Arg Gln Ala Ile Glu Leu Phe
                165                 170                 175

Asp Arg Gln Gly Ala Glu Pro Ala Phe Leu Phe Gly Leu Glu Leu Ile
            180                 185                 190

Ile Cys Gly Leu Glu Lys Gln Leu Lys Cys Glu Ser Gly Gly Pro Ala
        195                 200                 205

Asp Ala Leu Asp Asp Phe Asp Leu Asp Met Leu Pro Ala Asp Ala Leu
    210                 215                 220

Asp Asp Phe Asp Leu Asp Met Leu Pro Ala Asp Ala Leu Asp Asp Phe
225                 230                 235                 240

Asp Leu Asp Met Leu Pro Gly
                245
```

<210> SEQ ID NO 19
<211> LENGTH: 63
<212> TYPE: DNA
<213> ORGANISM: Artificial Sequence
<220> FEATURE:
<223> OTHER INFORMATION: 3x Flag

<400> SEQUENCE: 19

```
gactacaaag accatgacgg tgattataaa gatcatgaca tcgattacaa ggatgacgat    60
gac                                                                 63
```

<210> SEQ ID NO 20
<211> LENGTH: 21
<212> TYPE: PRT
<213> ORGANISM: Artificial Sequence
<220> FEATURE:
<223> OTHER INFORMATION: 3X Flag

<400> SEQUENCE: 20

```
Asp Tyr Lys Asp His Asp Gly Asp Tyr Lys Asp His Asp Ile Asp Tyr
1               5                   10                  15

Lys Asp Asp Asp Asp
            20
```

<210> SEQ ID NO 21
<211> LENGTH: 36
<212> TYPE: DNA
<213> ORGANISM: Artificial Sequence
<220> FEATURE:
<223> OTHER INFORMATION: DEVD (PARP) degenerate sequence

<400> SEQUENCE: 21

```
aaacgcaaag gtgatgaagt agatggagta gacgaa                             36
```

<210> SEQ ID NO 22
<211> LENGTH: 12
<212> TYPE: PRT
<213> ORGANISM: Artificial Sequence
<220> FEATURE:
<223> OTHER INFORMATION: DEVD (PARP)

<400> SEQUENCE: 22

```
Lys Arg Lys Gly Asp Glu Val Asp Gly Val Asp Glu
1               5                   10
```

<210> SEQ ID NO 23
<211> LENGTH: 945
<212> TYPE: DNA
<213> ORGANISM: Artificial Sequence
<220> FEATURE:
<223> OTHER INFORMATION: ERT2 (degenerate)

<400> SEQUENCE: 23

```
gcagggggata tgcgcgcagc aaacctctgg ccttcacccc tgatgataaa gaggtcaaag    60
aaaaactctc tcgctctgtc actcaccgca gatcaaatgg tgtccgcact gctggacgcc   120
gagcctccaa tattgtacag tgaatacgat cccactcggc ttttttccga ggcctccatg   180
atggggctcc tcacaaatct cgccgatcga gaacttgtgc atatgataaa ttgggccaaa   240
cgagtccctg gtttcgttga tcttactctg cacgaccaag tacatctgct ggagtgcgct   300
tggctggaaa ttctcatgat cgggctggta tgaggagca tggaacatcc cgtcaaactg   360
ctcttcgccc ccaacctctt gctcgaccga aatcagggga agtgcgtgga agggatggta   420
gaaatatttg atatgctcct ggccacaagc agcagattca gaatgatgaa cctccaaggc   480
gaagaattcg tttgtttgaa gagcatcatc ctgctcaaca gcggcgtcta taccttcctc   540
tcctccacgt tgaaaagcct tgaggaaaaa gatcacatcc atagggtact tgataaaatt   600
actgataccc tcatacacct tatggcaaaa gcgggactca cacttcaaca acaacatcaa   660
```

```
agactcgcac aattgttgtt gattttgagc catataaggc atatgtcaaa taagggaatg    720
gaacacctct actctatgaa atgtaagaat gtcgtcccac tgtacgatct tctccttgaa    780
gctgcagatg ctcatcggct ccacgcacct acctctcggg gcggcgctag cgttgaagag    840
actgatcagt cacatctcgc gacagctgga agcacaagca gccacagcct ccaaaaatac    900
tatattacag gcgaggccga aggcttcccc gctacggccg tggat                    945
```

```
<210> SEQ ID NO 24
<211> LENGTH: 315
<212> TYPE: PRT
<213> ORGANISM: Artificial Sequence
<220> FEATURE:
<223> OTHER INFORMATION: ERT2

<400> SEQUENCE: 24
```

```
Ala Gly Asp Met Arg Ala Ala Asn Leu Trp Pro Ser Pro Leu Met Ile
1               5                   10                  15

Lys Arg Ser Lys Lys Asn Ser Leu Ala Leu Ser Leu Thr Ala Asp Gln
            20                  25                  30

Met Val Ser Ala Leu Leu Asp Ala Glu Pro Pro Ile Leu Tyr Ser Glu
        35                  40                  45

Tyr Asp Pro Thr Arg Pro Phe Ser Glu Ala Ser Met Met Gly Leu Leu
    50                  55                  60

Thr Asn Leu Ala Asp Arg Glu Leu Val His Met Ile Asn Trp Ala Lys
65                  70                  75                  80

Arg Val Pro Gly Phe Val Asp Leu Thr Leu His Asp Gln Val His Leu
                85                  90                  95

Leu Glu Cys Ala Trp Leu Glu Ile Leu Met Ile Gly Leu Val Trp Arg
            100                 105                 110

Ser Met Glu His Pro Val Lys Leu Leu Phe Ala Pro Asn Leu Leu Leu
        115                 120                 125

Asp Arg Asn Gln Gly Lys Cys Val Glu Gly Met Val Glu Ile Phe Asp
    130                 135                 140

Met Leu Leu Ala Thr Ser Ser Arg Phe Arg Met Met Asn Leu Gln Gly
145                 150                 155                 160

Glu Glu Phe Val Cys Leu Lys Ser Ile Ile Leu Leu Asn Ser Gly Val
                165                 170                 175

Tyr Thr Phe Leu Ser Ser Thr Leu Lys Ser Leu Glu Glu Lys Asp His
            180                 185                 190

Ile His Arg Val Leu Asp Lys Ile Thr Asp Thr Leu Ile His Leu Met
        195                 200                 205

Ala Lys Ala Gly Leu Thr Leu Gln Gln Gln His Gln Arg Leu Ala Gln
    210                 215                 220

Leu Leu Leu Ile Leu Ser His Ile Arg His Met Ser Asn Lys Gly Met
225                 230                 235                 240

Glu His Leu Tyr Ser Met Lys Cys Lys Asn Val Val Pro Leu Tyr Asp
                245                 250                 255

Leu Leu Leu Glu Ala Ala Asp Ala His Arg Leu His Ala Pro Thr Ser
            260                 265                 270

Arg Gly Gly Ala Ser Val Glu Glu Thr Asp Gln Ser His Leu Ala Thr
        275                 280                 285

Ala Gly Ser Thr Ser Ser His Ser Leu Gln Lys Tyr Tyr Ile Thr Gly
    290                 295                 300
```

```
Glu Ala Glu Gly Phe Pro Ala Thr Ala Val Asp
305                 310                 315

<210> SEQ ID NO 25
<211> LENGTH: 54
<212> TYPE: DNA
<213> ORGANISM: Artificial Sequence
<220> FEATURE:
<223> OTHER INFORMATION: NES (degenerate)

<400> SEQUENCE: 25
aatcttgtag atcttcagaa aaaactcgaa gaacttgagc ttgatgaaca acaa        54

<210> SEQ ID NO 26
<211> LENGTH: 18
<212> TYPE: PRT
<213> ORGANISM: Artificial Sequence
<220> FEATURE:
<223> OTHER INFORMATION: NES

<400> SEQUENCE: 26

Asn Leu Val Asp Leu Gln Lys Lys Leu Glu Glu Leu Glu Leu Asp Glu
1               5                   10                  15

Gln Gln

<210> SEQ ID NO 27
<211> LENGTH: 1836
<212> TYPE: DNA
<213> ORGANISM: Artificial Sequence
<220> FEATURE:
<223> OTHER INFORMATION: Lyn11-NES-ERT2-DEVD-rtTA NT (with flexible
      linker following Lyn11)

<400> SEQUENCE: 27
ggatgtataa aatcaaaagg gaaagacagc gcgggagcag atagtgctgg tagtgctggt     60
aacctggtgg acctccaaaa gaagctggag gagctggagc tggacgagca gcaggctgga   120
gacatgagag ctgccaacct ttggccaagc ccgctcatga tcaaacgctc taagaagaac   180
agcctggcct tgtccctgac ggccgaccag atggtcagtg ccttgttgga tgctgagccc   240
cccatactct attccgagta tgatcctacc agacccttca gtgaagcttc gatgatgggc   300
ttactgacca acctggcaga cagggagctg gttcacatga tcaactgggc gaagagggtg   360
ccaggctttg tggatttgac cctccatgat caggtccacc ttctagaatg tgcctggcta   420
gagatcctga tgattggtct cgtctggcgc tccatggagc acccagtgaa gctactgttt   480
gctcctaact tgctcttgga caggaaccag ggaaaatgtg tagagggcat ggtggagatc   540
ttcgacatgc tgctggctac atcatctcgg ttccgcatga tgaatctgca gggagaggag   600
tttgtgtgcc tcaaatctat tattttgctt aattctggag tgtacacatt tctgtccagc   660
accctgaagt ctctggaaga gaaggaccat atccaccgag tcctggacaa gatcacagac   720
actttgatcc acctgatggc caaggcaggc ctgaccctgc agcagcagca ccagcggctg   780
gcccagctcc tcctcatcct ctcccacatc aggcacatga gtaacaaagg catggagcat   840
ctgtacagca tgaagtgcaa gaacgtggtg cccctctatg acctgctgct ggaggcggcg   900
gacgcccacc gcctacatgc gcccactagc cgtggagggg catccgtgga ggagacggac   960
caaagccact tggccactgc gggctctact tcatcgcatt ccttgcaaaa gtattacatc  1020
acgggggagg cagagggttt ccctgccaca gctgtcgaca gaggaaggg cgacgaggtg   1080 gacggcgtgg acgagtctag actggacaag agcaaagtca taaacggcgc tctggaatta  1140
```

```
ctcaatggag tcggtatcga aggcctgacg acaaggaaac tcgctcaaaa gctgggagtt    1200
gagcagccta ccctgtactg gcacgtgaag aacaagcggg ccctgctcga tgccctgcca    1260
atcgagatgc tggacaggca tcatacccac ttctgccccc tggaaggcga gtcatggcaa    1320
gactttctgc ggaacaacgc caagtcattc cgctgtgctc tcctctcaca tcgcgacggg    1380
gctaaagtgc atctcggcac ccgcccaaca gagaaacagt acgaaaccct ggaaaatcag    1440
ctcgcgttcc tgtgtcagca aggcttctcc tggagaacg cactgtacgc tctgtccgcc    1500
gtgggccact ttacactggg ctgcgtattg gaggaacagg agcatcaagt agcaaaagag    1560
gaaagagaga cacctaccac cgattctatg ccccacttc tgagacaagc aattgagctg    1620
ttcgaccggc agggagccga acctgccttc cttttcggcc tggaactaat catatgtggc    1680
ctggagaaac agctaaagtg cgaaagcggc gggccggccg acgcccttga cgattttgac    1740
ttagacatgc tcccagccga tgcccttgac gactttgacc ttgatatgct gcctgctgac    1800
gctcttgacg attttgacct tgacatgctc cccggg                              1836
```

<210> SEQ ID NO 28
<211> LENGTH: 612
<212> TYPE: PRT
<213> ORGANISM: Artificial Sequence
<220> FEATURE:
<223> OTHER INFORMATION: Lyn11-NES-ERT2-DEVD-rtTA A (with flexible linker following Lyn11)

<400> SEQUENCE: 28

```
Gly Cys Ile Lys Ser Lys Gly Lys Asp Ser Ala Gly Ala Asp Ser Ala
1               5                   10                  15

Gly Ser Ala Gly Asn Leu Val Asp Leu Gln Lys Lys Leu Glu Glu Leu
            20                  25                  30

Glu Leu Asp Glu Gln Gln Ala Gly Asp Met Arg Ala Ala Asn Leu Trp
        35                  40                  45

Pro Ser Pro Leu Met Ile Lys Arg Ser Lys Lys Asn Ser Leu Ala Leu
    50                  55                  60

Ser Leu Thr Ala Asp Gln Met Val Ser Ala Leu Leu Asp Ala Glu Pro
65                  70                  75                  80

Pro Ile Leu Tyr Ser Glu Tyr Asp Pro Thr Arg Pro Phe Ser Glu Ala
                85                  90                  95

Ser Met Met Gly Leu Leu Thr Asn Leu Ala Asp Arg Glu Leu Val His
            100                 105                 110

Met Ile Asn Trp Ala Lys Arg Val Pro Gly Phe Val Asp Leu Thr Leu
        115                 120                 125

His Asp Gln Val His Leu Leu Glu Cys Ala Trp Leu Glu Ile Leu Met
    130                 135                 140

Ile Gly Leu Val Trp Arg Ser Met Glu His Pro Val Lys Leu Leu Phe
145                 150                 155                 160

Ala Pro Asn Leu Leu Leu Asp Arg Asn Gln Gly Lys Cys Val Glu Gly
                165                 170                 175

Met Val Glu Ile Phe Asp Met Leu Leu Ala Thr Ser Ser Arg Phe Arg
            180                 185                 190

Met Met Asn Leu Gln Gly Glu Glu Phe Val Cys Leu Lys Ser Ile Ile
        195                 200                 205

Leu Leu Asn Ser Gly Val Tyr Thr Phe Leu Ser Ser Thr Leu Lys Ser
    210                 215                 220
```

```
Leu Glu Glu Lys Asp His Ile His Arg Val Leu Asp Lys Ile Thr Asp
225                 230                 235                 240

Thr Leu Ile His Leu Met Ala Lys Ala Gly Leu Thr Leu Gln Gln Gln
            245                 250                 255

His Gln Arg Leu Ala Gln Leu Leu Ile Leu Ser His Ile Arg His
        260                 265                 270

Met Ser Asn Lys Gly Met Glu His Leu Tyr Ser Met Lys Cys Lys Asn
            275                 280                 285

Val Val Pro Leu Tyr Asp Leu Leu Glu Ala Ala Asp Ala His Arg
        290                 295                 300

Leu His Ala Pro Thr Ser Arg Gly Gly Ala Ser Val Glu Glu Thr Asp
305                 310                 315                 320

Gln Ser His Leu Ala Thr Ala Gly Ser Thr Ser Ser His Ser Leu Gln
                325                 330                 335

Lys Tyr Tyr Ile Thr Gly Glu Ala Glu Gly Phe Pro Ala Thr Ala Val
            340                 345                 350

Asp Lys Arg Lys Gly Asp Glu Val Asp Gly Val Asp Glu Ser Arg Leu
        355                 360                 365

Asp Lys Ser Lys Val Ile Asn Gly Ala Leu Glu Leu Leu Asn Gly Val
370                 375                 380

Gly Ile Glu Gly Leu Thr Thr Arg Lys Leu Ala Gln Lys Leu Gly Val
385                 390                 395                 400

Glu Gln Pro Thr Leu Tyr Trp His Val Lys Asn Lys Arg Ala Leu Leu
                405                 410                 415

Asp Ala Leu Pro Ile Glu Met Leu Asp Arg His His Thr His Phe Cys
            420                 425                 430

Pro Leu Glu Gly Glu Ser Trp Gln Asp Phe Leu Arg Asn Asn Ala Lys
        435                 440                 445

Ser Phe Arg Cys Ala Leu Leu Ser His Arg Asp Gly Ala Lys Val His
450                 455                 460

Leu Gly Thr Arg Pro Thr Glu Lys Gln Tyr Glu Thr Leu Glu Asn Gln
465                 470                 475                 480

Leu Ala Phe Leu Cys Gln Gln Gly Phe Ser Leu Glu Asn Ala Leu Tyr
                485                 490                 495

Ala Leu Ser Ala Val Gly His Phe Thr Leu Gly Cys Val Leu Glu Glu
            500                 505                 510

Gln Glu His Gln Val Ala Lys Glu Glu Arg Glu Thr Pro Thr Thr Asp
        515                 520                 525

Ser Met Pro Pro Leu Leu Arg Gln Ala Ile Glu Leu Phe Asp Arg Gln
530                 535                 540

Gly Ala Glu Pro Ala Phe Leu Phe Gly Leu Glu Leu Ile Ile Cys Gly
545                 550                 555                 560

Leu Glu Lys Gln Leu Lys Cys Glu Ser Gly Gly Pro Ala Asp Ala Leu
                565                 570                 575

Asp Asp Phe Asp Leu Asp Met Leu Pro Ala Asp Ala Leu Asp Asp Phe
            580                 585                 590

Asp Leu Asp Met Leu Pro Ala Asp Ala Leu Asp Asp Phe Asp Leu Asp
        595                 600                 605

Met Leu Pro Gly
    610

<210> SEQ ID NO 29
<211> LENGTH: 891
```

```
<212> TYPE: DNA
<213> ORGANISM: Artificial Sequence
<220> FEATURE:
<223> OTHER INFORMATION: Lyn11-NES- DEVD-rtTA

<400> SEQUENCE: 29
ggatgtataa aatcaaaagg gaaagacagc gcgggagcag atagtgctgg tagtgctggt     60
aacctggtgg acctccaaaa gaagctggag gagctggagc tggacgagca gcagaagagg    120
aagggcgacg aggtggacgg cgtggacgag tctagactgg acaagagcaa agtcataaac    180
ggcgctctgg aattactcaa tggagtcggt atcgaaggcc tgacgacaag gaaactcgct    240
caaaagctgg gagttgagca gcctaccctg tactggcacg tgaagaacaa gcgggccctg    300
ctcgatgccc tgccaatcga gatgctggac aggcatcata cccacttctg cccctggaa     360 ggcgagtcat ggcaagactt tctgcggaac aacgccaagt cattccgctg tgctctcctc    420
tcacatcgcg acgggctaa agtgcatctc ggcacccgcc aacagagaa acagtacgaa     480 accctggaaa atcagctcgc gttcctgtgt cagcaaggct ctcccctgga aacgcactg     540 tacgctctgt ccgccgtggg ccactttaca ctgggctgcg tattggagga acaggagcat    600
caagtagcaa aagaggaaag agagacacct accaccgatt ctatgccccc acttctgaga    660
caagcaattg agctgttcga ccggcaggga gccgaacctg ccttccttt cggcctggaa    720 ctaatcatat gtggcctgga gaaacagcta aagtgcgaaa gcggcgggcc ggccgacgcc    780
cttgacgatt ttgacttaga catgctccca gccgatgccc ttgacgactt tgaccttgat    840
atgctgcctg ctgacgctct tgacgatttt gaccttgaca tgctccccgg g             891

<210> SEQ ID NO 30
<211> LENGTH: 297
<212> TYPE: PRT
<213> ORGANISM: Artificial Sequence
<220> FEATURE:
<223> OTHER INFORMATION: Lyn11-NES- DEVD-rtTA

<400> SEQUENCE: 30

Gly Cys Ile Lys Ser Lys Gly Lys Asp Ser Ala Gly Ala Asp Ser Ala
1               5                   10                  15

Gly Ser Ala Gly Asn Leu Val Asp Leu Gln Lys Lys Leu Glu Glu Leu
            20                  25                  30

Glu Leu Asp Glu Gln Gln Lys Arg Lys Gly Asp Glu Val Asp Gly Val
        35                  40                  45

Asp Glu Ser Arg Leu Asp Lys Ser Lys Val Ile Asn Gly Ala Leu Glu
    50                  55                  60

Leu Leu Asn Gly Val Gly Ile Glu Gly Leu Thr Thr Arg Lys Leu Ala
65                  70                  75                  80

Gln Lys Leu Gly Val Glu Gln Pro Thr Leu Tyr Trp His Val Lys Asn
                85                  90                  95

Lys Arg Ala Leu Leu Asp Ala Leu Pro Ile Glu Met Leu Asp Arg His
            100                 105                 110

His Thr His Phe Cys Pro Leu Glu Gly Glu Ser Trp Gln Asp Phe Leu
        115                 120                 125

Arg Asn Asn Ala Lys Ser Phe Arg Cys Ala Leu Leu Ser His Arg Asp
    130                 135                 140

Gly Ala Lys Val His Leu Gly Thr Arg Pro Thr Glu Lys Gln Tyr Glu
145                 150                 155                 160

Thr Leu Glu Asn Gln Leu Ala Phe Leu Cys Gln Gln Gly Phe Ser Leu
                165                 170                 175
```

```
Glu Asn Ala Leu Tyr Ala Leu Ser Ala Val Gly His Phe Thr Leu Gly
            180                 185                 190
Cys Val Leu Glu Glu Gln Glu His Gln Val Ala Lys Glu Glu Arg Glu
        195                 200                 205
Thr Pro Thr Thr Asp Ser Met Pro Pro Leu Leu Arg Gln Ala Ile Glu
    210                 215                 220
Leu Phe Asp Arg Gln Gly Ala Glu Pro Ala Phe Leu Phe Gly Leu Glu
225                 230                 235                 240
Leu Ile Ile Cys Gly Leu Glu Lys Gln Leu Lys Cys Glu Ser Gly Gly
                245                 250                 255
Pro Ala Asp Ala Leu Asp Asp Phe Asp Leu Asp Met Leu Pro Ala Asp
            260                 265                 270
Ala Leu Asp Asp Phe Asp Leu Asp Met Leu Pro Ala Asp Ala Leu Asp
        275                 280                 285
Asp Phe Asp Leu Asp Met Leu Pro Gly
    290                 295

<210> SEQ ID NO 31
<211> LENGTH: 1899
<212> TYPE: DNA
<213> ORGANISM: Artificial Sequence
<220> FEATURE:
<223> OTHER INFORMATION: Lyn11-NES-ERT2-DEVD-rtTA-3xFLAG

<400> SEQUENCE: 31
ggatgtataa aatcaaaagg gaaagacagc gcgggagcag atagtgctgg tagtgctggt      60
aacctggtgg aacctccaaaa gaagctggag gagctggagc tggacgagca gcaggctgga    120
gacatgagag ctgccaacct ttggccaagc ccgctcatga tcaaacgctc taagaagaac    180
agcctggcct tgtccctgac ggccgaccag atggtcagtg ccttgttgga tgctgagccc    240
cccatactct attccgagta tgatcctacc agacccttca gtgaagcttc gatgatgggc    300
ttactgacca acctggcaga cagggagctg gttcacatga tcaactgggc gaagagggtg    360
ccaggctttg tggatttgac cctccatgat caggtccacc ttctagaatg tgcctggcta    420
gagatcctga tgattggtct cgtctggcgc tccatggagc acccagtgaa gctactgttt    480
gctcctaact tgctcttgga caggaaccag ggaaaatgtg tagagggcat ggtggagatc    540
ttcgacatgc tgctggctac atcatctcgg ttccgcatga tgaatctgca gggagaggag    600
tttgtgtgcc tcaaatctat tattttgctt aattctggag tgtacacatt tctgtccagc    660
accctgaagt ctctggaaga gaaggaccat atccaccgag tcctggacaa gatcacagac    720
actttgatcc acctgatggc caaggcaggc ctgaccctgc agcagcagca ccagcggctg    780
gcccagctcc tcctcatcct ctcccacatc aggcacatga gtaacaaagg catggagcat    840
ctgtacagca tgaagtgcaa gaacgtggtg cccctctatg acctgctgct ggaggcggcg    900
gacgcccacc gcctacatgc gcccactagc cgtggagggg catccgtgga ggagacggac    960
caaagccact tggccactgc gggctctact tcatcgcatt ccttgcaaaa gtattacatc   1020 acggggagg cagagggttt ccctgccaca gctgtcgaca agaggaaggg cgacgaggtg    1080
gacggcgtgg acgagtctag actggacaag agcaaagtca taaacggcgc tctggaatta   1140
ctcaatggag tcggtatcga aggcctgacg acaaggaaac tcgctcaaaa gctgggagtt   1200
gagcagccta ccctgtactg gcacgtgaag aacaagcggg ccctgctcga tgccctgcca   1260
atcgagatgc tggacaggca tcatacccac ttctgcccccc tggaaggcga gtcatggcaa   1320
```

-continued

```
gactttctgc ggaacaacgc caagtcattc cgctgtgctc tcctctcaca tcgcgacggg    1380
gctaaagtgc atctcggcac ccgcccaaca gagaaacagt acgaaaccct ggaaaatcag    1440
ctcgcgttcc tgtgtcagca aggcttctcc ctggagaacg cactgtacgc tctgtccgcc    1500
gtgggccact ttacactggg ctgcgtattg gaggaacagg agcatcaagt agcaaaagag    1560
gaaagagaga cacctaccac cgattctatg cccccacttc tgagacaagc aattgagctg    1620
ttcgaccggc agggagccga acctgccttc cttttcggcc tggaactaat catatgtggc    1680
ctggagaaac agctaaagtg cgaaagcggc gggccggccg acgcccttga cgattttgac    1740
ttagacatgc tcccagccga tgcccttgac gactttgacc ttgatatgct gcctgctgac    1800
gctcttgacg attttgacct tgacatgctc cccggggact acaaagacca tgacggtgat    1860
tataaagatc atgacatcga ttacaaggat gacgatgac                           1899
```

<210> SEQ ID NO 32
<211> LENGTH: 633
<212> TYPE: PRT
<213> ORGANISM: Artificial Sequence
<220> FEATURE:
<223> OTHER INFORMATION: Lyn11-NES-ERT2-DEVD-rtTA-3xFLAG

<400> SEQUENCE: 32

```
Gly Cys Ile Lys Ser Lys Gly Lys Asp Ser Ala Gly Ala Asp Ser Ala
1               5                   10                  15

Gly Ser Ala Gly Asn Leu Val Asp Leu Gln Lys Lys Leu Glu Glu Leu
            20                  25                  30

Glu Leu Asp Glu Gln Gln Ala Gly Asp Met Arg Ala Ala Asn Leu Trp
        35                  40                  45

Pro Ser Pro Leu Met Ile Lys Arg Ser Lys Lys Asn Ser Leu Ala Leu
    50                  55                  60

Ser Leu Thr Ala Asp Gln Met Val Ser Ala Leu Leu Asp Ala Glu Pro
65                  70                  75                  80

Pro Ile Leu Tyr Ser Glu Tyr Asp Pro Thr Arg Pro Phe Ser Glu Ala
                85                  90                  95

Ser Met Met Gly Leu Leu Thr Asn Leu Ala Asp Arg Glu Leu Val His
            100                 105                 110

Met Ile Asn Trp Ala Lys Arg Val Pro Gly Phe Val Asp Leu Thr Leu
        115                 120                 125

His Asp Gln Val His Leu Leu Glu Cys Ala Trp Leu Glu Ile Leu Met
    130                 135                 140

Ile Gly Leu Val Trp Arg Ser Met Glu His Pro Val Lys Leu Leu Phe
145                 150                 155                 160

Ala Pro Asn Leu Leu Leu Asp Arg Asn Gln Gly Lys Cys Val Glu Gly
                165                 170                 175

Met Val Glu Ile Phe Asp Met Leu Leu Ala Thr Ser Ser Arg Phe Arg
            180                 185                 190

Met Met Asn Leu Gln Gly Glu Glu Phe Val Cys Leu Lys Ser Ile Ile
        195                 200                 205

Leu Leu Asn Ser Gly Val Tyr Thr Phe Leu Ser Ser Thr Leu Lys Ser
    210                 215                 220

Leu Glu Glu Lys Asp His Ile His Arg Val Leu Asp Lys Ile Thr Asp
225                 230                 235                 240

Thr Leu Ile His Leu Met Ala Lys Ala Gly Leu Thr Leu Gln Gln Gln
                245                 250                 255
```

His Gln Arg Leu Ala Gln Leu Leu Ile Leu Ser His Ile Arg His
                260                 265                 270

Met Ser Asn Lys Gly Met Glu His Leu Tyr Ser Met Lys Cys Lys Asn
            275                 280                 285

Val Val Pro Leu Tyr Asp Leu Leu Glu Ala Asp Ala His Arg
290                 295                 300

Leu His Ala Pro Thr Ser Arg Gly Gly Ala Ser Val Glu Glu Thr Asp
305                 310                 315                 320

Gln Ser His Leu Ala Thr Ala Gly Ser Thr Ser Ser His Ser Leu Gln
                325                 330                 335

Lys Tyr Tyr Ile Thr Gly Glu Ala Glu Gly Phe Pro Ala Thr Ala Val
            340                 345                 350

Asp Lys Arg Lys Gly Asp Glu Val Asp Gly Val Asp Glu Ser Arg Leu
        355                 360                 365

Asp Lys Ser Lys Val Ile Asn Gly Ala Leu Glu Leu Leu Asn Gly Val
    370                 375                 380

Gly Ile Glu Gly Leu Thr Thr Arg Lys Leu Ala Gln Lys Leu Gly Val
385                 390                 395                 400

Glu Gln Pro Thr Leu Tyr Trp His Val Lys Asn Lys Arg Ala Leu Leu
                405                 410                 415

Asp Ala Leu Pro Ile Glu Met Leu Asp Arg His His Thr His Phe Cys
            420                 425                 430

Pro Leu Glu Gly Glu Ser Trp Gln Asp Phe Leu Arg Asn Asn Ala Lys
        435                 440                 445

Ser Phe Arg Cys Ala Leu Leu Ser His Arg Asp Gly Ala Lys Val His
    450                 455                 460

Leu Gly Thr Arg Pro Thr Glu Lys Gln Tyr Glu Thr Leu Glu Asn Gln
465                 470                 475                 480

Leu Ala Phe Leu Cys Gln Gln Gly Phe Ser Leu Glu Asn Ala Leu Tyr
                485                 490                 495

Ala Leu Ser Ala Val Gly His Phe Thr Leu Gly Cys Val Leu Glu Glu
            500                 505                 510

Gln Glu His Gln Val Ala Lys Glu Glu Arg Glu Thr Pro Thr Thr Asp
        515                 520                 525

Ser Met Pro Pro Leu Leu Arg Gln Ala Ile Glu Leu Phe Asp Arg Gln
    530                 535                 540

Gly Ala Glu Pro Ala Phe Leu Phe Gly Leu Glu Leu Ile Ile Cys Gly
545                 550                 555                 560

Leu Glu Lys Gln Leu Lys Cys Glu Ser Gly Pro Ala Asp Ala Leu
                565                 570                 575

Asp Asp Phe Asp Leu Asp Met Leu Pro Ala Asp Ala Leu Asp Asp Phe
            580                 585                 590

Asp Leu Asp Met Leu Pro Ala Asp Ala Leu Asp Phe Asp Leu Asp
        595                 600                 605

Met Leu Pro Gly Asp Tyr Lys Asp His Asp Gly Asp Tyr Lys Asp His
    610                 615                 620

Asp Ile Asp Tyr Lys Asp Asp Asp Asp
625                 630

<210> SEQ ID NO 33
<211> LENGTH: 954
<212> TYPE: DNA
<213> ORGANISM: Artificial Sequence
<220> FEATURE:

<223> OTHER INFORMATION: Lyn11-NES- DEVD-rtTA-3xFLAG

<400> SEQUENCE: 33

```
ggatgtataa aatcaaaagg gaaagacagc gcgggagcag atagtgctgg tagtgctggt      60
aacctggtgg acctccaaaa gaagctggag gagctggagc tggacgagca gcagaagagg     120
aagggcgacg aggtggacgg cgtggacgag tctagactgg acaagagcaa agtcataaac     180
ggcgctctgg aattactcaa tggagtcggt atcgaaggcc tgacgacaag gaaactcgct     240
caaaagctgg gagttgagca gcctaccctg tactggcacg tgaagaacaa gcgggccctg     300
ctcgatgccc tgccaatcga gatgctggac aggcatcata cccacttctg ccccctggaa     360
ggcgagtcat ggcaagactt tctgcggaac aacgccaagt cattccgctg tgctctcctc     420
tcacatcgcg acggggctaa agtgcatctc ggcacccgcc aacagagaa acagtacgaa      480
accctggaaa atcagctcgc gttcctgtgt cagcaaggct ctcccctgga gaacgcactg     540
tacgctctgt ccgccgtggg ccactttaca ctgggctgcg tattggagga acaggagcat     600
caagtagcaa aagaggaaag agagacacct accaccgatt ctatgccccc acttctgaga     660
caagcaattg agctgttcga ccggcaggga gccgaacctg ccttccttt cggcctggaa      720
ctaatcatat gtggcctgga gaaacagcta aagtgcgaaa gcggcgggcc ggccgacgcc     780
cttgacgatt ttgacttaga catgctccca gccgatgccc ttgacgactt tgaccttgat     840
atgctgcctg ctgacgctct tgacgatttt gaccttgaca tgctccccgg ggactacaaa     900
gaccatgacg gtgattataa agatcatgac atcgattaca aggatgacga tgac          954
```

<210> SEQ ID NO 34
<211> LENGTH: 318
<212> TYPE: PRT
<213> ORGANISM: Artificial Sequence
<220> FEATURE:
<223> OTHER INFORMATION: Lyn11-NES- DEVD-rtTA-3xFLAG

<400> SEQUENCE: 34

```
Gly Cys Ile Lys Ser Lys Gly Lys Asp Ser Ala Gly Ala Asp Ser Ala
1               5                   10                  15

Gly Ser Ala Gly Asn Leu Val Asp Leu Gln Lys Lys Leu Glu Glu Leu
            20                  25                  30

Glu Leu Asp Glu Gln Gln Lys Arg Lys Gly Asp Glu Val Asp Gly Val
        35                  40                  45

Asp Glu Ser Arg Leu Asp Lys Ser Lys Val Ile Asn Gly Ala Leu Glu
    50                  55                  60

Leu Leu Asn Gly Val Gly Ile Glu Gly Leu Thr Thr Arg Lys Leu Ala
65                  70                  75                  80

Gln Lys Leu Gly Val Glu Gln Pro Thr Leu Tyr Trp His Val Lys Asn
                85                  90                  95

Lys Arg Ala Leu Leu Asp Ala Leu Pro Ile Glu Met Leu Asp Arg His
            100                 105                 110

His Thr His Phe Cys Pro Leu Glu Gly Glu Ser Trp Gln Asp Phe Leu
        115                 120                 125

Arg Asn Asn Ala Lys Ser Phe Arg Cys Ala Leu Leu Ser His Arg Asp
    130                 135                 140

Gly Ala Lys Val His Leu Gly Thr Arg Pro Thr Glu Lys Gln Tyr Glu
145                 150                 155                 160

Thr Leu Glu Asn Gln Leu Ala Phe Leu Cys Gln Gln Gly Phe Ser Leu
                165                 170                 175
```

Glu Asn Ala Leu Tyr Ala Leu Ser Ala Val Gly His Phe Thr Leu Gly
            180                 185                 190

Cys Val Leu Glu Glu Gln Glu His Gln Val Ala Lys Glu Glu Arg Glu
        195                 200                 205

Thr Pro Thr Thr Asp Ser Met Pro Pro Leu Leu Arg Gln Ala Ile Glu
    210                 215                 220

Leu Phe Asp Arg Gln Gly Ala Glu Pro Ala Phe Leu Phe Gly Leu Glu
225                 230                 235                 240

Leu Ile Ile Cys Gly Leu Glu Lys Gln Leu Lys Cys Glu Ser Gly Gly
                245                 250                 255

Pro Ala Asp Ala Leu Asp Asp Phe Asp Leu Asp Met Leu Pro Ala Asp
            260                 265                 270

Ala Leu Asp Asp Phe Asp Leu Asp Met Leu Pro Ala Asp Ala Leu Asp
        275                 280                 285

Asp Phe Asp Leu Asp Met Leu Pro Gly Asp Tyr Lys Asp His Asp Gly
290                 295                 300

Asp Tyr Lys Asp His Asp Ile Asp Tyr Lys Asp Asp Asp Asp
305                 310                 315

<210> SEQ ID NO 35
<211> LENGTH: 2769
<212> TYPE: DNA
<213> ORGANISM: Artificial Sequence
<220> FEATURE:
<223> OTHER INFORMATION: ERT2-DEVD-rtTA-3xFLAG-DEVD-ERT2 NT with GCA
      after flag

<400> SEQUENCE: 35
gctggagaca tgagagctgc aaccctttgg ccaagcccgc tcatgatcaa acgctctaag      60
aagaacagcc tggccttgtc cctgacggcc gaccagatgg tcagtgcctt gttggatgct    120 gagccccca tactctattc cgagtatgat cctaccagac ccttcagtga agcttcgatg     180
atgggcttac tgaccaacct ggcagacagg gagctggttc acatgatcaa ctgggcgaag    240
agggtgccag gctttgtgga tttgaccctc catgatcagg tccaccttct agaatgtgcc    300
tggctagaga tcctgatgat tggtctcgtc tggcgctcca tggagcaccc agtgaagcta    360
ctgtttgctc ctaacttgct cttggacagg aaccagggaa aatgtgtaga gggcatggtg    420
gagatcttcg acatgctgct ggctacatca tctcggttcc gcatgatgaa tctgcaggga    480
gaggagtttg tgtgcctcaa atctattatt ttgcttaatt ctggagtgta cacatttctg    540
tccagcaccc tgaagtctct ggaagagaag gaccatatcc accgagtcct ggacaagatc    600
acagacactt tgatccacct gatggccaag gcaggcctga ccctgcagca gcagcaccag    660
cggctggccc agctcctcct catcctctcc cacatcaggc acatgagtaa caaaggcatg    720
gagcatctgt acagcatgaa gtgcaagaac gtggtgcccc tctatgacct gctgctggag    780
gcggcggacg cccaccgcct acatgcgccc actagccgtg gaggggcatc cgtggaggag    840
acggaccaaa gccacttggc cactgcgggc tctacttcat cgcattcctt gcaaaagtat    900
tacatcacgg gggaggcaga gggttttcct gccacagctg tcgacaagag aagggcgac     960 gaggtggacg cgtgacga gtctagactg acaagagca aagtcataaa cggcgctctg      1020
gaattactca atggagtcgg tatcgaaggc ctgacgacaa ggaaactcgc tcaaaagctg   1080
ggagttgagc agcctaccct gtactggcac gtgaagaaca gcgggcct gctcgatgcc    1140 ctgccaatcg agatgctgga caggcatcat acccacttct gccccctgga aggcgagtca   1200
tggcaagact ttctgcggaa caacgccaag tcattccgct gtgctctcct ctcacatcgc   1260

```
gacggggcta aagtgcatct cggcacccgc ccaacagaga aacagtacga aaccctggaa    1320
aatcagctcg cgttcctgtg tcagcaaggc ttctccctgg agaacgcact gtacgctctg    1380
tccgccgtgg gccactttac actgggctgc gtattggagg aacaggagca tcaagtagca    1440
aaagaggaaa gagagacacc taccaccgat tctatgcccc cacttctgag acaagcaatt    1500
gagctgttcg accggcaggg agccgaacct gccttccttt tcggcctgga actaatcata    1560
tgtggcctgg agaaacagct aaagtgcgaa agcggcgggc cggccgacgc ccttgacgat    1620
tttgacttag acatgctccc agccgatgcc cttgacgact ttgaccttga tatgctgcct    1680
gctgacgctc ttgacgattt tgaccttgac atgctccccg gggactacaa agaccatgac    1740
ggtgattata agatcatga catcgattac aaggatgacg atgacgcaaa acgcaaaggt    1800
gatgaagtag atggagtaga cgaagcaggg gatatgcgcg cagcaaacct ctggccttca    1860 ccccctgatga taaagaggtc aaagaaaaac tctctcgctc tgtcactcac cgcagatcaa    1920
atggtgtccg cactgctgga cgccgagcct ccaatattgt acagtgaata cgatcccact    1980
cggccttttt ccgaggcctc catgatgggg ctcctcacaa atctcgccga tcgagaactt    2040
gtgcatatga taaattgggc caaacgagtc cctggtttcg ttgatcttac tctgcacgac    2100
caagtacatc tgctggagtg cgcttggctg gaaattctca tgatcgggct ggtatggagg    2160
agcatggaac atcccgtcaa actgctcttc gcccccaacc tcttgctcga ccgaaatcag    2220
gggaagtgcg tggaagggat ggtagaaata tttgatatgc tcctggccac aagcagcaga    2280
ttcagaatga tgaacctcca aggcgaagaa ttcgtttgtt tgaagagcat catcctgctc    2340
aacagcggcg tctataccct cctctcctcc acgttgaaaa gccttgagga aaaagatcac    2400
atccataggg tacttgataa aattactgat accctcatac accttatggc aaaagcggga    2460
ctcacacttc aacaacaaca tcaaagactc gcacaattgt tgttgatttt gagccatata    2520
aggcatatgt caaataaggg aatggaacac ctctactcta tgaaatgtaa gaatgtcgtc    2580
ccactgtacg atcttctcct tgaagctgca gatgctcatc ggctccacgc acctacctct    2640
cggggcggcg ctagcgttga agagactgat cagtcacatc tcgcgacagc tggaagcaca    2700
agcagccaca gcctccaaaa atactatatt acaggcgagg ccgaaggctt ccccgctacg    2760
gccgtggat                                                            2769

<210> SEQ ID NO 36
<211> LENGTH: 923
<212> TYPE: PRT
<213> ORGANISM: Artificial Sequence
<220> FEATURE:
<223> OTHER INFORMATION: ERT2-DEVD-rtTA-3xFLAG-DEVD-ERT2

<400> SEQUENCE: 36

Ala Gly Asp Met Arg Ala Ala Asn Leu Trp Pro Ser Pro Leu Met Ile
1               5                   10                  15

Lys Arg Ser Lys Lys Asn Ser Leu Ala Leu Ser Leu Thr Ala Asp Gln
            20                  25                  30

Met Val Ser Ala Leu Leu Asp Ala Glu Pro Pro Ile Leu Tyr Ser Glu
        35                  40                  45

Tyr Asp Pro Thr Arg Pro Phe Ser Glu Ala Ser Met Met Gly Leu Leu
    50                  55                  60

Thr Asn Leu Ala Asp Arg Glu Leu Val His Met Ile Asn Trp Ala Lys
65                  70                  75                  80
```

-continued

Arg Val Pro Gly Phe Val Asp Leu Thr Leu His Asp Gln Val His Leu
             85                  90                  95

Leu Glu Cys Ala Trp Leu Glu Ile Leu Met Ile Gly Leu Val Trp Arg
            100                 105                 110

Ser Met Glu His Pro Val Lys Leu Leu Phe Ala Pro Asn Leu Leu Leu
            115                 120                 125

Asp Arg Asn Gln Gly Lys Cys Val Glu Gly Met Val Glu Ile Phe Asp
130                 135                 140

Met Leu Leu Ala Thr Ser Ser Arg Phe Arg Met Met Asn Leu Gln Gly
145                 150                 155                 160

Glu Glu Phe Val Cys Leu Lys Ser Ile Ile Leu Leu Asn Ser Gly Val
                165                 170                 175

Tyr Thr Phe Leu Ser Ser Thr Leu Lys Ser Leu Glu Glu Lys Asp His
            180                 185                 190

Ile His Arg Val Leu Asp Lys Ile Thr Asp Thr Leu Ile His Leu Met
            195                 200                 205

Ala Lys Ala Gly Leu Thr Leu Gln Gln Gln His Gln Arg Leu Ala Gln
210                 215                 220

Leu Leu Leu Ile Leu Ser His Ile Arg His Met Ser Asn Lys Gly Met
225                 230                 235                 240

Glu His Leu Tyr Ser Met Lys Cys Lys Asn Val Val Pro Leu Tyr Asp
                245                 250                 255

Leu Leu Leu Glu Ala Ala Asp Ala His Arg Leu His Ala Pro Thr Ser
            260                 265                 270

Arg Gly Gly Ala Ser Val Glu Thr Asp Gln Ser His Leu Ala Thr
            275                 280                 285

Ala Gly Ser Thr Ser Ser His Ser Leu Gln Lys Tyr Tyr Ile Thr Gly
290                 295                 300

Glu Ala Glu Gly Phe Pro Ala Thr Ala Val Asp Lys Arg Lys Gly Asp
305                 310                 315                 320

Glu Val Asp Gly Val Asp Glu Ser Arg Leu Asp Lys Ser Lys Val Ile
            325                 330                 335

Asn Gly Ala Leu Glu Leu Leu Asn Gly Val Gly Ile Glu Gly Leu Thr
            340                 345                 350

Thr Arg Lys Leu Ala Gln Lys Leu Gly Val Glu Gln Pro Thr Leu Tyr
            355                 360                 365

Trp His Val Lys Asn Lys Arg Ala Leu Leu Asp Ala Leu Pro Ile Glu
            370                 375                 380

Met Leu Asp Arg His His Thr His Phe Cys Pro Leu Glu Gly Glu Ser
385                 390                 395                 400

Trp Gln Asp Phe Leu Arg Asn Asn Ala Lys Ser Phe Arg Cys Ala Leu
                405                 410                 415

Leu Ser His Arg Asp Gly Ala Lys Val His Leu Gly Thr Arg Pro Thr
            420                 425                 430

Glu Lys Gln Tyr Glu Thr Leu Glu Asn Gln Leu Ala Phe Leu Cys Gln
            435                 440                 445

Gln Gly Phe Ser Leu Glu Asn Ala Leu Tyr Ala Leu Ser Ala Val Gly
450                 455                 460

His Phe Thr Leu Gly Cys Val Leu Glu Glu Gln Glu His Gln Val Ala
465                 470                 475                 480

Lys Glu Glu Arg Glu Thr Pro Thr Thr Asp Ser Met Pro Pro Leu Leu
                485                 490                 495

```
Arg Gln Ala Ile Glu Leu Phe Asp Arg Gln Gly Ala Glu Pro Ala Phe
            500                 505                 510

Leu Phe Gly Leu Glu Leu Ile Ile Cys Gly Leu Glu Lys Gln Leu Lys
        515                 520                 525

Cys Glu Ser Gly Gly Pro Ala Asp Ala Leu Asp Asp Phe Asp Leu Asp
        530                 535                 540

Met Leu Pro Ala Asp Ala Leu Asp Asp Phe Asp Leu Asp Met Leu Pro
545                 550                 555                 560

Ala Asp Ala Leu Asp Asp Phe Asp Leu Asp Met Leu Pro Gly Asp Tyr
                565                 570                 575

Lys Asp His Asp Gly Asp Tyr Lys Asp His Asp Ile Asp Tyr Lys Asp
            580                 585                 590

Asp Asp Asp Ala Lys Arg Lys Gly Asp Glu Val Asp Gly Val Asp Glu
            595                 600                 605

Ala Gly Asp Met Arg Ala Ala Asn Leu Trp Pro Ser Pro Leu Met Ile
        610                 615                 620

Lys Arg Ser Lys Lys Asn Ser Leu Ala Leu Ser Leu Thr Ala Asp Gln
625                 630                 635                 640

Met Val Ser Ala Leu Leu Asp Ala Glu Pro Pro Ile Leu Tyr Ser Glu
                645                 650                 655

Tyr Asp Pro Thr Arg Pro Phe Ser Glu Ala Ser Met Met Gly Leu Leu
                660                 665                 670

Thr Asn Leu Ala Asp Arg Glu Leu Val His Met Ile Asn Trp Ala Lys
        675                 680                 685

Arg Val Pro Gly Phe Val Asp Leu Thr Leu His Asp Gln Val His Leu
        690                 695                 700

Leu Glu Cys Ala Trp Leu Glu Ile Leu Met Ile Gly Leu Val Trp Arg
705                 710                 715                 720

Ser Met Glu His Pro Val Lys Leu Leu Phe Ala Pro Asn Leu Leu Leu
                725                 730                 735

Asp Arg Asn Gln Gly Lys Cys Val Glu Gly Met Val Glu Ile Phe Asp
        740                 745                 750

Met Leu Leu Ala Thr Ser Ser Arg Phe Arg Met Met Asn Leu Gln Gly
        755                 760                 765

Glu Glu Phe Val Cys Leu Lys Ser Ile Ile Leu Leu Asn Ser Gly Val
770                 775                 780

Tyr Thr Phe Leu Ser Ser Thr Leu Lys Ser Leu Glu Glu Lys Asp His
785                 790                 795                 800

Ile His Arg Val Leu Asp Lys Ile Thr Asp Thr Leu Ile His Leu Met
                805                 810                 815

Ala Lys Ala Gly Leu Thr Leu Gln Gln Gln His Gln Arg Leu Ala Gln
                820                 825                 830

Leu Leu Leu Ile Leu Ser His Ile Arg His Met Ser Asn Lys Gly Met
        835                 840                 845

Glu His Leu Tyr Ser Met Lys Cys Lys Asn Val Val Pro Leu Tyr Asp
        850                 855                 860

Leu Leu Leu Glu Ala Ala Asp Ala His Arg Leu His Ala Pro Thr Ser
865                 870                 875                 880

Arg Gly Gly Ala Ser Val Glu Glu Thr Asp Gln Ser His Leu Ala Thr
                885                 890                 895
```

```
Ala Gly Ser Thr Ser Ser His Ser Leu Gln Lys Tyr Tyr Ile Thr Gly
            900                 905                 910

Glu Ala Glu Gly Phe Pro Ala Thr Ala Val Asp
            915                 920

<210> SEQ ID NO 37
<211> LENGTH: 2766
<212> TYPE: DNA
<213> ORGANISM: Artificial Sequence
<220> FEATURE:
<223> OTHER INFORMATION: ERT2-DEVD-rtTA-3xFLAG-DEVD-ERT2 NT w/out GCA
      after flag

<400> SEQUENCE: 37
gctggagaca tgagagctgc aaccctttgg ccaagcccgc tcatgatcaa acgctctaag      60
aagaacagcc tggccttgtc cctgacggcc gaccagatgg tcagtgcctt gttggatgct     120 gagccccca tactctattc cgagtatgat cctaccagac ccttcagtga agcttcgatg      180
atgggcttac tgaccaacct ggcagacagg agctggttc acatgatcaa ctgggcgaag      240
agggtgccag gctttgtgga tttgaccctc catgatcagg tccaccttct agaatgtgcc     300
tggctagaga tcctgatgat tggtctcgtc tggcgctcca tggagcaccc agtgaagcta     360
ctgtttgctc ctaacttgct cttggacagg aaccagggaa atgtgtaga gggcatggtg      420 gagatcttcg acatgctgct ggctacatca tctcggttcc gcatgatgaa tctgcaggga     480
gaggagtttg tgtgcctcaa atctattatt ttgcttaatt ctggagtgta cacatttctg     540
tccagcaccc tgaagtctct ggaagagaag gaccatatcc accgagtcct ggacaagatc     600
acagacactt tgatccacct gatggccaag gcaggcctga ccctgcagca gcagcaccag     660
cggctggccc agtcctcct catcctctcc cacatcaggc acatgagtaa caaaggcatg     720
gagcatctgt acagcatgaa gtgcaagaac gtggtgcccc tctatgacct gctgctggag     780
gcggcggacg cccaccgcct acatgcgccc actagccgtg aggggcatc cgtgaggag      840 acggaccaaa gccacttggc cactgcgggc tctacttcat cgcattcctt gcaaaagtat     900
tacatcacgg gggaggcaga gggttttccct gccacagctg tcgacaagag gaagggcgac     960
gaggtggacg gcgtggacga gtctagactg acaagagca aagtcataaa cggcgctctg    1020
gaattactca atggagtcgg tatcgaaggc ctgacgacaa ggaaactcgc tcaaaagctg    1080
ggagttgagc agcctaccct gtactggcac gtgaagaaca gcgggccct gctcgatgcc    1140 ctgccaatcg agatgctgga caggcatcat acccacttct gccccctgga aggcgagtca    1200
tggcaagact ttctgcggaa caacgccaag tcattccgct gtgctctcct ctcacatcgc    1260
gacggggcta agtgcatct cggcacccgc ccaacagaga aacagtacga aaccctggaa    1320
aatcagctcg cgttcctgtg tcagcaaggc ttctccctgg agaacgcact gtacgctctg    1380
tccgccgtgg ccactttac actgggctgc gtattggagg aacaggagca tcaagtagca    1440
aaagaggaaa gagagacacc taccaccgat tctatgcccc cacttctgag acaagcaatt    1500
gagctgttcg accggcaggg agccgaacct gccttccttt tcggcctgga actaatcata    1560
tgtggcctgg agaaacagct aaagtgcgaa agcggcgggc cggccgacgc ccttgacgat    1620
tttgacttag acatgctccc cagccgatgcc cttgacgact tgaccttga tatgctgcct    1680 gctgacgctc ttgacgatt tgaccttgac atgctccccg ggactacaa agaccatgac    1740 ggtgattata aagatcatga catcgattac aaggatgacg atgacaaacg caaaggtgat    1800
gaagtagatg gagtagacga agcagggat atgcgcgcag caaacctctg gccttcaccc    1860
```

-continued

```
ctgatgataa agaggtcaaa gaaaaactct ctcgctctgt cactcaccgc agatcaaatg    1920
gtgtccgcac tgctggacgc cgagcctcca atattgtaca gtaatacga tcccactcgg    1980
ccttttccg aggcctccat gatggggctc ctcacaaatc tcgccgatcg agaacttgtg    2040
catatgataa attgggccaa acgagtccct ggtttcgttg atcttactct gcacgaccaa    2100
gtacatctgc tggagtgcgc ttggctggaa attctcatga tcgggctggt atggaggagc    2160
atggaacatc ccgtcaaact gctcttcgcc cccaacctct tgctcgaccg aaatcagggg    2220
aagtgcgtgg aagggatggt agaaatattt gatatgctcc tggccacaag cagcagattc    2280
agaatgatga acctccaagg cgaagaattc gtttgtttga agagcatcat cctgctcaac    2340
agcggcgtct ataccttcct ctcctccacg ttgaaaagcc ttgaggaaaa agatcacatc    2400
cataggggtac ttgataaaat tactgatacc ctcatacacc ttatggcaaa agcgggactc    2460
acacttcaac aacaacatca aagactcgca caattgttgt tgattttgag ccatataagg    2520
catatgtcaa ataagggaat ggaacacctc tactctatga aatgtaagaa tgtcgtccca    2580
ctgtacgatc ttctccttga agctgcagat gctcatcggc tccacgcacc tacctctcgg    2640
ggcggcgcta gcgttgaaga gactgatcag tcacatctcg cgacagctgg aagcacaagc    2700
agccacagcc tccaaaaata ctatattaca ggcgaggccg aaggcttccc cgctacggcc    2760
gtggat                                                                2766
```

<210> SEQ ID NO 38
<211> LENGTH: 922
<212> TYPE: PRT
<213> ORGANISM: Artificial Sequence
<220> FEATURE:
<223> OTHER INFORMATION: ERT2-DEVD-rtTA-3xFLAG-DEVD-ERT2 NT w/out GCA
      after flag

<400> SEQUENCE: 38

```
Ala Gly Asp Met Arg Ala Ala Asn Leu Trp Pro Ser Pro Leu Met Ile
1               5                  10                  15

Lys Arg Ser Lys Lys Asn Ser Leu Ala Leu Ser Leu Thr Ala Asp Gln
            20                  25                  30

Met Val Ser Ala Leu Leu Asp Ala Glu Pro Pro Ile Leu Tyr Ser Glu
        35                  40                  45

Tyr Asp Pro Thr Arg Pro Phe Ser Glu Ala Ser Met Met Gly Leu Leu
    50                  55                  60

Thr Asn Leu Ala Asp Arg Glu Leu Val His Met Ile Asn Trp Ala Lys
65                  70                  75                  80

Arg Val Pro Gly Phe Val Asp Leu Thr Leu His Asp Gln Val His Leu
                85                  90                  95

Leu Glu Cys Ala Trp Leu Glu Ile Leu Met Ile Gly Leu Val Trp Arg
            100                 105                 110

Ser Met Glu His Pro Val Lys Leu Leu Phe Ala Pro Asn Leu Leu Leu
        115                 120                 125

Asp Arg Asn Gln Gly Lys Cys Val Glu Gly Met Val Glu Ile Phe Asp
    130                 135                 140

Met Leu Leu Ala Thr Ser Ser Arg Phe Arg Met Met Asn Leu Gln Gly
145                 150                 155                 160

Glu Glu Phe Val Cys Leu Lys Ser Ile Ile Leu Leu Asn Ser Gly Val
                165                 170                 175

Tyr Thr Phe Leu Ser Ser Thr Leu Lys Ser Leu Glu Glu Lys Asp His
            180                 185                 190
```

-continued

```
Ile His Arg Val Leu Asp Lys Ile Thr Asp Thr Leu Ile His Leu Met
            195                 200                 205
Ala Lys Ala Gly Leu Thr Leu Gln Gln Gln His Gln Arg Leu Ala Gln
210                 215                 220
Leu Leu Leu Ile Leu Ser His Ile Arg His Met Ser Asn Lys Gly Met
225                 230                 235                 240
Glu His Leu Tyr Ser Met Lys Cys Lys Asn Val Val Pro Leu Tyr Asp
                245                 250                 255
Leu Leu Leu Glu Ala Ala Asp Ala His Arg Leu His Ala Pro Thr Ser
            260                 265                 270
Arg Gly Gly Ala Ser Val Glu Thr Asp Gln Ser His Leu Ala Thr
            275                 280                 285
Ala Gly Ser Thr Ser Ser His Ser Leu Gln Lys Tyr Tyr Ile Thr Gly
            290                 295                 300
Glu Ala Glu Gly Phe Pro Ala Thr Ala Val Asp Lys Arg Lys Gly Asp
305                 310                 315                 320
Glu Val Asp Gly Val Asp Glu Ser Arg Leu Asp Lys Ser Lys Val Ile
                325                 330                 335
Asn Gly Ala Leu Glu Leu Leu Asn Gly Val Gly Ile Glu Gly Leu Thr
            340                 345                 350
Thr Arg Lys Leu Ala Gln Lys Leu Gly Val Glu Gln Pro Thr Leu Tyr
            355                 360                 365
Trp His Val Lys Asn Lys Arg Ala Leu Leu Asp Ala Leu Pro Ile Glu
            370                 375                 380
Met Leu Asp Arg His His Thr His Phe Cys Pro Leu Glu Gly Glu Ser
385                 390                 395                 400
Trp Gln Asp Phe Leu Arg Asn Asn Ala Lys Ser Phe Arg Cys Ala Leu
                405                 410                 415
Leu Ser His Arg Asp Gly Ala Lys Val His Leu Gly Thr Arg Pro Thr
            420                 425                 430
Glu Lys Gln Tyr Glu Thr Leu Glu Asn Gln Leu Ala Phe Leu Cys Gln
            435                 440                 445
Gln Gly Phe Ser Leu Glu Asn Ala Leu Tyr Ala Leu Ser Ala Val Gly
            450                 455                 460
His Phe Thr Leu Gly Cys Val Leu Glu Glu Gln Glu His Gln Val Ala
465                 470                 475                 480
Lys Glu Glu Arg Glu Thr Pro Thr Thr Asp Ser Met Pro Pro Leu Leu
                485                 490                 495
Arg Gln Ala Ile Glu Leu Phe Asp Arg Gln Gly Ala Glu Pro Ala Phe
            500                 505                 510
Leu Phe Gly Leu Glu Leu Ile Ile Cys Gly Leu Glu Lys Gln Leu Lys
            515                 520                 525
Cys Glu Ser Gly Gly Pro Ala Asp Ala Leu Asp Asp Phe Asp Leu Asp
            530                 535                 540
Met Leu Pro Ala Asp Ala Leu Asp Asp Phe Asp Leu Asp Met Leu Pro
545                 550                 555                 560
Ala Asp Ala Leu Asp Asp Phe Asp Leu Asp Met Leu Pro Gly Asp Tyr
                565                 570                 575
Lys Asp His Asp Gly Asp Tyr Lys Asp His Asp Ile Asp Tyr Lys Asp
            580                 585                 590
Asp Asp Asp Lys Arg Lys Gly Asp Glu Val Asp Gly Val Asp Glu Ala
            595                 600                 605
```

Gly Asp Met Arg Ala Ala Asn Leu Trp Pro Ser Pro Leu Met Ile Lys
610                 615                 620

Arg Ser Lys Lys Asn Ser Leu Ala Leu Ser Leu Thr Ala Asp Gln Met
625                 630                 635                 640

Val Ser Ala Leu Leu Asp Ala Glu Pro Pro Ile Leu Tyr Ser Glu Tyr
                645                 650                 655

Asp Pro Thr Arg Pro Phe Ser Glu Ala Ser Met Met Gly Leu Leu Thr
            660                 665                 670

Asn Leu Ala Asp Arg Glu Leu Val His Met Ile Asn Trp Ala Lys Arg
        675                 680                 685

Val Pro Gly Phe Val Asp Leu Thr Leu His Asp Gln Val His Leu Leu
690                 695                 700

Glu Cys Ala Trp Leu Glu Ile Leu Met Ile Gly Leu Val Trp Arg Ser
705                 710                 715                 720

Met Glu His Pro Val Lys Leu Leu Phe Ala Pro Asn Leu Leu Leu Asp
                725                 730                 735

Arg Asn Gln Gly Lys Cys Val Glu Gly Met Val Glu Ile Phe Asp Met
            740                 745                 750

Leu Leu Ala Thr Ser Ser Arg Phe Arg Met Met Asn Leu Gln Gly Glu
        755                 760                 765

Glu Phe Val Cys Leu Lys Ser Ile Ile Leu Leu Asn Ser Gly Val Tyr
770                 775                 780

Thr Phe Leu Ser Ser Thr Leu Lys Ser Leu Glu Glu Lys Asp His Ile
785                 790                 795                 800

His Arg Val Leu Asp Lys Ile Thr Asp Thr Leu Ile His Leu Met Ala
                805                 810                 815

Lys Ala Gly Leu Thr Leu Gln Gln Gln His Gln Arg Leu Ala Gln Leu
            820                 825                 830

Leu Leu Ile Leu Ser His Ile Arg His Met Ser Asn Lys Gly Met Glu
        835                 840                 845

His Leu Tyr Ser Met Lys Cys Lys Asn Val Val Pro Leu Tyr Asp Leu
850                 855                 860

Leu Leu Glu Ala Ala Asp Ala His Arg Leu His Ala Pro Thr Ser Arg
865                 870                 875                 880

Gly Gly Ala Ser Val Glu Glu Thr Asp Gln Ser His Leu Ala Thr Ala
                885                 890                 895

Gly Ser Thr Ser Ser His Ser Leu Gln Lys Tyr Tyr Ile Thr Gly Glu
            900                 905                 910

Ala Glu Gly Phe Pro Ala Thr Ala Val Asp
        915                 920

<210> SEQ ID NO 39
<211> LENGTH: 1503
<212> TYPE: DNA
<213> ORGANISM: Artificial Sequence
<220> FEATURE:
<223> OTHER INFORMATION: MCD8-NES- DEVD-rtTA

<400> SEQUENCE: 39
atggcctcac cgttgacccg ctttctgtcg ctgaacctgc tgctgctggg tgagtcgatt      60
atcctgggga gtggagaagc taagccacag gcacccgaac tccgaatctt ccaaagaaa     120 atggacgccg aacttggtca gaaggtggac ctggtatgtg aagtgttggg gtccgtttcg     180
caaggatgct cttggctctt ccagaactcc agctccaaac tcccccagcc caccttcgtt     240
gtctatatgg cttcatccca caacaagata acgtgggacg agaagctgaa ttcgtcgaaa     300

```
ctgttttctg ccatgaggga cacgaataat aagtacgttc tcaccctgaa caagttcagc    360
aaggaaaacg aaggctacta tttctgctca gtcatcagca actcggtgat gtacttcagt    420
tctgtcgtgc cagtccttca gaaagtgaac tctactacta ccaagccagt gctgcgaact    480
ccctcacctg tgcaccctac cgggacatct cagccccaga gaccgaaaga ttgtcggccc    540
cgtggctcag tgaaggggac cggattggac ttcgcctgtg atatttacat ctgggcaccc    600
ttggccggaa tctgcgtggc ccttctgctg tccttgatca tcactctcat ctgctaccac    660
agccgcggat ctaacctggt ggacctccaa aagaagctgg aggagctgga gctggacgag    720
cagcagaaga ggaagggcga cgaggtggac ggcgtggacg agtctagact ggacaagagc    780
aaagtcataa acggcgctct ggaattactc aatggagtcg gtatcgaagg cctgacgaca    840
aggaaactcg ctcaaaagct gggagttgag cagcctaccc tgtactggca cgtgaagaac    900
aagcgggccc tgctcgatgc cctgccaatc gagatgctgg acaggcatca tacccacttc    960
tgccccctgg aaggcgagtc atggcaagac tttctgcgga caacgccaa gtcattccgc     1020 tgtgctctcc tctcacatcg cgacggggct aaagtgcatc tcggcacccg cccaacagag    1080
aaacagtacg aaaccctgga aaatcagctc gcgttcctgt gtcagcaagg cttctccctg    1140
gagaacgcac tgtacgctct gtccgccgtg ggccacttta cactgggctg cgtattggag    1200
gaacaggagc atcaagtagc aaaagaggaa agagagacac ctaccaccga ttctatgccc    1260
ccacttctga caagcaat tgagctgttc gaccggcagg gagccgaacc tgccttcctt      1320
ttcggcctgg aactaatcat atgtggcctg gagaaacagc taaagtgcga aagcggcggg    1380
ccggccgacg cccttgacga ttttgactta gacatgctcc cagccgatgc ccttgacgac    1440
tttgaccttg atatgctgcc tgctgacgct cttgacgatt tgaccttga catgctcccc     1500 ggg                                                                   1503
```

<210> SEQ ID NO 40
<211> LENGTH: 501
<212> TYPE: PRT
<213> ORGANISM: Artificial Sequence
<220> FEATURE:
<223> OTHER INFORMATION: MCD8-NES- DEVD-rtTA

<400> SEQUENCE: 40

```
Met Ala Ser Pro Leu Thr Arg Phe Leu Ser Leu Asn Leu Leu Leu Leu
1               5                   10                  15

Gly Glu Ser Ile Ile Leu Gly Ser Gly Glu Ala Lys Pro Gln Ala Pro
            20                  25                  30

Glu Leu Arg Ile Phe Pro Lys Lys Met Asp Ala Glu Leu Gly Gln Lys
        35                  40                  45

Val Asp Leu Val Cys Glu Val Leu Gly Ser Val Ser Gln Gly Cys Ser
    50                  55                  60

Trp Leu Phe Gln Asn Ser Ser Ser Lys Leu Pro Gln Pro Thr Phe Val
65                  70                  75                  80

Val Tyr Met Ala Ser Ser His Asn Lys Ile Thr Trp Asp Glu Lys Leu
                85                  90                  95

Asn Ser Ser Lys Leu Phe Ser Ala Met Arg Asp Thr Asn Asn Lys Tyr
            100                 105                 110

Val Leu Thr Leu Asn Lys Phe Ser Lys Glu Asn Glu Gly Tyr Tyr Phe
        115                 120                 125

Cys Ser Val Ile Ser Asn Ser Val Met Tyr Phe Ser Ser Val Val Pro
    130                 135                 140
```

Val Leu Gln Lys Val Asn Ser Thr Thr Thr Lys Pro Val Leu Arg Thr
145                 150                 155                 160

Pro Ser Pro Val His Pro Thr Gly Thr Ser Gln Pro Gln Arg Pro Glu
                165                 170                 175

Asp Cys Arg Pro Arg Gly Ser Val Lys Gly Thr Gly Leu Asp Phe Ala
            180                 185                 190

Cys Asp Ile Tyr Ile Trp Ala Pro Leu Ala Gly Ile Cys Val Ala Leu
        195                 200                 205

Leu Leu Ser Leu Ile Ile Thr Leu Ile Cys Tyr His Ser Arg Gly Ser
210                 215                 220

Asn Leu Val Asp Leu Gln Lys Lys Leu Glu Glu Leu Glu Leu Asp Glu
225                 230                 235                 240

Gln Gln Lys Arg Lys Gly Asp Glu Val Asp Gly Val Asp Glu Ser Arg
                245                 250                 255

Leu Asp Lys Ser Lys Val Ile Asn Gly Ala Leu Glu Leu Leu Asn Gly
            260                 265                 270

Val Gly Ile Glu Gly Leu Thr Thr Arg Lys Leu Ala Gln Lys Leu Gly
        275                 280                 285

Val Glu Gln Pro Thr Leu Tyr Trp His Val Lys Asn Lys Arg Ala Leu
290                 295                 300

Leu Asp Ala Leu Pro Ile Glu Met Leu Asp Arg His Thr His Phe
305                 310                 315                 320

Cys Pro Leu Glu Gly Glu Ser Trp Gln Asp Phe Leu Arg Asn Asn Ala
                325                 330                 335

Lys Ser Phe Arg Cys Ala Leu Leu Ser His Arg Asp Gly Ala Lys Val
            340                 345                 350

His Leu Gly Thr Arg Pro Thr Glu Lys Gln Tyr Glu Thr Leu Glu Asn
        355                 360                 365

Gln Leu Ala Phe Leu Cys Gln Gln Gly Phe Ser Leu Glu Asn Ala Leu
370                 375                 380

Tyr Ala Leu Ser Ala Val Gly His Phe Thr Leu Gly Cys Val Leu Glu
385                 390                 395                 400

Glu Gln Glu His Gln Val Ala Lys Glu Glu Arg Glu Thr Pro Thr Thr
                405                 410                 415

Asp Ser Met Pro Pro Leu Leu Arg Gln Ala Ile Glu Leu Phe Asp Arg
            420                 425                 430

Gln Gly Ala Glu Pro Ala Phe Leu Phe Gly Leu Glu Leu Ile Ile Cys
        435                 440                 445

Gly Leu Glu Lys Gln Leu Lys Cys Glu Ser Gly Gly Pro Ala Asp Ala
450                 455                 460

Leu Asp Asp Phe Asp Leu Asp Met Leu Pro Ala Asp Ala Leu Asp Asp
465                 470                 475                 480

Phe Asp Leu Asp Met Leu Pro Ala Asp Ala Leu Asp Asp Phe Asp Leu
                485                 490                 495

Asp Met Leu Pro Gly
            500

<210> SEQ ID NO 41
<211> LENGTH: 204
<212> TYPE: DNA
<213> ORGANISM: Artificial Sequence
<220> FEATURE:
<223> OTHER INFORMATION: Mito-CAVP (N-terminal end of SMAC)

<400> SEQUENCE: 41

```
atggcggctc tgaagagttg gctgtcgccc atcgtaactt cattcttcag gtacagacag      60
tgtttgtgtg ttcctgttgt ggctaacttt aagaagcggt gtttctcaga attgataaga     120
ccatggcaca aaactgtgac gattggcttt ggagtaaccc tgtgtgcggt tcctattgca     180
cagaaatcag agcctcattc cctt                                            204
```

<210> SEQ ID NO 42
<211> LENGTH: 68
<212> TYPE: PRT
<213> ORGANISM: Artificial Sequence
<220> FEATURE:
<223> OTHER INFORMATION: Mito-CAVP (N-terminal end of SMAC)

<400> SEQUENCE: 42

```
Met Ala Ala Leu Lys Ser Trp Leu Ser Arg Ser Val Thr Ser Phe Phe
 1               5                  10                  15
Arg Tyr Arg Gln Cys Leu Cys Val Pro Val Val Ala Asn Phe Lys Lys
            20                  25                  30
Arg Cys Phe Ser Glu Leu Ile Arg Pro Trp His Lys Thr Val Thr Ile
        35                  40                  45
Gly Phe Gly Val Thr Leu Cys Ala Val Pro Ile Ala Gln Ala Val Tyr
    50                  55                  60
Thr Leu Thr Ser
65
```

<210> SEQ ID NO 43
<211> LENGTH: 705
<212> TYPE: DNA
<213> ORGANISM: Artificial Sequence
<220> FEATURE:
<223> OTHER INFORMATION: Gal4-VP16 transactivator

<400> SEQUENCE: 43

```
atgaagctac tgtcttctat cgaacaagca tgcgatattt gccgacttaa aaagctcaag      60
tgctccaaag aaaaaccgaa gtgcgccaag tgtctgaaga acaactggga gtgtcgctac     120
tctcccaaaa ccaaaaggtc tccgctgact agggcacatc tgacagaagt ggaatcaagg     180
ctagaaaagac tggaacagct atttctactg attttttcctc gagaagacct tgacatgatt     240
ttgaaaatgg attctttaca ggatataaaa gcattgttaa caggattatt tgtacaagat     300
aatgtgaata agatgccgt cacagataga ttggcttcag tggagactga tatgcctcta     360
acattgagac agcatagaat aagtgcgaca tcatcatcgg aagagagtag taacaaaggt     420
caaagacagt tgactgtatc gatgggccct aaaaagaagc gtaaagtcgc cccccgacc     480
gatgtcagcc tgggggacga gctccactta gacggcgagg acgtggcgat ggcgcatgcc     540
gacgcgctag acgatttcga tctggacatg ttggggacg gggattcccc gggtccggga     600
tttaccccc cgactccgc ccctacggc gctctggata tggccgactt cgagtttgag     660
cagatgttta ccgatgccct tggaattgac gagtacggtg ggtag                    705
```

<210> SEQ ID NO 44
<211> LENGTH: 1272
<212> TYPE: DNA
<213> ORGANISM: Artificial Sequence
<220> FEATURE:
<223> OTHER INFORMATION: FLPo recombinase

<400> SEQUENCE: 44

```
atgagccagt tcgacatcct gtgcaagacc cccccaagg tgctggtgcg gcagttcgtg      60
gagagattcg agaggcccag cggcgagaag atcgccagct gtgccgccga gctgacctac    120
ctgtgctgga tgatcaccca aacggcacc gccatcaaga gggccacctt catgagctac    180
aacaccatca tcagcaacag cctgagcttc gacatcgtga acaagagcct gcagttcaag    240
tacaagaccc agaaggccac catcctggag gccagcctga agaagctgat ccccgcctgg    300
gagttcacca tcatcccctta aacggccag aagcaccaga gcgacatcac cgacatcgtg    360
tccagcctgc agctgcagtt cgagagcagc gaggaggccg acaagggcaa cagccacagc    420
aagaagatgc tgaaggccct gctgtccgag ggcgagagca tctgggagat caccgagaag    480
atcctgaaca gcttcgagta caccagcagg ttcaccaaga ccaagaccct gtaccagttc    540
ctgttcctgg ccacattcat caactgcggc aggttcagcg acatcaagaa cgtggacccc    600
aagagcttca gctggtgca gaacaagtac ctgggcgtga tcattcagtg cctggtgacc    660
gagaccaaga caagcgtgtc caggcacatc tacttttttca gcgccagagg caggatcgac    720
cccctggtgt acctggacga gttcctgagg aacagcgagc ccgtgctgaa gagagtgaac    780
aggaccggca acagcagcag caacaagcag gagtaccagc tgctgaagga caacctggtg    840
cgcagctaca caaggccct gaagaagaac gcccccctacc ccatcttcgc tatcaagaac    900
ggccctaaga gccacatcgg caggcacctg atgaccagct ttctgagcat gaagggcctg    960
accgagctga caaacgtggt gggcaactgg agcgacaaga gggcctccgc cgtggccagg   1020
accacctaca cccaccagat caccgccatc cccgaccact acttcgccct ggtgtccagg   1080
tactacgcct acgaccccat cagcaaggag atgatcgccc tgaaggacga gaccaacccc   1140
atcgaggagt ggcagcacat cgagcagctg aagggcagcg ccgagggcag catcagatac   1200
cccgcctgga acggcatcat cagccaggag gtgctggact acctgagcag ctacatcaac   1260
aggcggatct aa                                                       1272
```

<210> SEQ ID NO 45
<211> LENGTH: 1041
<212> TYPE: DNA
<213> ORGANISM: Artificial Sequence
<220> FEATURE:
<223> OTHER INFORMATION: Cre recobminase

<400> SEQUENCE: 45

```
atgaatttac tgaccgtaca ccaaaatttg cctgcattac cggtcgatgc aacgagtgat     60
gaggttcgca agaacctgat ggacatgttc agggatcgcc aggcgttttc tgagcatacc    120
tggaaaatgc ttctgtccgt ttgccggtcg tgggcggcat ggtgcaagtt gaataaccgg    180
aaatggtttc ccgcagaacc tgaagatgtt cgcgattatc ttctatatct tcaggcgcgc    240
ggtctggcag taaaaactat ccagcaacat ttgggccagc taaacatgct tcatcgtcgg    300
tccgggctgc cacgaccaag tgacagcaat gctgtttcac tggttatgcg gcggatccga    360
aaagaaaacg ttgatgccgg tgaacgtgca aaacaggctc tagcgttcga acgcactgat    420
ttcgaccagg ttcgttcact catggaaaat agcgatcgct gccaggatat acgtaatctg    480
gcatttctgg ggattgctta taacaccctg ttacgtatag ccgaaattgc caggatcagg    540
gttaaagata tctcacgtac tgacggtggg agaatgttaa tccatattgg cagaacgaaa    600
acgctggtta gcaccgcagg tgtagagaag gcacttagcc tggggtaac taaactggtc    660
```

```
gagcgatgga tttccgtctc tggtgtagct gatgatccga ataactacct gttttgccgg    720
gtcagaaaaa atggtgttgc cgcgccatct gccaccagcc agctatcaac tcgcgccctg    780
gaagggattt ttgaagcaac tcatcgattg atttacggcg ctaaggatga ctctggtcag    840
agatacctgg cctggtctgg acacagtgcc cgtgtcggag ccgcgcgaga tatggcccgc    900
gctggagttt caataccgga gatcatgcaa gctggtggct ggaccaatgt aaatattgtc    960
atgaactata tccgtaacct ggatagtgaa acaggggcaa tggtgcgcct gctggaagat   1020
ggcgatctcg agccatctta a                                             1041
```

<210> SEQ ID NO 46
<211> LENGTH: 7
<212> TYPE: PRT
<213> ORGANISM: Artificial Sequence
<220> FEATURE:
<223> OTHER INFORMATION: Caspase-sensitive
<220> FEATURE:
<221> NAME/KEY: MISC_FEATURE
<222> LOCATION: (4)..(4)
<223> OTHER INFORMATION: X means D or A

<400> SEQUENCE: 46

Asp Gln Val Xaa Ala Gly Val
1               5

<210> SEQ ID NO 47
<211> LENGTH: 4
<212> TYPE: PRT
<213> ORGANISM: Artificial Sequence
<220> FEATURE:
<223> OTHER INFORMATION: Caspase-insensitive

<400> SEQUENCE: 47

Arg Ile Cys Gly
1

ANASTASIS BIOSENSOR CASPASE TRACKER

CROSS-REFERENCE TO RELATED APPLICATIONS

This application is a 35 U.S.C. § 371 U.S. national entry of International Application PCT/US2018/061428, having an international filing date of Nov. 16, 2018, which claims the benefit of U.S. Provisional Application No. 62/587,201, filed Nov. 16, 2017, the contents of each of the aforementioned applications are herein incorporated by reference in their entireties.

FIELD OF THE INVENTION

The present invention relates to the field of anastasis, i.e., the process of reversal of apoptosis. More specifically, the present invention provides methods and compositions useful for studying anastasis.

INCORPORATION-BY-REFERENCE OF MATERIAL SUBMITTED ELECTRONICALLY

This application contains a sequence listing. It has been submitted electronically via EFS-Web as an ASCII text file entitled "P15014-03_ST25.txt." The sequence listing is 100,530 bytes in size, and was created on Nov. 17, 2022. It is hereby incorporated by reference in its entirety.

BACKGROUND OF THE INVENTION

Programmed cell death such as apoptosis plays essential role in embryonic development and normal hemostasis by eliminating unwanted, injured, or dangerous cells in multicellular organisms. See Fuchs, Y & Steller, H., 147 CELL 742-58 (2011); Jacobson et al, 88 CELL 347-54 (1997); and Kerr et al., 26 BR. J. CANCER 239-57 (1972). The loss of balance between cell death and survival is fatal consequences such as cancer, heart failure, autoimmunity, and degeneration. See Hanahan, D. & Weinberg, R. A., 144 CELL 646-74 (2011); Nagata, S., 1209 ANN. N.Y. ACAD. SCI. 10-16 (2010); Mattson, M. P., 1 NAT. REV. MOL. CELL. BIOL. 120-29 (2000); and Narula et al., 3335 N. ENGL. J. MED. 1182-89 (1996). Activation of executioner caspases has traditionally been considered as the "point of no return" in apoptosis (Riedl, S. J. & Shi, Y, 5 NAT. REV. MOL. CELL. BIOL. 897-907 (2004); Green, D. & Kroemer, G., 8 TRENDS CELL. BIOL. 267-71 (1998)), as it triggers rapid and massive cellular demolition (Chipuk et al., 37 MOL. CELL. 299-310 (2010); Taylor et al., 9 NAT. REV. MOL. CELL. BIOL. 231-41 (2008); Luthi, A. U. & Martin, S. J., 14 CELL DEATH DIFFER. 641-50 (2007); and Takemoto et al., 160 J. CELL. BIOL. 235-43 (2003)). Challenging this general dogma, we demonstrated that dying primary cells and cancer cells can recovery no only after caspase activation, but also important cell death events including plasma membrane blebbing, cell shrinkage, mitochondrial fragmentation, release of mitochondrial cytochrome c into the cytosol, nuclear and chromatin condensation, DNA damage, nuclear fragmentation, cell surface exposure of phosphatidylserine (PS), and formation of apoptotic bodies. See Tang et al., 43 F1000RES. 43 (2017); Tang et al., 96 J. VIS. EXP. 51964 (2015); Tang et al., 5 SCI. REP. 9015 (2015); Tang et al., 23 MOL. BIOL. CELL 2240-52 (2012); and Tang et al., 100 BR. J. CANCER 118-22 (2009). We propose that anastasis is an intrinsic cell recovery phenomenon, as dying cells can recover after removal of cell death stimuli. Our observation on reversal of cell death process is further supported by independent studies that also reveal recovery of cell after phosphatidylserine externalization (Kenis et al, 51 J. NUCL. MED. 259-67 (2010); Geske et al., 8 CELL DEATH DIFFER. 182-91 (2001); and Hammill et al., 251 EXP. CELL. RES. 16-21 (1999)), cytochrome c release (Ichim et al., 57 MOL. CELL 860-72 (2015)), activation of mixed lineage kinase-like (MLKL) and cell shrinkage (Gong et al., 169 CELL 286-300 E16 (2017)). We coined the term "Anastasis" (Αναστά σης) (Tang et al. (2012)), which means "rising to life" in Greek, to describe this unexpected cell recovery phenomenon.

The discovery of anastasis leads to paradigm-shifting physiological, pathological, and therapeutic implications. Anastasis could represent a previously unknown cytoprotective mechanism to rescue and preserve important cells and tissues that are difficult to be replaced (Tang et al. (2012)), thereby underlying the observation on heart failure reversal by ventricular unloading with left ventricular assist devices (LVADs) (Drakos et al., 126 CIRCULATION 230-41 (2012); Narula et al., 3 NAT. CLIN. PRACT. CARDIOVASC. MED. 681-88 (2006)), recovery of photoreceptor cells after transient exposure of excessive light (Gordon et al., 43 INVEST. OPHTHALMOL. VIS. SCI. 3511-21 (2002); Milligan et al., 139 J. CELL. BIOL. 351-63 (1997); McKechnie, N. M. & Foulds, W. S., 212 ALBRECHT VON GRAEFES ARCH. KLIN. EXP. OPHTHALMOL. 271-83 (1980)), repair of neurons after brain injury (Blennow et al., 2 NAT. REV. DIS. PRIMERS 16084 (2016)). If so promoting anastasis could enhance tissue recovery. Anastasis could be an unexpected escape tactic used by cancer cells to survive cell-death-inducing cancer therapy, causing cancer recurrence (Tang et al. (2009)). Therefore, suppressing anastasis in dying cancer cells during and after cancer treatment could be a novel therapeutic strategy to cure cancers by inhibiting cancer relapse. Interestingly, we found that some recovered cells acquired permanent genetic alterations and underwent oncogenic transformation, possibly by rescuing the cells that had experienced DNA damage during apoptosis (Tang et al. (2017); Tang et al. (2015); Tang et al. (2012)). Thus, anastasis could be a tumorigenic mechanism as it rescues DNA damaged cells, underlying the observations that repeated tissue injury increases the risk of cancers in a variety of tissues, such as chronic thermal injury in the esophagus induced by the consumption of very hot beverages (Loomis et al., 17 LANCET ONCOL. 877-78 (2016); Islami et al., 338 BMJ b929 (2009); Castellsague et al., 88 INT. J. CANCER 658-64 (2000)), liver damage due to alcoholism (Boffetta, P. & Hashibe, M., 7 LANCET ONCOL. 149-56 (2006); McKillop, I. H. & Schrum, L. W., 35 ALCOHOL 195-203 (2005)), tumor evolution after genotoxic cancer therapy (Wagle et al., 29 J. CLIN. ONCOL. 3085-96 (2011); Demedts et al., 35 EUR. RESPIR. J. 202-15 (2010); Davis, A. J. & Tannock, J. F., 1 LANCET ONCOL. 86-93 (2000)) and development of second (new) cancers from normal tissues during the intervals between cycles of cancer therapy (Chaturvedi et al., 99 J. NATL. CANCER INST. 1634-43 (2007); Travis et al., 97 J. NATL. CANCER INST. 1354-65 (2005); Smith et al., 21 J. CLIN. ONCOL. 1195-1204 (2003)). If true targeting anastasis could prevent or arrest cancer development and progression.

To harness the discovery of anastasis to develop revolutionary new therapies, it is essential to study the cause and consequence of anastasis in live animals. However, it is technically challenging to identify anastatic cells in vivo, because the cells that recovered from cell death process appear morphologically indistinguishable from normal healthy cells, and there is no biomarker of anastasis (Tang et al. (2017); Tang et al. (2015); Tang et al. (2012)). To address these problems, we recently developed a new in vivo caspase biosensor designated "CaspaseTracker" (Tang et al., 5 SCI. REP. 9015 (2015)), to identify and track cells that survive apoptosis after caspase activation (Ding et al., 5 ELIFE (2016); Tang et al., 5 SCI. REP. 9015 (2015)), the hallmark of apoptosis (Taylor et al. (2008); Riedl et al. (2004)). Different from the "real-time" caspase biosensors such as SCAT (Takemoto et al., 104 PROC. NATL. ACAD. SCI. U.S.A. 13367-72 (2007); Takemoto et al. (2003)), Apoliner (Bardet et al., 105 PROC. NATL. ACAD. SCI. U.S.A. 13901-95 (2008)), CA-GFP (Nicholls et al., 286 J. BIOL. CHEM. 24977-86 (2011)), ApoAlert (Tang et al. (2012); Golbs et al., 21 CEREB. CORTEX 1192-1201 (2011)), C3AIs (Zhang et al., 4 NAT. COMMUN. 2157 (2013)) and iCasper (To et al., 112 PROC. NATL. ACAD. SCI. U.S.A. 3338-43 (2015)) that detect the on-going caspase activity, the CaspaseTracker biosensor can further permanently label the cells that have ever experienced caspase activity. Therefore, the CaspaseTracker biosensor provides long term tracking of anastasis after reversal of caspase-mediated cell death process in vivo.

BRIEF DESCRIPTION OF THE FIGURES

FIG. 1A—Schematic diagram of the approach to induce cell death and subsequently allow dying cells to recover after removal of cell death inducer. FIG. 1B—Time-lapse live cell DIC microscopy of healthy HeLa cells (i), the same group of cells that were treated with 1 μM staurosporine (ii), and then washed and further inducible with fresh culture medium (iii-vi). White arrow indicates the dividing cell. FIG. 1C—Schematic diagram of caspase biosensor fusion protein NES-DEVD-YFP-NLS, for the subcellular localization of YFP during apoptosis and after anastasis. FIG. 1D—Time-lapse live cell confocal microscopy of HeLa cell expressing caspase biosensor fusion protein NES-DEVD-YFP-NLS before (i), during (ii-iii) and after (iv-viii) exposure to 3.7% ethanol in cell culture medium. Confocal images of the caspase biosensor (green, top panel); Merged images of Hoechst-stained nucleus (blue) and mitochondria (red) (middle panel), and further merged with DIC images (bottom panel). White arrows indicate the caspase activated, nuclear localized YFP biosensor signal.

FIG. 2A-2E. Mammalian CaspaseTracker biosensor system. FIG. 2A—Schematic diagram of the mammalian CaspaseTracker rtTA biosensor system. FIG. 2B—Schematic diagram of the caspase-sensitive rtTA. FIG. 2C—Flow chart of using the CaspaseTracker rtTA biosensor system to detect anastasis. FIG. 2D—Time-lapse live cell confocal microscopy of HeLa cell expressing the mammalian CaspaseTracker rtTA biosensor before (i), during (ii-iii) and after (iv-vii) exposure to 1 μM staurosporine in cell culture medium. Merged images of DIC and DsRed signals. FIG. 2E—Time-lapse live cell confocal microscopy of the untreated biosensor-expressing HeLa cells. Cells were incubated with 1 ug/ml doxycycline throughout the experiments of (D) and (E).

FIG. 3A-3J. Drosophila CaspaseTracker dual biosensor system (reprinted with permission from Tang et al., 9 SCIENTIFIC REPORTS 9015 (2015)). FIG. 3A—Schematic diagram of the Drosophila CaspaseTracker Gal4 biosensor system. FIG. 3B—Schematic diagram of the caspase-sensitive (DQVD) and caspase-insensitive control (DQVA) Ga14. FIG. 3C—Schematic of Drosophila ovary, and flow chart for cell death-induction in 1-day-old flies, followed by 3-days recovery at normal condition. Drosophila ovary drawing provided by Polan Santos; Drosophila image Darren Obbard. FIG. 3D—Representative confocal image of egg chambers from the ovary of female biosensor flies fed with normal fly food for 6 days (untreated). FIG. 3E—Representative confocal image of egg chambers from the ovary of cold shocked female biosensor flies were placed at −7° C. for 1 hour and then switched to normal condition for 1 day (Cold Shock). FIG. 3F—Like panel E except the cold shocked flies were switched to normal condition for 3 days (CS Recovered). FIG. 3G—Representative confocal image of egg chambers from the ovary of starved female biosensor flies fed with 8% sucrose in 1% agar without protein for 3 days to induce apoptosis in egg chambers (Starved). FIG. 3H—Like panel G except the treated flies were switched to normal fly food for 3 days after protein starvation treatment (Re-fed). FIG. 3I—Like panel E except the cold shock of caspase insensitive CaspaseTracker DQVA female biosensor, which served as negative control. FIG. 3J—Confocal image of egg chambers from starved and re-fed female Drosophila. Arrows indicate nuclear GFP expressing in the nurse cells (black), oocyte (white) and follicle cells (yellow) of egg chambers, and in the germarium (green).

DETAILED DESCRIPTION OF THE INVENTION

Figure 1A:
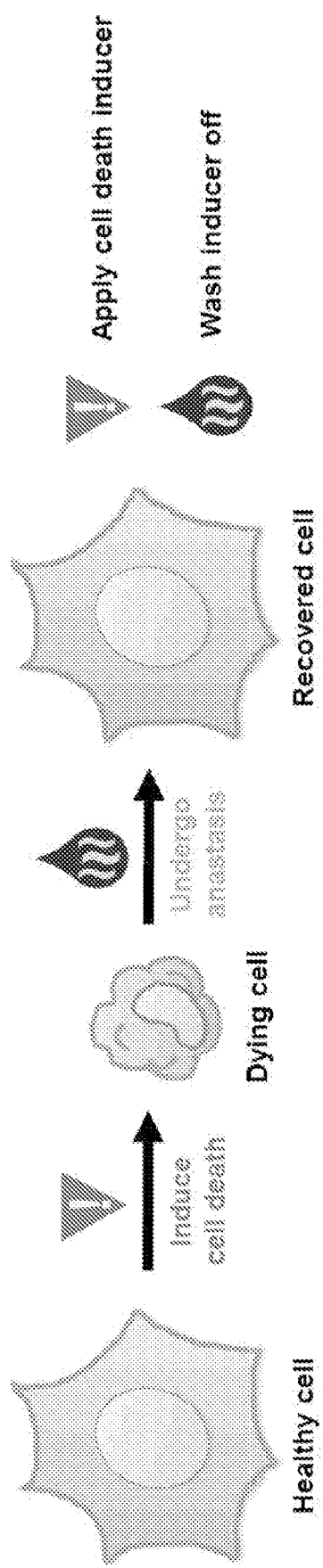
FIG. 1A-1D. Recovery of HeLa cells after cell death induction.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Anastasis (Greek for "rising to life") is a recently discovered cell recovery phenomenon whereby dying cells can reverse late-stage cell death processes that are generally assumed to be intrinsically irreversible. Promoting anastasis could in principle rescue or preserve injured cells that are difficult to replace such as cardiomyocytes in heart failure or neurons in brain injury, thereby facilitating tissue recovery. Conversely, suppressing anastasis in dying cancer cells, undergoing apoptosis due to anti-cancer therapies, may promote cancer cell death and reduce the chances of recurrence. However, these studies have been hampered by the lack of tools for tracking the fate of cells that undergo anastasis in live animals. The challenge is to identify and verify that the cells have reversed cell death process despite their morphologically normal appearance after recovery. To overcome this difficulty, we have generated the *Drosophila* and mammalian CaspaseTracker biosensor systems that can identify and permanently track the anastatic cells in vitro or in vivo. Here, we present in vivo protocols for the generation and use of this newly developed CaspaseTracker dual biosensor systems to detect and track anastasis in *Drosophila melanogaster* after transient exposure to cell death stimuli. Unlike conventional biosensors and protocols that label cells actively undergoing apoptotic cell death process, the biosensor permanently labels cells that have recovered after caspase activation, a hallmark of late-stage apoptosis. Therefore, this protocol enables us to continuously track the fate of these cells and their progeny, facilitating future studies of the biological functions, molecular mechanisms, physiological and pathological consequences, and therapeutic implications of anastasis. We also discuss the appropriate controls to distinguish cells that undergo anastasis from those that display non-apoptotic caspase activity in vivo.

As used herein, the term "polynucleotide" or "nucleic acid" refers to a polymeric form of nucleotides of any length, either ribonucleotides and/or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate ($P-NH_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

The term "promoter" refers to the DNA region, usually upstream of the coding sequence of a gene or operon, which binds RNA polymerase and directs the enzyme to the correct transcriptional start site.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors," which comprise the attributes of more than one type of vector A "site-specific recombination event" refers to an event catalyzed by a system generally consisting of three elements: a pair of DNA sequences (the site-specific recombination sequences or sites) and a specific enzyme (the site-specific recombinase). The site-specific recombinase catalyzes a recombination reaction only between two site-specific recombination sequences depending on the orientation of the site-specific recombination sequences. Sequences intervening between two site-specific recombination sites will be inverted in the presence of the site-specific recombinase when the site-specific recombination sequences are oriented in opposite directions relative to one another (i.e., inverted repeats). If the site-specific recombination sequences are oriented in the same direction relative to one another (i.e., direct repeats), then any intervening sequences will be deleted upon interaction with the site-specific recombinase. Thus, if the site-specific recombination sequences are present as direct repeats at both ends of vector backbone sequences integrated into a eukaryotic genome, such integration of said sequences can subsequently be removed by interaction of the site-specific recombination sequences with the corresponding site specific recombinase.

A number of different site specific recombinase systems can be used including, but not limited to, the Cre/lox system of bacteriophage P1, the FLP/FRT system of yeast, the Gin recombinase of phage Mu, the Pin recombinase of *E. coli*, the PinB, PinD and PinF from Shigella, and the R/RS system of Zygosaccharomyces rouxii. Recombinases generally are integrases, resolvases or flippases. Also dual-specific recombinases can be used in conjunction with direct or indirect repeats of two different site-specific recombination sites corresponding to the dual-specific recombinase (WO99/25840). In certain embodiments, site-specific recombinase systems are the bacteriophage P1 Cre/lox and the yeast FLP/FRT and the Z. rouxii R/RS systems. In these systems a recombinase (Cre, FLP or R, respectively) interact specifically with its respective site-specific recombination sequence (lox, FRT or RS respectively) to invert or excise the intervening sequences. The site-specific recombination sequences for each of these two systems are relatively short (34 bp for lox and 47 bp for FRT).

Accordingly, in one aspect, the present invention provides anastasis biosensor constructs. In one embodiment, a construct comprises the nucleotide sequence of SEQ ID NO:1. In another embodiment, a construct comprises the nucleotide sequence of SEQ ID NO:3. In yet another embodiment, a construct comprises the nucleotide sequence of SEQ ID NO:27. Alternatively, a construct can comprise the nucleotide sequence of SEQ ID NO:29. In a specific embodiment, a construct comprises the nucleotide sequence of SEQ ID NO:31. In another embodiment, a construct comprises the nucleotide sequence of SEQ ID NO:33. A construct can also comprise the nucleotide sequence of SEQ ID NO:35. In a further embodiment, a construct comprises the nucleotide sequence of SEQ ID NO:37. In yet a further embodiment, a construct comprises the nucleotide sequence of SEQ ID NO:39.

Alternatively, a construct of the present invention can comprise the amino acid of SEQ ID NO:2. In another embodiment, a construct comprises the amino acid sequence of SEQ ID NO:4. In yet another embodiment, a construct comprises the amino acid sequence of SEQ ID NO:28. Alternatively, a construct can comprise the amino acid sequence of SEQ ID NO:30. In a specific embodiment, a construct comprises the amino acid sequence of SEQ ID NO:32. In another embodiment, a construct comprises the amino acid sequence of SEQ ID NO:34. A construct can also comprise the amino acid sequence of SEQ ID NO:36. In a further embodiment, a construct comprises the amino acid sequence of SEQ ID NO:38. In yet a further embodiment, a construct comprises the amino acid sequence of SEQ ID NO:40. The constructs can comprise a conservative substitution of up to 1, 2, 3, 4, 5, 6, 7, 8, 9, 10, 11, 12, 13, 14, 15, 16, 17, 18, 19, 20, 25, 30, 35, 40, 45, 50, 55, 60, 65, 70 or more amino acids. In particular embodiments, the constructs comprise a conservative substitution of up to 1-25 amino acids.

Alternatively, a tracking construct of the present invention can comprise Lyn11-NES-ERT2-DEVD-rtTA-3xFLAG-DEVD-ERT2-NES. In another embodiment, the construct comprises the following elements: Lyn11-NES-ERT2-DEVD-rtTA. In yet another embodiment, the construct comprises Lyn11-NES-DEVD-rtTA. The construct can also comprise Lyn11-NES-ERT2-DEVD-rtTA-3xFLAG. In a specific embodiment, a construct comprises Lyn11-NES-DEVD-rtTA-3xFLAG. In yet another embodiment, a construct comprises MCD8-NES-DEVD-rtTA. In a further embodiment, a construct comprises ERT2-DEVD-rtTA-3XFLAG-DEVD-ERT2.

In certain embodiments, the present invention utilizes a split transcription factor/transactivator, for example, split rtTA. The split system would only be activated when both mitochondrial outer membrane permeabilization and caspase-3 activation occurs. For example, the N-terminal end of a transactivator like rtTA can be brought to the mitochondrial intermembrane space using a mitochondrial targeting sequence. In one embodiment, a MTS comprises Mito-CAVP (SEQ ID NO:40 (nucleotide) or 41 (amino acid)). A construct described herein can comprise the C-terminal end of rtTA. When apoptosis occurs, the functional transactivator is formed and the reporter system is activated. Thus, in certain embodiments, a construct of the present invention comprises a first half of a split transactivator and another construct comprises the second half of the transactivator coupled with a MTS.

Examples of the split approach include Split Gal4 (Refined spatial manipulation of neuronal function by combinatorial restriction of transgene expression., Neuron. 2006 52(3) 425-36, Luan H, Peabody N C, Vinson C R, White B H), Split Q (Controlling gene expression with the Q repressible binary expression system in Caenorhabditis elegans., Nat Methods. 2012 9(4) 391-5, Wei X, Potter C J, Luo L, Shen K), Split Cre (Split-CreERT2: temporal control of DNA recombination mediated by split-Cre protein fragment complementation, PLoS One. 2009 Dec 16; 4(12):e8354, Hirrlinger J, Requardt R P, Winkler U, Wilhelm F, Schulze C, Hirrlinger P G), Split FLPase (Reconstruction of Split-recombinase FLP and Its Recombination Activation in Transgenic Tobacco; Sequential gene targeting to make chimeric tumor models with de novo chromosomal abnormalities., Cancer Res. 2014 74(5) 1588-97, Chambers J S, Tanaka T, Brend T, Ali H, Geisler N J, Khazin L, Cigudosa J C, Dear T N, MacLennan K, Rabbitts T H), and Split Intein (Intersectional Cre driver lines generated using split-intein mediated split-Cre reconstitution., Sci Rep. 2012 2 497, Wang P, Chen T, Sakurai K, Han B X, He Z, Feng G, Wang F.).

In particular embodiments, sensitivity of the biosensor can be increased by increasing the copy number of the caspase cleavage sequence in the linker peptide. In other embodiments, the sensitivity of the biosensor can be adjusted, up or down, by fusing the biosensor with a mutant estrogen ligand-binding domain (ERT2)65 or expressing the biosensor using a tetracycline-responsive promoter66, so that the expression level (sensitivity) of the biosensor will depend on the concentration of tamoxifen or tetracycline, respectively. In further embodiments, the sensitivity of the biosensor can be lowered by using other DEVD-containing linker peptides that are less cleavable then the PARP domain-based linker (Poreba et al., 5 COLD SPRING HARB. PERSPECT. BIOL. A008680 (2013), Takemoto et al., 160 J. CELL BIOL. 235-43 (2003), and Talanian et al., 272 J. BIOL. CHEM. 9677-82 (1997).

Thus, in certain embodiments, a biosensor of the present invention comprises at least one construct described herein and a reporter system. A reporter system can comprise (1) a first nucleic acid encoding flippase operably linked to the upstream activating sequence that binds the transactivator; and (2) a second nucleic acid comprising an FRT-flanked stop codon cassette separating a constitutive promoter and a fluorescent protein open reading frame. The fluorescent protein comprises green fluorescent protein, red fluorescent protein, or yellow fluorescent protein. In other embodiments, the reporter system comprises the G-TRACE reporter system. In further embodiments, the transactivator can comprise a recombinase. In such embodiments, the reporter system can comprise a nucleic acid encoding a reporter gene operably linked to a promoter, wherein the recognition target sequence of the recombinase flanks a stop codon cassette located between the reporter gene and the promoter. In other embodiments, a reporter system comprises (1) a first nucleic acid encoding a site specific recombinase operably linked to the site specific sequence for the transcription factor; and (2) a second nucleic acid comprising a stop codon cassette flanked by site specific recombination sequences, wherein the stop codon cassette and flanking sequences separate a constitutive promoter and a fluorescent protein open reading frame.

The transactivators can comprise a transcription factor such as Gal4 or Q, a recombinase such as Cre, FLP or FLPo, or an intein (including split versions of the foregoing). See International Patent Application No. PCT/US2017/061973, incorporated by reference herein.

In particular embodiments, the biosensor of the present invention can also comprise a transient reporter in the nucleus. For example, the dual biosensor of the Caspase-Tracker (Tang et al., 5 SCI. REP. 9015 (2015) (see FIG. 1 of Tang et al.)) can be used to signal ongoing or transient, as well as permanent reporter expression. Thus, a biosensor can comprise a construct described herein and a reporter system comprising a transient reporter and a permanent reporter. See FIG. 3A. In certain embodiments, a system can comprise a biosensor described herein, a reporter system as well as a control as described in FIG. 3B.

In particular embodiments, rtTA is replaced by another non-mammalian transcription factor or transactivator. In one embodiment, a construct comprises the following elements: Lyn11-NES-ERT2-DEVD-transactivator-3xFLAG-DEVD-ERT2-NES. In another embodiment, the construct comprises the following elements: Lyn11-NES-ERT2-DEVD-transactivator. In yet another embodiment, the construct comprises Lyn11-NES-DEVD-transactivator. The construct can also comprise Lyn11-NES-ERT2-DEVD-transactivator-3xFLAG. In a specific embodiment, a construct comprises Lyn11-NES-DEVD-transactivator-3xFLAG. In yet another embodiment, a construct comprises MCD8-NES-DEVD-transactivator. In a further embodiment, a construct comprises ERT2-DEVD-transactivator-3XFLAG-DEVD-ERT2.

A construct of the present invention can comprise a transactivator and one or more of the following: a transmembrane domain (TD), a nuclear exclusion signal, ERT2, caspase cleavable linker, and purification tag (e.g., FLAG, 3x FLAG, HIS, 6XHIS).

The present invention also provides methods for using the biosensors and reporting systems described herein. Such methods can include methods for studying anastasis and are described in the Examples section below.

In further embodiments, the biosensors of the present invention can be used for drug screening. In certain embodiments, the biosensors can be expressed in organoids from a patient. Drugs that kill cancer cells without anastasis can be screened. If the biosensor indicates that anastasis is occurring or likely to occur, then other drugs can be used or an anastasis inhibitor could also be used to prevent cancer recurrence during and after drug treatment. In alternative embodiments, the screening can take place using patient-derived xenograft mice. See, e.g., Pauli et al., 7(5) CANCER DISCOV. 462-77 (2017).

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Anastasis is technically challenging to be detected in vivo because the cells that have reversed cell death process can be morphologically indistinguishable from the normal healthy cells. Here we demonstrate protocols for detecting and tracking cells that undergo anastasis in live animals using our newly developed in vivo CaspaseTracker dual biosensor systems.

Protocol

1) Preparation of CaspaseTracker Biosensor Flies
1.1. Anesthetize flies with $CO_2$, and use a paintbrush to transfer 7 to 10 caspase-sensitive Gal4 (DQVD)[16] virgin females and 7 to 10 young G-Trace (Evans et al., 6 NAT. METHODS 603-05 (2009)) Gal4 reporter male flies (or vice versa) in the same vial with fly food and fresh yeast paste.

NOTE: Cross of Caspase-sensitive (DQVD) Gal4 and G-Trace flies will produce CaspaseTracker progeny flies. Cross of Caspase-insensitive (DQVA) Gal4 and G-Trace flies will provide negative control flies (see discussion). Fresh yeast paste serves as protein source to enhance egg production, so that increases number of progeny.

1.2. Incubate the files at 18 degrees Celsius (° C.) for 3 to 7 days, and then transfer the flies to new vial to set up a new cross at 18° C. Continue to incubate only the original vial at 18° C. until progeny flies eclose.

NOTE: Transfer the parent flies to new vials to avoid overcrowding of progeny at the original vial. Parent files can produce progeny with fresh food and yeast paste at the first 2 to 3 switches, and then the productivity will significantly decrease with time. Raising files 18° C. can reduce non-specific signal of CaspaseTracker biosensor (see Discussion).

1.3. Select progeny flies with correct phenotypes for following experiments.

NOTE: The transgenes of both caspase-sensitive Gal4 and G-Trace are located at the second chromosome, balanced with CyO balancer. Select the non-curly wing progeny (without CyO), which has both transgenes of caspase-sensitive Gal4 and G-Trace.

2) Application of transient apoptotic induction to CaspaseTracker biosensor flies 2.1. Transfer 10 to 20 newly eclosed female flies to new vial with fresh fly food and fresh yeast paste for 1 day at 18° C. to allow egg chamber production by oogenesis.

NOTE: Keeping the female with male flies might enhance egg chamber production.

2.2. To induce egg chambers to undergo apoptosis by cold shock, transfer the female flies to new vial, which is then placed at $-7°$ C. for 1 hour.

2.3. To induce egg chambers to undergo apoptosis by protein starvation, transfer the female flies to a new vial with 8% sucrose and 1% agar food at 18° C. for 3 days.

NOTE: Protein starvation (non-protein food) can trigger egg chambers to undergo apoptosis (Jenkins et al., 23 TRENDS CELL. BIOL. 567-74 (2013); Drummond-Barbosa, D. & Spradling, A. C., 231 DEV. BIOL. 265-78 (2001); Pritchett et al., 14 APOPTOSIS 969-79 (2009)). Switch flies to new vial with 8% sucrose and 1% agar food every day to keep optimal condition of the sucrose fly food.

2.3. Transfer the stressed flies back to new vial with fresh fly food and fresh yeast paste for 3 day at 18° C. to allow them to recover. Dissect the starved and the starved-recovered flies to obtain egg chambers at ovaries as described (Wong, L. C. & Schedl, P., 51 J. VIS. EXP. (2006)).

NOTE: To dissect *Drosophila* to obtain ovaries, anesthetize flies with $CO_2$, and use 2 pairs of forceps to remove fly head, and the use the forceps to pull the base of the abdomen to remove the ovaries of the flies.

3) Fixation and staining of dissected egg chambers for imaging
3.1. Transfer the dissected egg chambers together with around 0.5 mL phosphate buffered saline (PBS) to 1 mL centrifuge tubes. Allow the eggs to settle down.

NOTE: Coat the plastic pipette tips with 1% bovine serum albumin (BSA) dissolved in water or PBS to prevent the egg chambers to stick at the tips. Perform the following procedures in dark to avoid photobleaching of red fluorescent protein (RFP, also known as DsRed) and green fluorescent protein (GFP) in the egg chambers.

3.2. Remove the PBS by pipetting, and then apply 0.5 mL 4% paraformaldehyde in PBS to fix the egg chambers at room temperature in dark for 20 to 30 minutes. Allow the eggs to settle down.

NOTE: Apply gentle rotation in the following incubation steps.

3.3. Remove the paraformaldehyde by pipetting, and then washed the egg chamber with 0.5 mL PBST (PBS+0.1% Triton X-100) for 3 times. Allow the eggs to settle down. NOTE: Prolonged fixation could reduce the RFP and GFP signals. PBST can avoid egg chambers to stick to the non-BSA coated plastic surface.

3.4. Incubate the egg chambers with PBST overnight at 4° C. with gentle rotation to permeabilize the egg chambers.

3.5. Remove the PBST by pipetting, and then apply 0.5 mL of 10 µg/mL of blue nuclear Hoechst dye in PBST to egg chambers for 1 hour at room temperature to stain for nucleus. Allow the eggs to settle down.

NOTE: Avoid prolonged incubation with nuclear dye as this will increase non-specific signal.

3.6. Remove the nuclear dye by pipetting, and then apply 0.5 mL PBST to wash the egg chambers in the 1 mL centrifuge tubes for 3 times, with 10 minutes incubation with gentle rotation between each washing step. Allow the eggs to settle down.

3.7. Remove all PBST with fine pipette, and then then apply 200 µL anti-bleaching mounting agent (see materials) to incubate the egg chambers for 3 hours or overnight until the egg chambers sink to the bottom of the tube.

3.8. Mount the stained egg chambers by transferring them with 200 µL anti-bleaching mounting agent on glass slide for imaging by pipetting, cover the egg chambers with 20×20 mm glass cover slip, and seal the cover slip on glass slide by putting nail polish at the edge of the cover slip.

3.9. Image the egg chambers using fluorescence or confocal microscope, using a 20×, NA 0.8 Plan-Apochromat objective, with excitation light wavelength 405 nm for nuclear staining (detect emission ~461 nm), 561 nm for RFP (ongoing or recent caspase activity) signal (detect emission ~570 nm), and 488 nm for GFP (past caspase activity) signal (detect emission ~518 nm).

Results

Figure 1B:
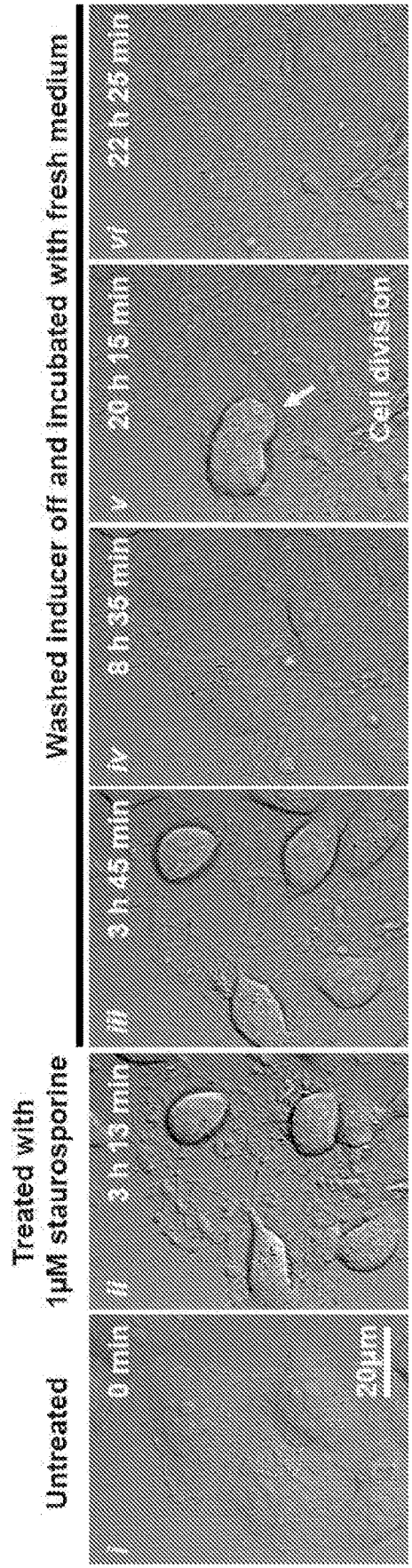
Figure 1C:
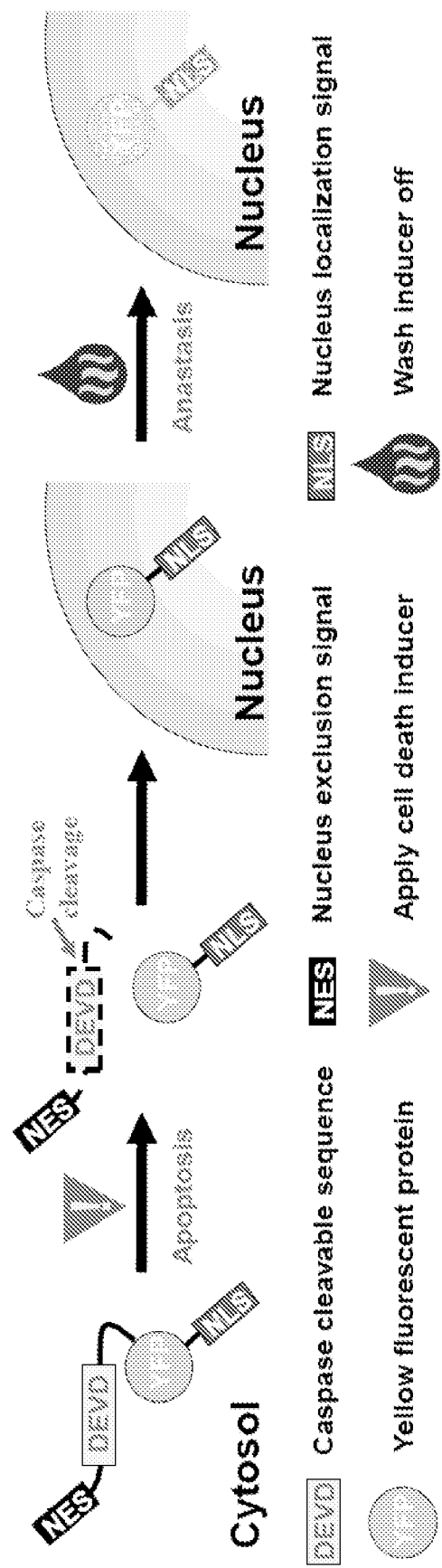
Figure 1D:
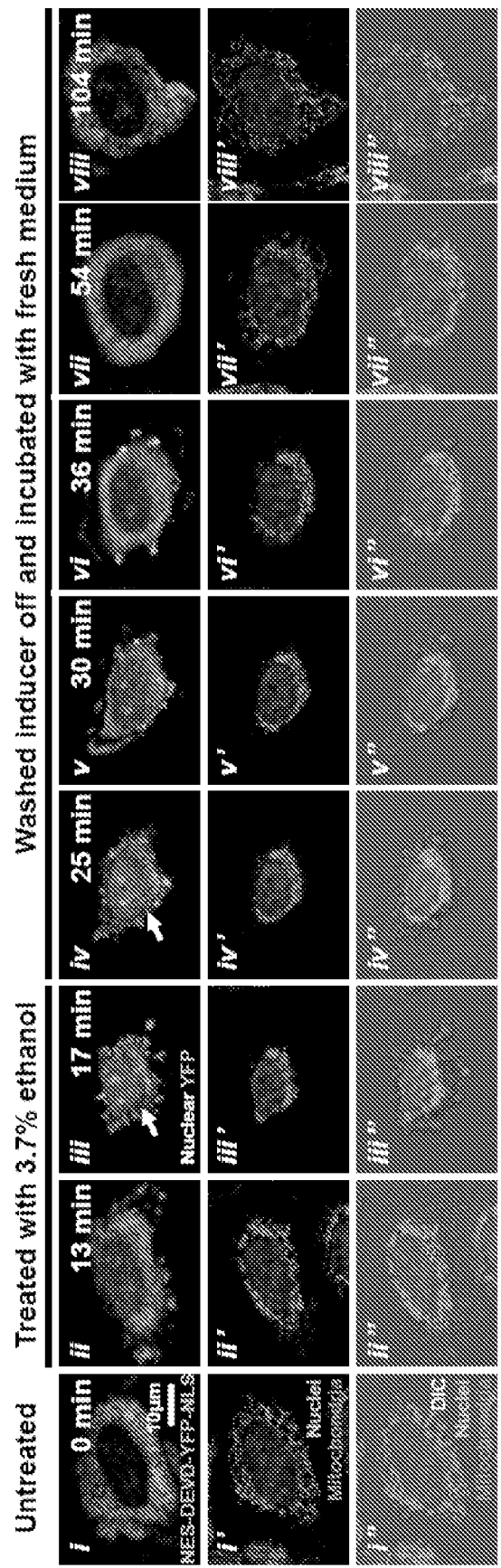
Figure 2C:
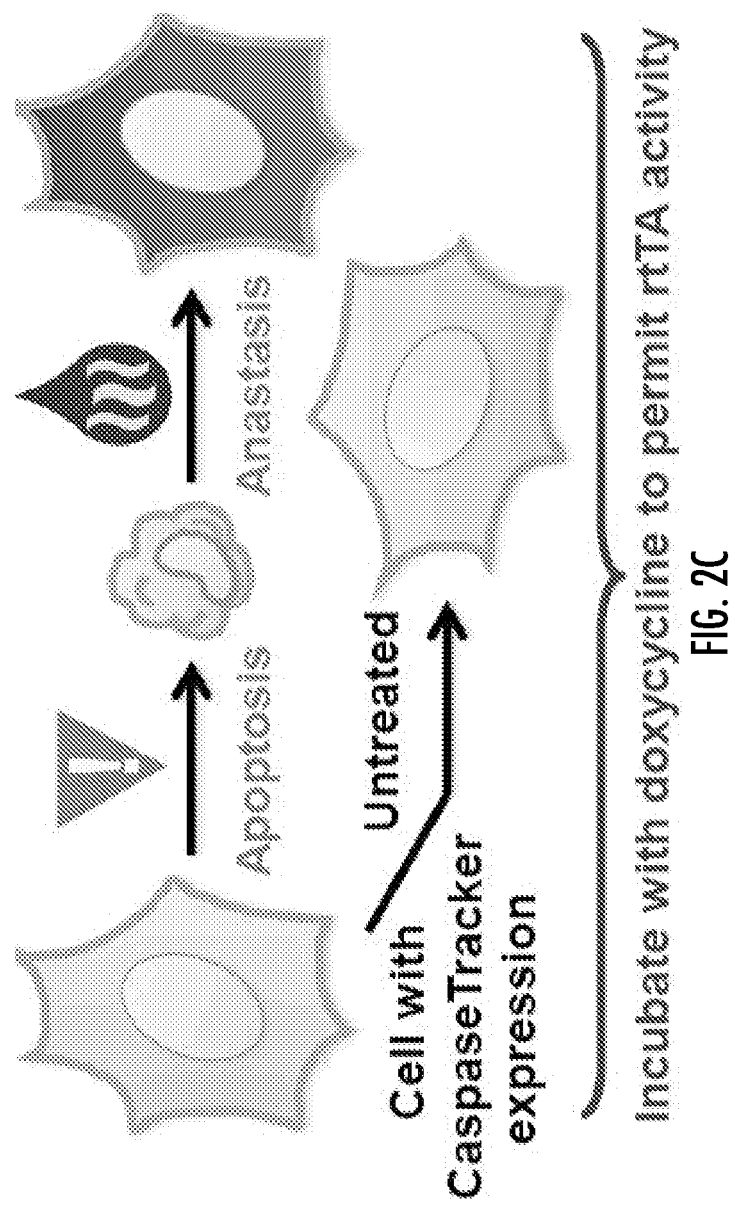
Figure 2D:
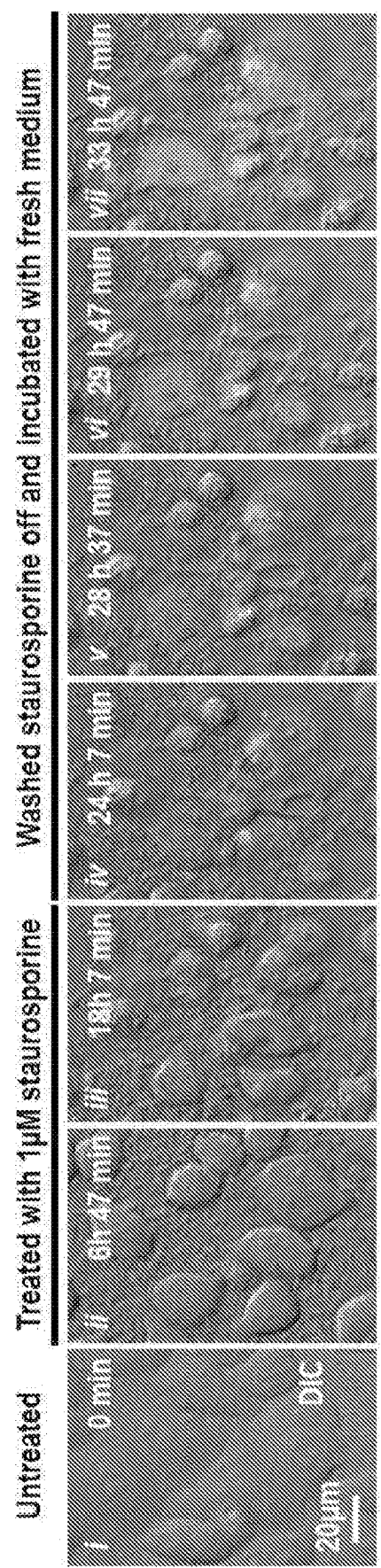
Figure 2E:
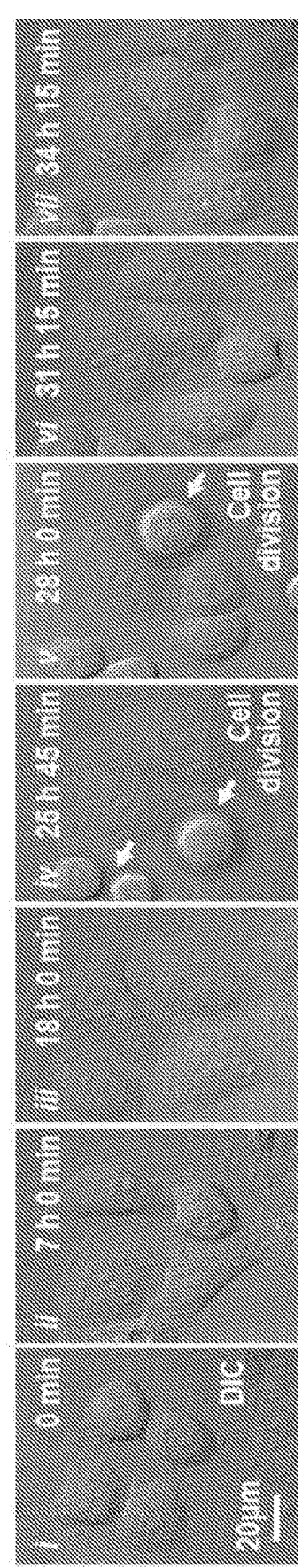

While time-lapse live cell microscopy is a reliable method to tract anastasis in cultured cells (Tang et al., 96 J. VIS. EXP. 51964 (2015)), it is challenging to identify which cells have undergone anastasis in animals, because the recovered cells appear morphologically indistinguishable from the normal health cells that have not attempted cell death. For example, human cervical cancer HeLa cells display morphological hallmarks of apoptosis (Taylor et al. (2008); Jacobson et al. (1997); Kerr et al. (1972), such as cell shrinkage, nuclear condensation, and plasma membrane blebbing in response to cell death stimulus 1 µM staurosporine (FIG. 1A, FIG. 1Bi-ii). After removal of the cell death stimulus and incubated in fresh medium, the dying cells reverse the cell death process by anastasis (Tang et al. (2017); Tang et al. (2015); Tang et al. (2012); Tang et al. (2009), as indicated by morphological recovery (FIG. 1Biii-iv), followed by proliferation (FIG. 1Bv-vi). Our previous studies have also used the "real-time" caspase biosensors, such as ApoAlert (NES-DEVD-YFP-NLS) to demonstrate reversal of apoptosis after caspase activation (Tang et al. (2015); Tang et al. (2012). This biosensor localized at cytosol in healthy cells (FIGS. 1C, 1Di). Upon caspase activation triggered by cell death stimulus 3.7% ethanol, this YFP-based biosensor is cleaved by caspases, and then translocate to nucleus, so that it can label the cells displace on-going caspase activity by nuclear YFP (FIGS. 1C, 1Dii-iii). The apoptotic cell also displays morphological hallmarks of apoptosis during ethanol-induction (Taylor et al. (2008); Kerr et al. (1972)), such as fragmentation of tubular mitochondria, nuclear condensation, cell shrinkage, and plasma membrane blebbing (FIG. 1Dii-iii). Interestingly, after removal of the cell death stimulus, the same cell can recover, and regain normal morphology (FIG. 1Biv-vii). Noticeably, the nuclear signal of the ApoAlert biosensor is removed within 1 hours in the recovered cell (FIG. 1Div-vii), possibly by the same mechanisms of the anastatic cells to remove the damaged cell components (Tang et al. (2012), such as cleaved caspase-3 and PARP generated during apoptosis. Therefore, new strategy is required for tracking anastasis in long term, especially in vivo.

Figure 3A:
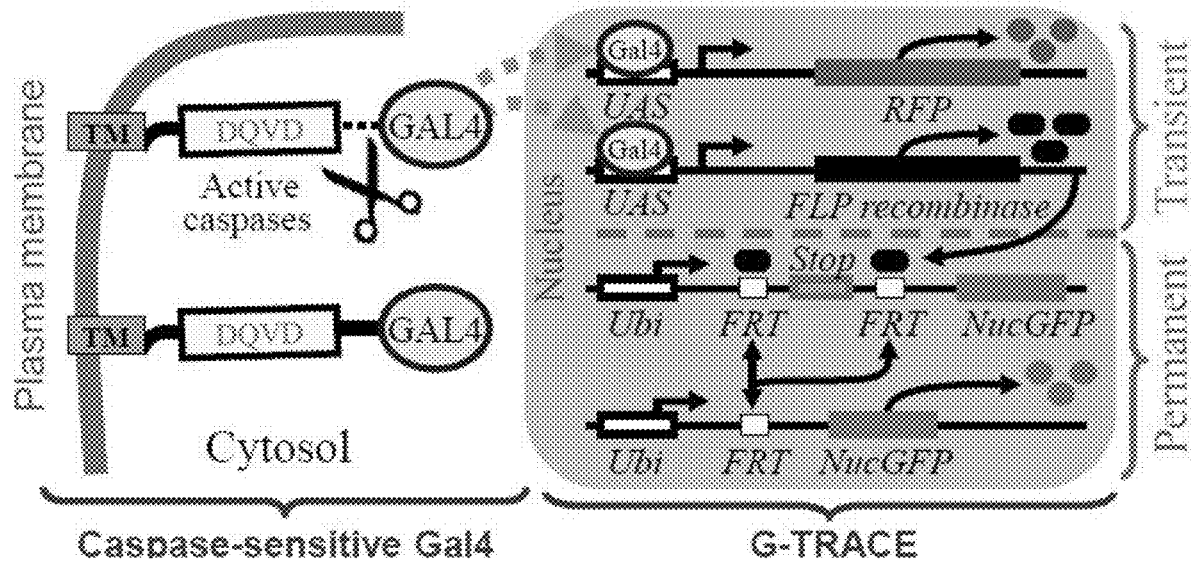
Figure 3B:
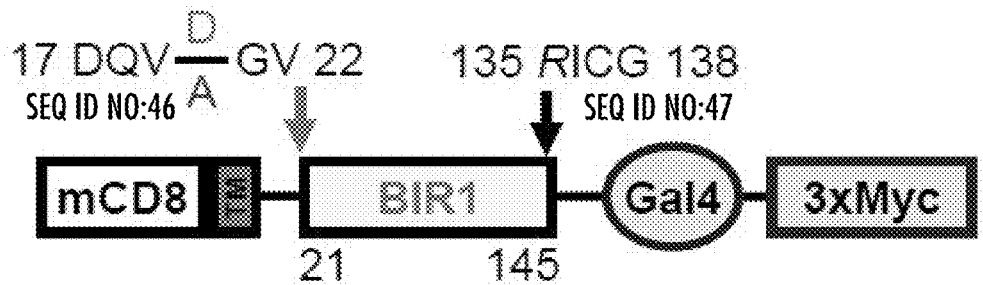

To detect, label and track anastatic cells in live animals, we develop the mammalian CaspaseTracker biosensor system. This biosensor is composed of caspase-sensitive rtTA, and Cre-LoxP-mediated rtTA activity-dependent reporter system (FIG. 3A). In the healthy cells without caspase activity, the transactivator rtTA (reverse tetracycline-controlled transactivator) (Gossen et al., 268 SCIENCE 1766-69 (1995)) is tethered to plasma membrane anchor ($Ly_{11}$) (Inoue et al., 2 NAT. METHODS 415-18 (2005); Yamanashi et al., 7 MOL. CELL. BIOL. 237-43 (1987)), nucleus exclusion signal (NES) of Map Kinase (MAPKK)(Fukuda et al., 271 J. BIOL. CHEM. 20024-28 (1996)), and estrogen receptor variant ($ER^{T2}$) (Feil et al., 237 BIOHCEM. BIOPHYS. RES. COMMUN. 752-57 (1997)) through caspase-cleavable (DEVD) (Lazebnik et al., 371 NATURE 346-67 (1994)) linkers derived from PARP (FIGS. 3A, 3B). As tethered rtTA cannot translocate from cytosol to nucleus, the rtTA reporter remains inactive. Upon caspase activation in response to cell death stimulus, activated caspases cleave the DEVD linkers to release rtTA, which then translocates to the nucleus to activate the rtTA reporter (FIG. 3A). The nuclear rtTA binds to the tet response element (TRE) to triggers transient expression of Cre recombinase, which leads to an irreversible recombination event that removes the stop cassette between the CAG promoter and the coding sequences for red fluorescent protein (DsRed). This results in permanent expression of DsRed, which serves as the permanent fluorescent marker of those cells that can remain alive after they have experienced caspase activity, as well as their progeny (FIG. 3C). Doxycycline, which is essential to permit rtTA activity, is applied at the time when the biosensor need to be turn on.

To test the mammalian CaspaseTracker biosensor, we introduce the biosensor to the HeLa cells by transient transfection, expose the cells with transient cell death stimulus, and monitor the recovery of the cells by time-lapse live cell confocal microscopy as we described (Tang et al., 96 J. VIS. EXP. 51964 (2015)). Doxycycline (1 µg/ml) is applied to the cell culture medium to turn on the biosensor throughout the experiment. In response to the cell death stimuli 1 µM staurosporine, the induced cells display hallmark of apoptosis including cell shrinkage and plasma membrane as expected (FIG. 3Di-iii). After wash and incubate the cells with fresh culture medium, anastasis occurs in the dying cells, as induced by their morphological recovery (FIG. 3Div-viii). Importantly, the recovered cells express DsRed during and after anastasis (FIG. 3Div-viii), but not the non-recovered cells (FIG. 3Div-viii), nor the cells without exposed to cell death stimuli (FIG. 3E). This indicates that the mammalian CaspaseTracker is a unique tool to identify and permanently label the cells that recovered from caspase-activation, enabling the long-term track to study the fate of anastatic cells.

To detect and track anastasis in live animals, the CaspaseTracker biosensor transgenic animals are first created and tested in *Drosophila melanogaster* (Tang et al., 5 SCI. REP. 9015 (2015)). Modified from the mammalian CaspaseTracker biosensor, the *Drosophila* dual biosensor is composed of a caspase-sensitive Gal4 (Tang et al. (2015), and the Gal4 reporter G-Trace (Evans et al. (2009)) (FIG. 3A). In the cells without caspase activity, the yeast transcription factor Gal4 is tethered to a plasma membrane anchor (mCD8) domain through a caspase-cleavable linker (DQVD) derived from DIAP1 (FIG. 3B), with a D135R mutation to abolish the drICE caspase inhibitory function in the BIR1 domain[16]. As tethered Gal4 cannot translocate to nucleus, the Gal4 reporter G-Trace remains inactive in the cells without caspase activity. Upon caspase activation, activated caspases cleave the DQVD linker to release Gal4, which then translocates to the nucleus to activate the G-Trace reporter (FIG. 3A). Gal4 binds to the specific upstream activating sequences (UAS) to triggers transient expression of RFP, which serves as the reporter of recent or current caspase activity until the Gal4 (caspase) activity stop and then RFP protein is degraded. Gal4 also triggers the expression of FLP recombinase, which leads to a recombination event that removes the stop cassette between the ubiquitin (Ubi) promoter and the coding sequences for nuclear-targeted GFP (nucGFP). This results in permanent expression of nucGFP, which serves as the permanent marker of those cells that have experienced caspase activity and remain alive. Transgenic CaspaseTracker *Drosophila* is generated with this dual biosensor system.

To test the *Drosophila* CaspaseTracker biosensor for detecting apoptosis and anastasis in vivo, the CaspaseTracker female flies are subjected to physiological stress (FIG. 3C) such as cold shock (Tang et al., 5 SCI. REP. 9015 (2015)), which can efficiently trigger cell death including apoptosis in various tissues such as egg chambers of fruit flies (Yi et al., 12 APOPTOSIS 1183-93 (2007)). As expected, CaspaseTracker is not activated at the healthy egg chambers of well-fed flies as apoptosis is not occurred (FIG. 3D), but is activated in the stressed flies in 1 day after cold shock induction (FIG. 3E). Egg chambers exhibiting apoptotic morphologies, including cell shrinkage and nuclear condensation, display RFP and GFP biosensor activity, indicating recent or on-going (RFP) and past (GFP) caspase activity (FIG. 3E). However, at 3 days after the flies are kept in normal condition, the GFP, but not RFP, express in the egg chambers (FIG. 3F), inducing that the egg chambers experienced the past caspase activity, and survive.

To further test reversibility of cell death process in egg chambers (Tang et al. (2015)), CaspaseTracker female flies are fed with 8% sucrose in 1% agar for 3 days, as previous studies demonstrate that protein starvation can trigger caspase-mediated apoptosis in tissues with somatic and germ cells including egg chambers (Drummond-Barbosa, D. & Spradling, A. C., 231 DEV. BIOL. 265-78 (2001)). As expected, CaspaseTracker is activated in egg chambers after 3 days of protein starvation (FIG. 3G). The dying egg chambers exhibiting apoptotic morphologies display RFP and GFP biosensor activity, indicating recent or on-going (RFP) and past (GFP) caspase activity (FIG. 3G). To demonstrate that CaspaseTracker can track the recovered cells that previously experienced caspase activation after a death stimulus, the starved flies are then transferred to normal protein-containing fly food. As expected, the recovered egg chambers of these re-fed flies lack the RFP transient caspase reporter, indicating no recent or ongoing caspase activity (FIG. 3H). However, these re-egg chambers display the GFP caspase reporter (FIG. 3H), indicating that the cells in these egg chambers have reversed apoptosis at a point after caspase activation. The CaspaseTracker biosensor activity is triggered by caspase activity, because replacing the caspase cleavable DQVD with caspase non-cleavable DQVA peptide at the biosensor abolish its activity (FIG. 3I).

Figure 3J:
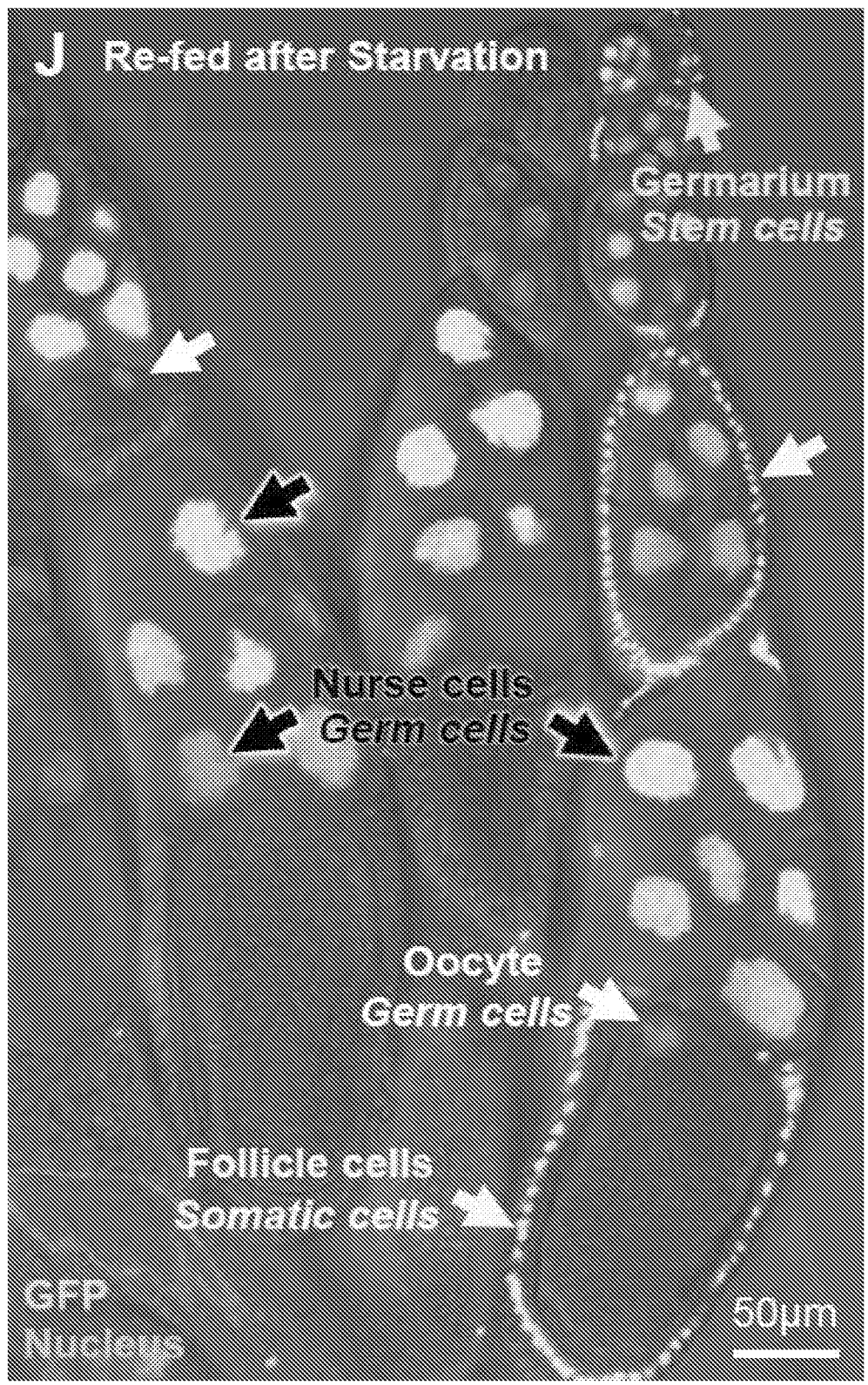

After the CaspaseTracker *Drosophila* recovered from protein starvation, we found that multiple cell types of egg chambers, such as somatic (follicle) cells and germline cells (nurse cells and oocytes), display only GFP, but not RFP (FIG. 3J) (Tang et al., 5 SCI. REP. 9015 (2015)), indicating that these cells can undergo anastasis after caspase activation. Importantly, the starved and re-fed female flies lay fertile eggs that can produce GFP-expressing progeny flies (Tang et al. (2015)), suggesting that potentially many cells can reverse cell death process after caspase activation and regain apparently normal function. Future studies are needed to determine if progeny flies that survive as a consequence of anastasis exhibit permanent sequelae.

Discussion

The CaspaseTracker dual biosensor system is a novel and unique tool that allows detection of recent or ongoing caspase activity, and tracking of cells that have reversed apoptosis and survive after experiencing caspase activity in vivo. While caspase activity is traditionally known as the hallmark of apoptosis, recent studies reveal that non-apoptotic caspase activity plays potential roles in diverse normal cell functions, such as regulation of neuronal activity (Li et al., 141 CELL 859-71 (2010); Jonas et al., 101 PROC. NATL. ACAD. SCI. U.S.A. 13590-95 (2004)), learning and memory (Neukomm, L. J. & Freeman, M. R., 24 TRENDS CELL. BIOL. 515-23 (2014); Yu, F. & Schuldiner, O., 27 CURR. OPIN. NEUROBIOL. 192-98 (2014); Maor-Nof, M. & Yaron, A., 23 CURR. OPIN. NEUROBIOL. 990-96 (2013); Hyman, B. T. & Yuan, J., 13 NAT. REV. NEUROSCI. 395-406 (2012)), suppression of necroptotic cell death (Kaiser et al., 471 NATURE 368-72 (2011); Oberst et al., 471 NATURE 363-67 (2011)), spermatid individualization (Kaplan et al., 19 DEV. CELL 160-73 (2010); Arama et al., 4 DEV. CELL 687-97 (2003)), and microRNA processing (Weaver et al., 3 ELIFE (2014)). In addition to apoptosis and anastasis, the CaspaseTracker biosensor system can detect non-apoptotic caspase activity, which presents in brain and optic lobes, cardia, guts, Malpighian tubules, trachea, and other tissues (Tang et al., 117 J. VIS.EXP. (2016); Tang et al., 5 SCI. REP. 9015 (2015)). To study anastasis in live animals, it is critical to choose the tissues with cells that exhibit no caspase biosensor activity under normal physiological conditions, but can be induced to undergo caspase activation by transient cell death induction. Egg chambers are ideal, because they often do not have caspase activity from germarium to stage 10 during oogenesis (Jenkins et al., 23 TRENDS CELL. BIOL. 567-74 (2013); Pritchett et al., 14 APOPTOSIS 969-79 (2009); Baum et al., 14 CELL DEATH DIFFER. 1508-17 (2007)).

Exposing female *Drosophila* to transient environmental stresses, such as protein starvation and cold shock, can efficiently trigger apoptosis in egg chambers (Pritchett et al. (2009); Chaturvedi et al., 99 J. NATL. CANCER INST. 1634-43 (2007); Yi et al. (2007)). Critical steps within the protocol include avoiding prolonged apoptotic induction to flies. The optimized conditions of protein starvation (8% sucrose in 1% agar for 3-days) and cold shock (1 hour at −7° C.) to female flies can trigger caspase-mediated apoptosis in egg chambers, and allow them to recover after the stressed flies are returned to normal condition (Tang et al., 5 SCI. REP. 9015 (2015)). Prolonged cell death stimulus can trigger more egg chambers to undergo apoptosis, but the recovery rate is also reduced, possibly because the dying egg chambers experience massive damage beyond repair.

An addition critical step in this protocol is to reduce the CaspaseTracker background signal in egg chambers by crossing, raising and maintaining the CaspaseTracker flies at low temperature such as 18° C. While the majority of egg chambers from optimally reared flies do not display caspase activity in the germarium through stage 10 during oogenesis (Pritchett et al.

(2009)), an around 1% of egg chambers could exhibit caspase biosensor activity without cell death induction. This may reflect the normal attrition rate due to innate errors or may be triggered un-intentionally during oogenesis by standard laboratory conditions. As Gal4 displays less activity in flies at low temperature (Duffy, J. B., 34 GENESIS 1-15 (2002)), raising flies at 18° C., rather than at room temperature, can reduce the endogenous signal that activates the CaspaseTracker system. Alternatively, switching files to high temperature, such as 29° C., can increase sensitive of CaspaseTracker system, due to increase in Gal4 activity (Duffy et al. (2002)), and potentially other endogenous temperature-dependent enzymatic activities.

It is important to distinguish the CaspaseTracker-labeled cells that undergo apoptosis and anastasis from cells that exhibit non-apoptotic caspase activity. Apoptotic cells express RFP, and often GFP in prolonged apoptotic induction, as the cells has ongoing caspase activity that cleave-activated Gal4, which activate the transient (Gal4 activity-dependent RFP) and permanent (Gal4 triggered FLPase-FRT mediated GFP) labeling reporters at the G-Trace system. Apoptosis of these cells can be confirmed by morphological hallmark such us nuclear condensation stained with nuclear dye (Pritchett et al. (2009); Taylor et al. (2008)), and also biochemical hallmark for cleaved caspases by immunostaining (Fan, Y & Bergmann, A., 17 CELL DEATH DIFFER. 534-39 (2010)). For the cells that reversed apoptosis, they display permanent GFP expression due to the FLPase-mediated recombination event of G-Trace system. These cells don't have RFP expression as the cells don't have on-going caspase activity, nor other hallmarks of apoptosis (Tang et al., 5 SCI. REP. 9015 (2015)). These cells also display normal nuclear morphology. The cells that have on-going non-apoptotic caspase activity often display both RFP and GFP expression, with normal nuclear morphology (Tang et al. (2015)).

At the same time, it could be difficult to distinguish the cells that experienced anastasis, and the past non-apoptotic caspase activity, because both of the cells only display GFP, and with normal nuclear morphology. Therefore, careful control experiments are needed to be included (Tang et al. (2015)). For examples, to study anastasis in egg chambers, it is essential to examine the GFP expression at both of the stressed-recovered flies and the non-stressed flies (negative control). The recovered flies should more GFP-expressing cells than the non-stressed flies, if anastasis occurs in the recovered cells and tissues. Besides, it is also important to distinguish the signal of CaspaseTracker from nonspecific signal of auto-fluorescence such as from cuticle and fat bodies. We generated the negative control biosensor flies, with only different in DQVD to DQVA mutation to abolish the caspase sensitivity of the control biosensor (Tang et al. (2015)). The signal presents at the caspase sensitive (DQVD) but not the negative control (DQVA) biosensor flies is the real signals triggered by caspase activity, rather than auto-fluorescence.

Our current *Drosophila* dual CaspaseTracker biosensor can identify the cells with "recent" caspase activity by the RFP, and the cells with "past" caspase activity by GFP (Tang et al. (2015)). At the same time, the RFP is not the "real-time" caspase activity indicator, because it takes a few hours of reaction time for Gal4 to drive the expression of RFP in response to caspase activity. To add the "real time" function, our *Drosophila* CaspaseTracker biosensor can be combined with the recently developed iCasper biosensor (To et al., 112 PROC. NATL. ACAD. SCI. U.S.A. 3338-43 (2015)), a "real-time" and "dark to bright" in vivo biosensor that only show far red signal when it is cleaved by caspases.

Figure 4:
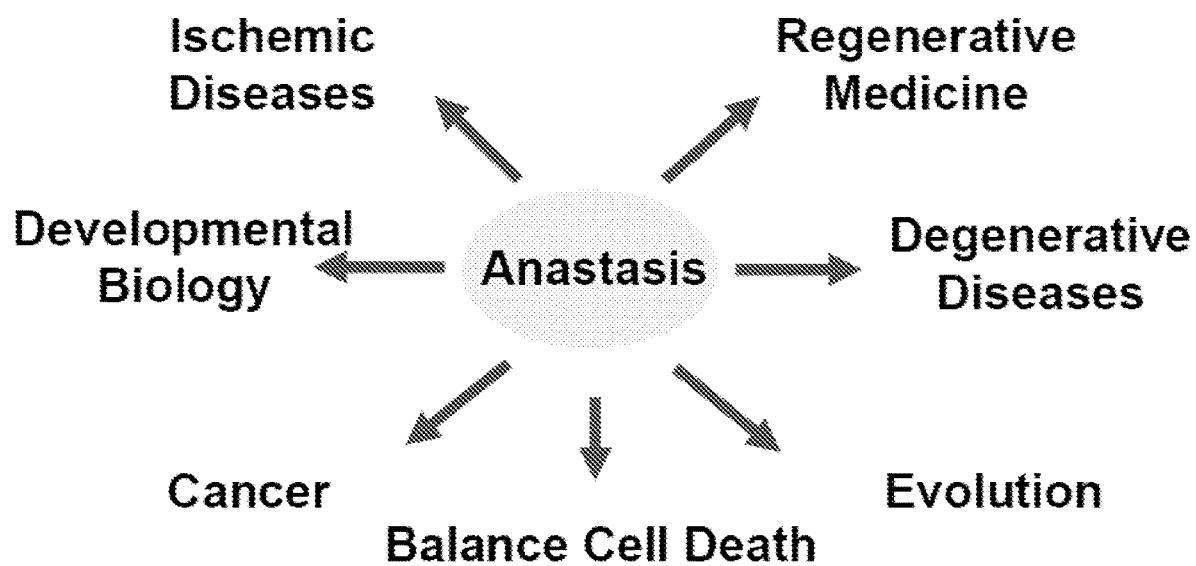
FIG. 4. Physiological, pathological and therapeutic implications of anastasis (reprinted with permission from Tang et al., 6 F100RES 43 (2017).

The in vivo CaspaseTracker biosensor will facilitate pursuit of the yet unknown functions, mechanisms and therapeutic implications of anastasis (FIG. 4). To reveal the molecular signature of anastasis, we performed the time-course whole-genome gene expression microarray study to analyze the mouse primary liver cell during reversal of ethanol-induced apoptosis, and interestingly found striking changes in transcription of genes involved in multiple pathways including pro-survival, DNA damage and stress response, angiogenesis, cell migration and transformation (Tang et al. (2017); Tang et al. (2012)). Our finding is supported by our RT-PCR validation during the recovery of the human liver cancer HepG2 cells (Tang et al. (2017)), and also the following independent study in HeLa cells (Sun et al., J. CELL. BIOL. jcb.201706134 (2017)). To study the physiological, pathological and therapeutic potentials of anastasis, it is important to identify the anastatic cells and track their fate in small animals. Our *Drosophila* and mammalian CaspaseTracker biosensors would be the useful tools to test the potential contributions of anastasis in tissue recovery, stress-induced mutagenesis, tumor evolution, cancer recurrence and metastasis. The finding could offer potential to identify revolutionary new therapeutic approaches for intractable diseases by mediating cell death and survival through controlling anastasis.

We claim:

1. A polypeptide comprising SEQ ID NO:2.
2. A polypeptide comprising SEQ ID NO:4.
3. A polypeptide comprising SEQ ID NO:28.
4. A polypeptide comprising SEQ ID NO:30.
5. A polypeptide comprising SEQ ID NO:32.
6. A polypeptide comprising SEQ ID NO:34.
7. A polypeptide comprising SEQ ID NO:36.
8. A polypeptide comprising SEQ ID NO:38.
9. A polypeptide comprising SEQ ID NO:40.
10. An apoptosis biosensor comprising a polypeptide of claim 1 and a reporter system.
11. The apoptosis biosensor of claim 10, wherein the reporter system is G-Trace reporter system.
12. A polynucleotide construct comprising a polynucleotide encoding SEQ ID NO:2.
13. A polynucleotide construct comprising a polynucleotide encoding SEQ ID NO:4.
14. A polynucleotide construct comprising a polynucleotide encoding SEQ ID NO:28.
15. A polynucleotide construct comprising a polynucleotide encoding SEQ ID NO:30.
16. A polynucleotide construct comprising a polynucleotide encoding SEQ ID NO:32.
17. A polynucleotide construct comprising a polynucleotide encoding SEQ ID NO:34.
18. A polynucleotide construct comprising a polynucleotide encoding SEQ ID NO:36.
19. A polynucleotide construct comprising a polynucleotide encoding SEQ ID NO:38.
20. A polynucleotide construct comprising a polynucleotide encoding SEQ ID NO:40.

* * * * *